(12) United States Patent
Backstein

(10) Patent No.: US 11,717,612 B1
(45) Date of Patent: Aug. 8, 2023

(54) MULTI-PURPOSE AUTOMATIC INJECTOR

(71) Applicant: Robert Backstein, Toronto (CA)

(72) Inventor: Robert Backstein, Toronto (CA)

( * ) Notice: Subject to any disclaimer, the term of this patent is extended or adjusted under 35 U.S.C. 154(b) by 0 days.

(21) Appl. No.: 17/994,146

(22) Filed: Nov. 25, 2022

Related U.S. Application Data

(60) Provisional application No. 63/406,689, filed on Sep. 14, 2022.

(51) Int. Cl.
*A61M 5/20* (2006.01)
*A61M 5/315* (2006.01)
*A61B 5/15* (2006.01)

(52) U.S. Cl.
CPC ..... *A61M 5/2066* (2013.01); *A61B 5/150122* (2013.01); *A61M 5/31578* (2013.01); *A61M 2205/36* (2013.01); *A61M 2205/50* (2013.01)

(58) Field of Classification Search
CPC ............ A61M 5/2066; A61M 5/31578; A61M 2205/36; A61M 2205/50; A61B 5/150122
USPC ........................................................ 604/113
See application file for complete search history.

(56) References Cited

U.S. PATENT DOCUMENTS

| | | | |
|---|---|---|---|
| 5,578,014 A * | 11/1996 | Erez | A61B 5/15113 604/192 |
| 6,980,855 B2 | 12/2005 | Cho | |
| 8,016,774 B2 | 9/2011 | Freeman et al. | |
| 8,708,966 B2 | 4/2014 | Allen et al. | |
| 8,753,314 B2 * | 6/2014 | Mendez | A61B 34/30 604/188 |
| 2007/0060989 A1 | 3/2007 | Deem et al. | |
| 2010/0049126 A1 | 2/2010 | Bronfeld et al. | |
| 2010/0312195 A1 * | 12/2010 | Johansen | A61M 5/2033 604/192 |
| 2020/0330737 A1 | 10/2020 | Herndon et al. | |

FOREIGN PATENT DOCUMENTS

WO 2016022865 A1 2/2016

* cited by examiner

*Primary Examiner* — Phillip A Gray

(57) ABSTRACT

A multi-purpose automatic injector, comprising a base unit having a forward end and a rearward end and arranged along a longitudinal axis; a cartridge containing a medicament, the cartridge being coupled adjacent to the forward end of the base unit; a drive assembly attached to the base unit and configured to be actuated by a computerized controller; at least one piercing element configured to be operatively coupled with the drive assembly and configured to be movable by the drive member relative to the cartridge in a reciprocating manner upon receipt of a corresponding signal from the computerized controller.

20 Claims, 50 Drawing Sheets

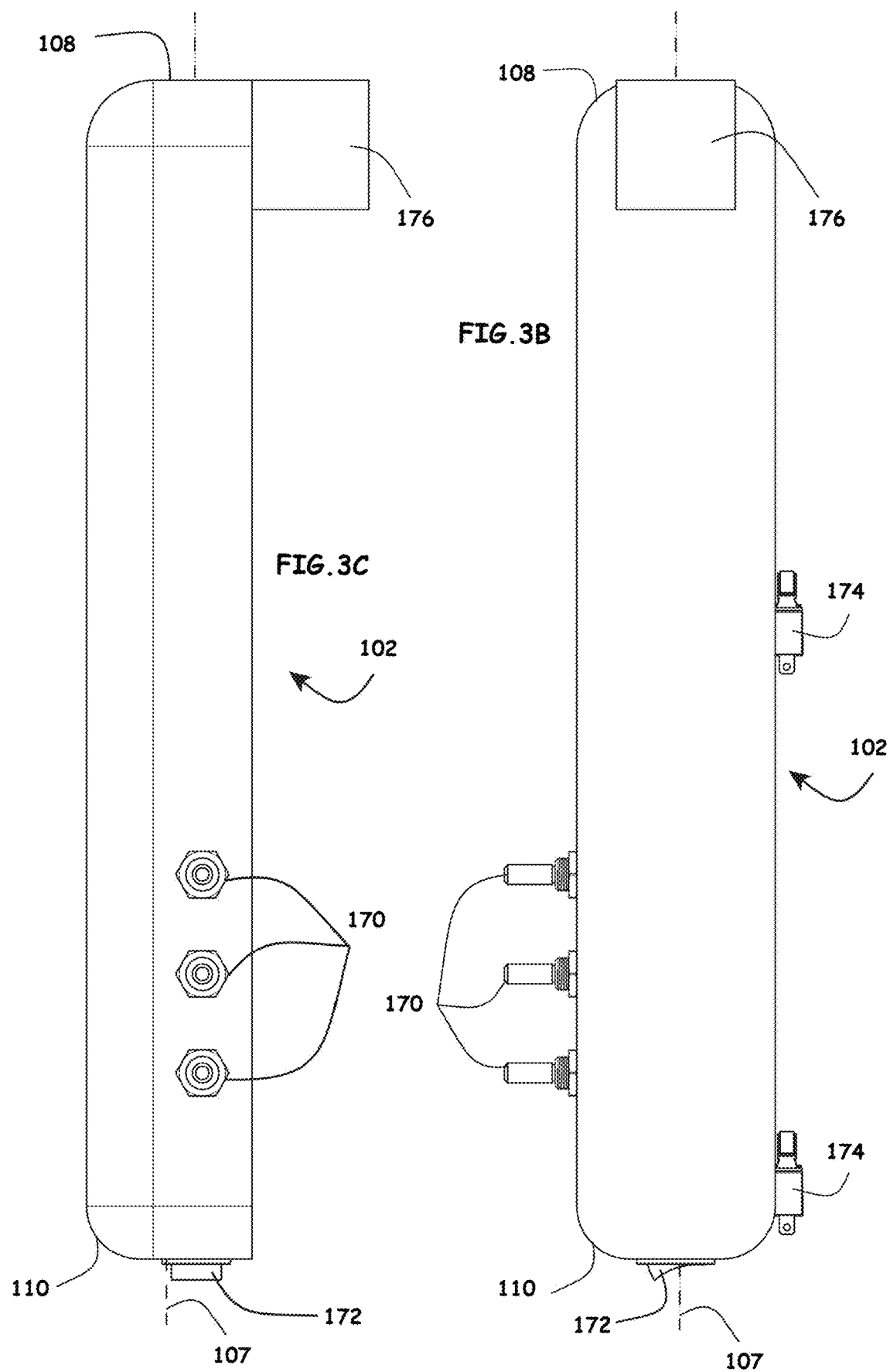

Mode Selection via mode selection inputs:
Body Area Sensitivity: eg. Low, Moderate, High, Super
Final Needle Penetration Depth: eg. 1 mm, 2mm, 3mm, 4mm...
Syringe Volume and Brand: eg. BD 1cc, BD 2 cc, BD 3 cc, Terumo 1 cc, Terumo 2 cc, Terumo 3cc...
Needle Length and Brand: eg. BD 5 mm, BD 10 mm, BD 30 mm, Terumo 5 mm, Terumo 10 mm, Terumo 30 mm
Injection Rate: eg. Very Slow, Moderate, Rapid

User connects needle 142 to syringe 140 filled with the desired volume of medicament 150. The needle-syringe complex is secured onto the syringe holding element 130

FIG.15B

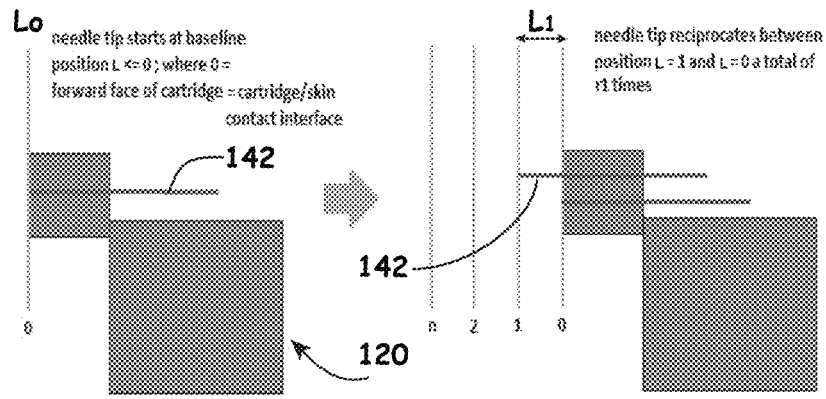
FIG.16A
FIG.16B
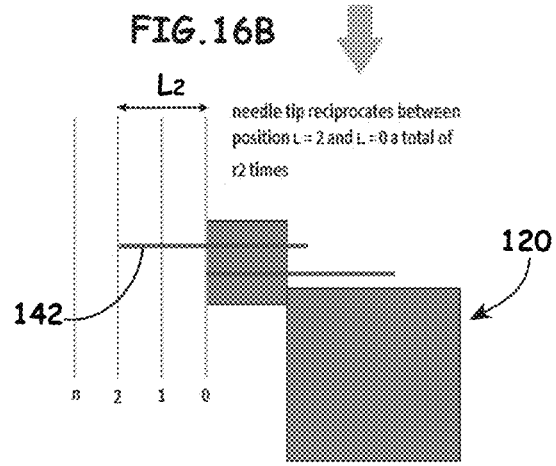
FIG.16C
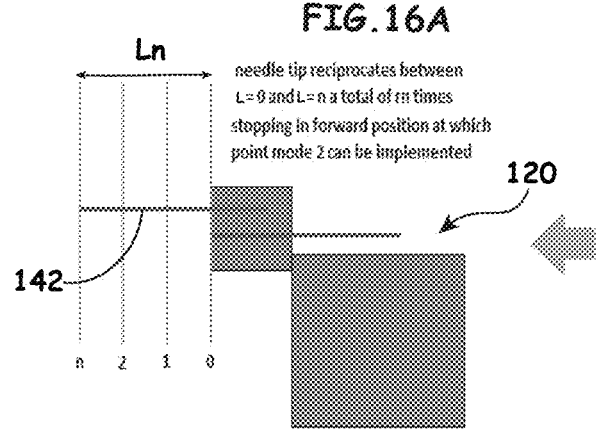
FIG.16D

MULTI-PURPOSE AUTOMATIC INJECTOR

REFERENCE TO RELATED APPLICATIONS

Reference is hereby made to U.S. Patent Application Ser. No. 63/406,689, filed Sep. 14, 2022 and entitled "MULTI-PURPOSE AUTOMATIC INJECTOR", the disclosure of which is hereby incorporated by reference in its entirety and priority of which is hereby claimed.

FIELD OF THE INVENTION

The present invention generally relates to an automatic injector, and more specifically to a multi-purpose automatic injector, adapted to reduce pain during administration/aspiration of substance to/from a patient.

BACKGROUND OF THE INVENTION

Many automatic injectors adapted for administration/aspiration of substance to/from a patient are known. Traditionally, local anesthetics, such as lidocaine and marcaine are injected into the desired treatment area to allow for the painless execution of an invasive medical procedure, however the injection of the anesthetic is a painful procedure itself.

It is known that the pain caused by skin penetration by a needle is effected by the stimulation of pain-sensitive nerve endings, known as nociceptors. An anatomical gap exists between the skin surface and the most superficial nociceptors. It is thus possible to puncture the skin with a needle at depths above the nociceptors painlessly.

An alternative method is known to deliver a substance into the skin of a patient, using a reciprocating linear motion of the needle/s, such as tattoo guns and microneedling devices. These systems employ repetitive needle penetrations to deposit a substance into the skin. Repetitive penetration and withdrawal of the needles into the skin leads to an accumulating volume of substance being deposited at a given skin depth, without the use of pressurized injection.

It would be advantageous if a means to reduce or eliminate the pain associated with the injection of medicament, or the pain associated with needle penetration into the skin was readily available.

The following publications are believed to represent the current state of the art:

US Patent App. No. 2010/0049126A1, WO Pat. No. 2016022865, U.S. Pat. No. 8,016,774, TW Pat. No. 1689326, U.S. Pat. No. 8,708,966 B2, U.S. Pat. No. 6,980,855 B2, US Patent App. No. 2020/0330737 A1, US Patent App. No. 20070060989A1.

SUMMARY OF THE INVENTION

The present invention seeks to provide an improved automatic injector. There is thus provided in accordance with an embodiment of the present invention that a multi-purpose automatic injector for use with a syringe containing a first medicament and having a needle attached to one end thereof and a plunger inserted into the syringe at another end thereof and being slidably displaceable with respect thereto, comprising a base unit having a forward end and a rearward end and arranged along a longitudinal axis; a cartridge containing a second medicament, the cartridge being coupled adjacent to the forward end of the base unit; a drive assembly attached to the base unit and configured to be operatively coupled with the syringe, wherein in a first mode of operation, the drive assembly is configured to displace the syringe with the needle relative to the base unit, such that the needle moves relative to the cartridge in a reciprocating manner; and in a second mode of operation, the drive assembly is configured to displace the plunger rod relative to the syringe to effect ejection of fluid therefrom.

Preferably, the multi-purpose automatic injector also comprising a computerized controller configured to govern the drive assembly, which comprises one motor. Alternatively, the multi-purpose automatic injector also comprising a computerized controller configured to govern the drive assembly, which comprises two motors.

Further preferably, in the first mode of operation, the second medicament is caused to be deposited into an injection site using an outer surface of the needle and in the second mode of operation, the first medicament is caused to be injected into the injection site through the needle. Still further preferably, the computerized controller utilizes an automated algorithm to govern movement of the syringe relative to the cartridge. Yet further preferably, the multi-purpose automatic injector also comprising at least one sensor, which is operatively coupled to the computerized controller and configured to provide an output indication if the base unit or the cartridge is disengaged from the skin of a patient or if pressure on the skin of the patient is reduced beyond a particular threshold value.

Yet further preferably, the computerized controller is configured to disable movement of the at least one needle relative to the cartridge and to retract the needle into the cartridge upon receipt of the output indication from the at least one sensor.

In accordance with another embodiment of the present invention, a multi-purpose automatic injector for use with a syringe containing a first medicament and having a needle attached to one end thereof and a plunger inserted into the syringe at another end thereof and being slidably displaceable with respect thereto, comprising: a base unit having a forward end and a rearward end and arranged along a longitudinal axis; a cartridge containing a second medicament, the cartridge being coupled adjacent to the forward end of the base unit; a drive assembly attached to the base unit and configured to be operatively coupled with the syringe; wherein, in a first mode of operation, the drive assembly is configured to displace the syringe with the needle relative to the base unit, such that the needle moves relative to the cartridge in a reciprocating manner to enable depositing of the second medicament into an injection site and in a second mode of operation, the plunger rod is manually axially forwardly displaced relative to the syringe to enable injection of the first medicament into the injection site.

Preferably, in the first mode of operation, the drive assembly is configured to displace the syringe with the needle relative to the base unit, such that the needle moves relative to the cartridge in a reciprocating manner; and in the second mode of operation, the drive assembly is configured to displace the plunger rod relative to the syringe to effect ejection of fluid therefrom.

Further preferably, the multi-purpose automatic injector also comprising a computerized controller configured to govern the drive assembly, which comprises one motor. Alternatively, the multi-purpose automatic injector also comprising a computerized controller configured to govern the drive assembly, which comprises two motors.

Still further preferably, the computerized controller utilizes an automated algorithm to govern movement of the syringe relative to the cartridge. Yet further preferably, the multi-purpose automatic injector also comprising at least one sensor, which is operatively coupled to the computerized controller and configured to provide an output indication if the base unit or the cartridge is disengaged from the skin of a patient or if pressure on the skin of the patient is reduced beyond a particular threshold value.

Preferably, the computerized controller is configured to disable movement of the at least one needle relative to the cartridge and to retract the needle into the cartridge upon receipt of the output indication from the at least one sensor. Further preferably, in the first mode of operation, the second medicament is caused to be deposited into an injection site using an outer surface of the needle and in the second mode of operation, the first medicament is caused to be injected into the injection site through the needle.

In accordance with still another embodiment of the present invention, a multi-purpose automatic injector, comprising: a base unit having a forward end and a rearward end and arranged along a longitudinal axis; a cartridge containing a medicament, the cartridge being coupled adjacent to the forward end of the base unit; a drive assembly attached to the base unit and configured to be actuated by a computerized controller; at least one piercing element configured to be operatively coupled with the drive assembly and configured to be movable by the drive member relative to the cartridge in a reciprocating manner upon receipt of a corresponding signal from the computerized controller.

Preferably, the computerized controller utilizes an automated algorithm to govern movement of the at least one needle relative to the cartridge. Further preferably, the multi-purpose automatic injector also comprising at least one sensor, which is operatively coupled to the computerized controller and configured to provide an output indication if the base unit or the cartridge is disengaged from the skin of a patient or if pressure on the skin of the patient is reduced beyond a particular threshold value.

Further preferably, the computerized controller is configured to disable movement of the at least one piercing element relative to the cartridge and to retract the piercing element into the cartridge upon receipt of the output indication from the at least one sensor. Still further preferably, the piercing element is one of a blood-collection needle connected to a vacuum collection tube, an intravascular catheter, a finger-stick lancet, a hypodermic needle, a piercing needle and an abrading bur secured to a chuck of a rotary tool.

Yet further preferably, the drive assembly comprises one motor. Alternatively, the drive assembly comprises two motors.

In an embodiment of the present invention, the multi-purpose automatic injector also comprises a heating mechanism operatively coupled thereto and configured to transmit heat to the medicament.

In accordance with an embodiment of the present invention, a method of operating a multi-purpose automatic injector, comprising the steps of: providing a base unit having a forward end and a rearward end and arranged along a longitudinal axis; a cartridge containing a medicament, the cartridge being coupled adjacent to the forward end of the base unit; a drive assembly attached to the base unit and configured to be actuated by a computerized controller; utilizing an automated algorithm for providing a suitable signal to the computerized controller for: first longitudinally displacing at least one piercing element, which is configured to be operatively coupled with the drive assembly, relative to the cartridge so that the at least one piercing element protrudes to a first length from a forward end of the cartridge; and subsequently longitudinally displacing the at least one piercing element relative to the cartridge in an incremental manner, so that during at least one of the subsequent displacements of the at least one piercing element relative to the cartridge, the at least one piercing element protrudes from a forward end of the cartridge to a second length, whereas the second length is greater than the first length.

Preferably, the at least one piercing element is displaced relative to the cartridge in such manner that with each displacement the at least one piercing element protrudes from a forward end of the cartridge to a greater longitudinal extent, such that at least the first length corresponds to a deposition area disposed superficially to the nociceptors in the skin of the patient prior to reaching a pre-defined length that corresponds to a deposition area in the skin of the patient that is disposed at the level of the nociceptors in the skin or deeper thereof.

Further preferably, the magnitude of the increments of the longitudinal displacement of the at least one piercing element relative to the forward end of the cartridge is dictated by the user during mode selection procedure, whereby the user anticipates the depth of the nociceptors in the skin of the patient.

Still further preferably, following the first displacement of the at least one piercing element, the automated algorithm initiates a sequence of reciprocations and incremental linear advancements of the at least one piercing element such that local anesthesia, which is disposed within the cartridge is deposited into the skin of the patient at progressively increasing depths until a desired final depth has been reached.

BRIEF DESCRIPTION OF THE DRAWINGS

The present invention will be understood and appreciated more fully from the following detailed description, taken in conjunction with the drawings in which:

FIGS. 3A-3C are simplified respective pictorial and two different elevation illustrations of a base unit, forming part of the MPAI of FIGS. 1A & 1B;

FIG. 15A-15D are a simplified flow chart illustrating the usage of the MPAI of FIGS. 1A-14B;

FIGS. 16A-16D are a simplified diagram illustrating the usage of the MPAI in several operative orientations, as specifically illustrated in FIGS. 10A-12B;

DETAILED DESCRIPTION OF EMBODIMENTS

Figure 1A:
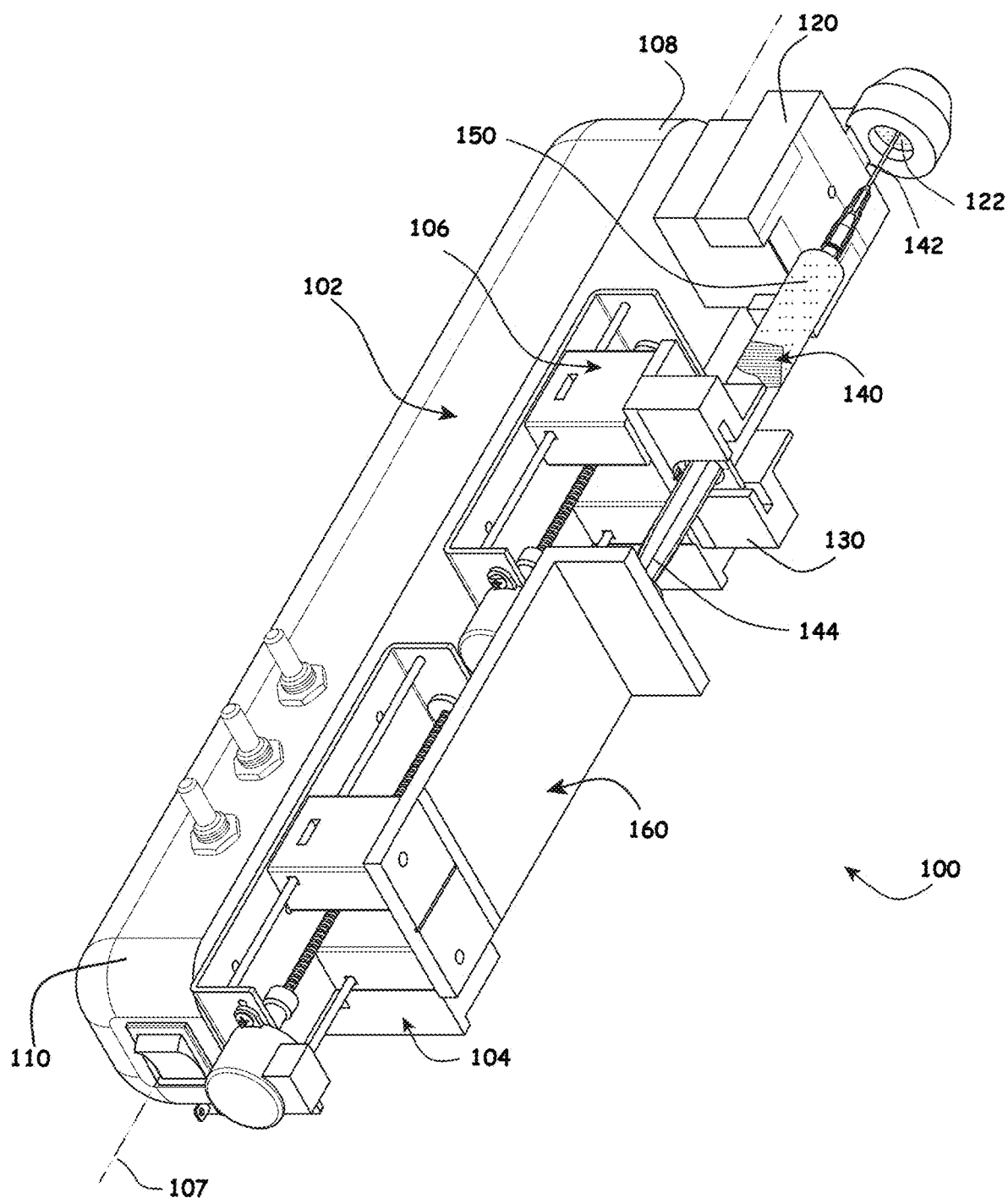
FIGS. 1A & 1B are two different simplified pictorial illustrations of a multi-purpose automatic injector (MPAI) constructed and operative in accordance with an embodiment of the invention.
Figure 1B:
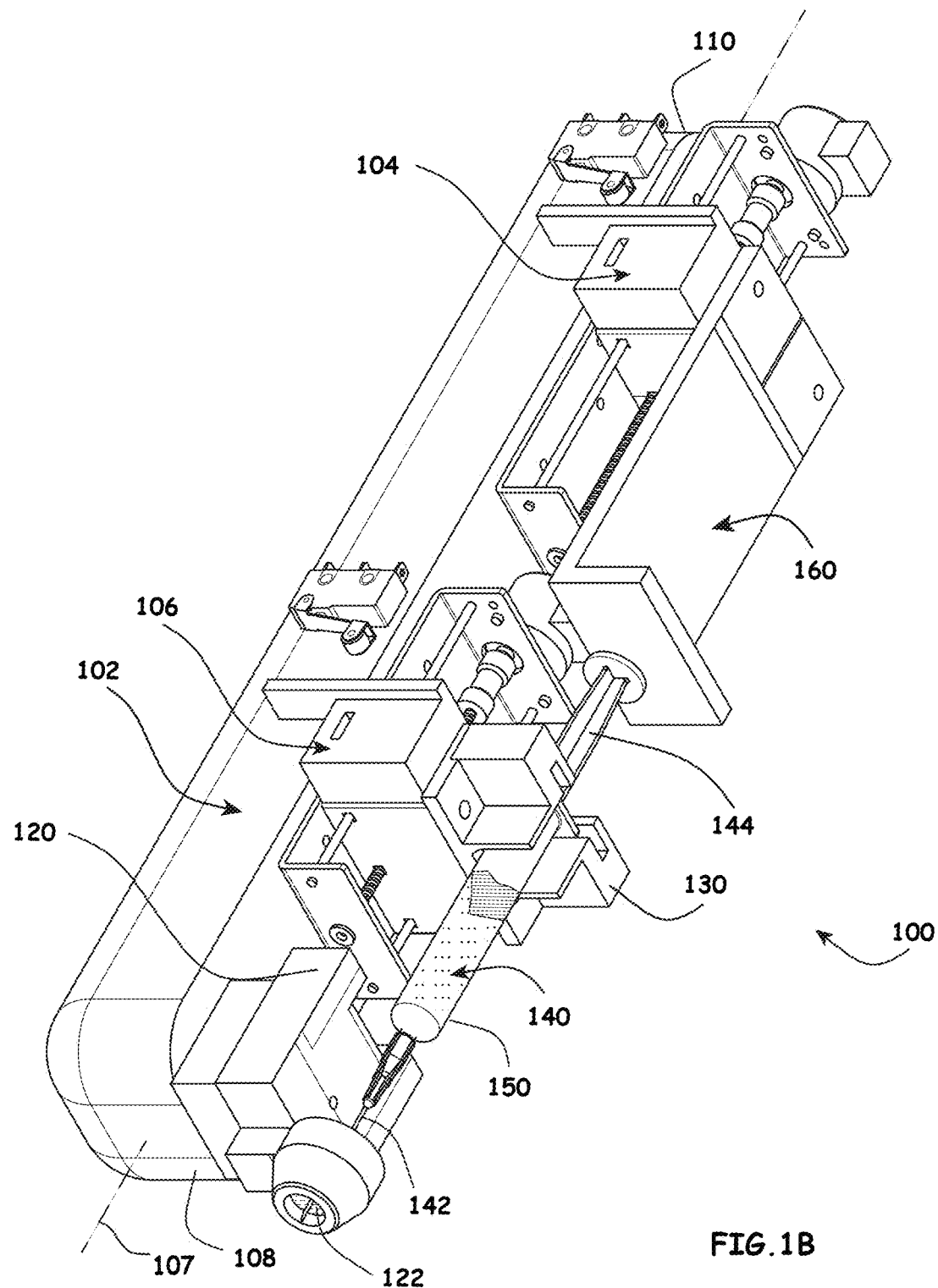
Figure 2A:
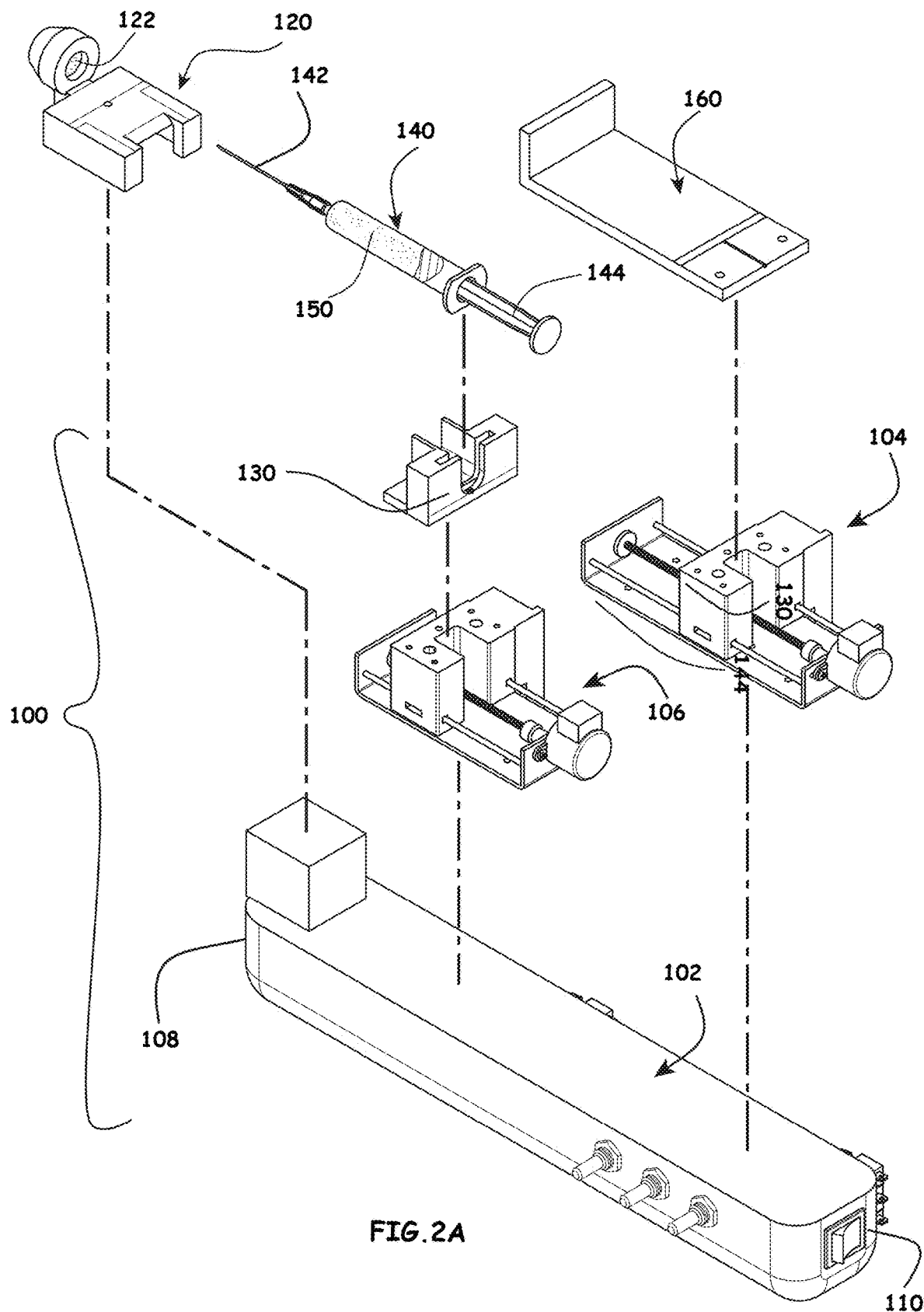
FIGS. 2A & 2B are two different simplified exploded view illustrations of the MPAI of FIGS. 1A & 1B.
Figure 2B:
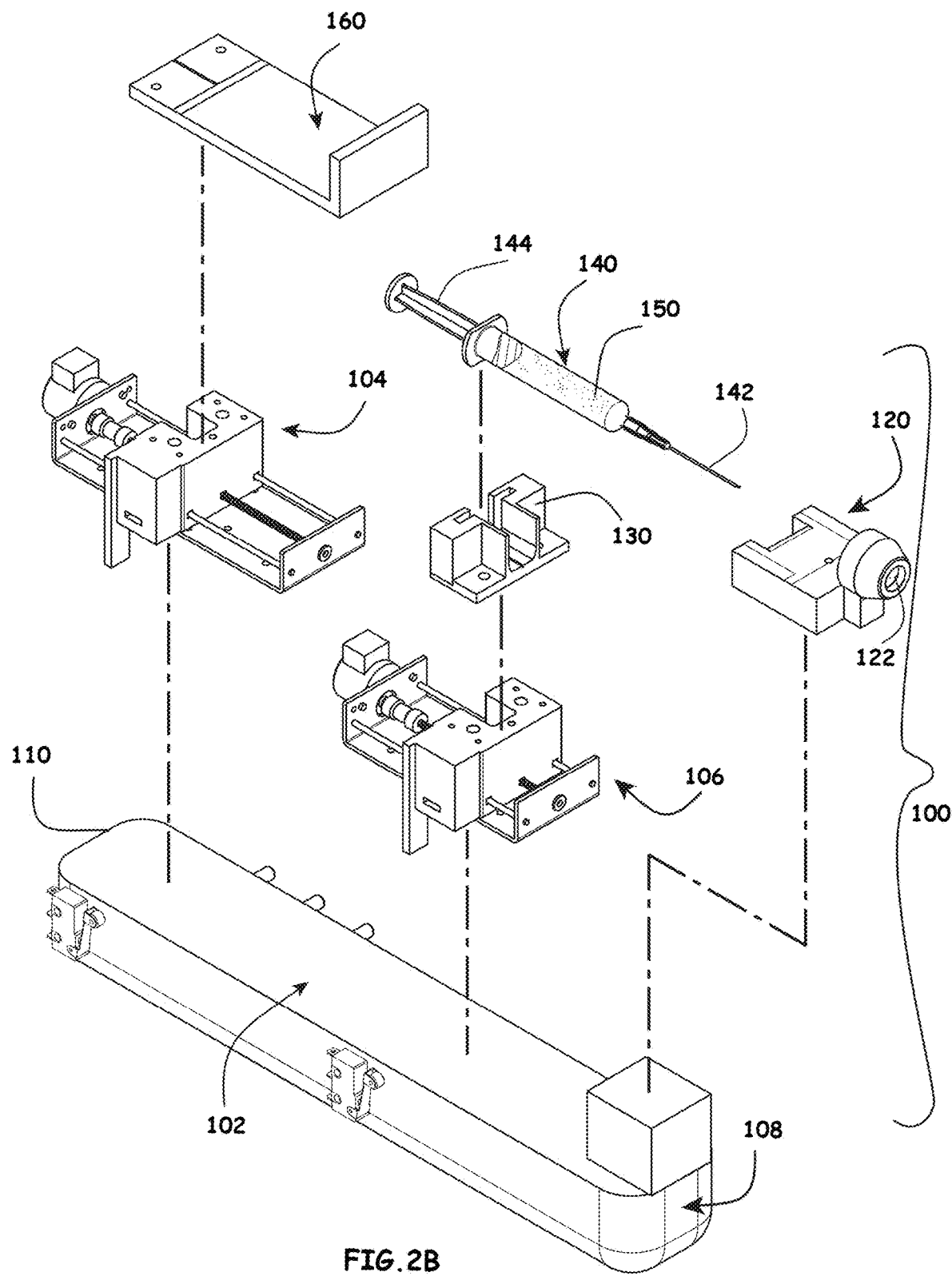

Reference is now made to FIGS. 1A & 1B, which are two different simplified pictorial illustrations of a multi-purpose automatic injector (MPAI) constructed and operative in accordance with an embodiment of the invention and to FIGS. 2A & 2B, which are two different simplified exploded view illustrations of the MPAI of FIGS. 1A & 1B.

A multi-purpose automatic injector (MPAI) is provided in accordance with an embodiment of the present invention, which is preferably used both for depositing a medicament into the skin of a patient via reciprocating motion of a needle and for injection of a medicament contained in a syringe, which is coupled to the MPAI.

It is noted that deposition of medicament into the skin is achieved by mechanical pushing as the needle penetrates the skin as well as negative pressure induced when the needle is withdrawn from the skin during the reciprocating motion thereof. Withdrawal of the needle from the skin creates negative pressure within the tubular "cavities" created by needle penetration that draws additional medicament into the substance of the skin. Thus, repetitive penetration and withdrawal of the needle leads to an accumulating volume of the medicament being deposited into the skin.

As seen in FIGS. 1A-2B, an MPAI 100 in accordance with one embodiment of the present invention comprises a base unit 102, which contains various electronic components that are utilized for operation and control of the MPAI 100, as described in detail hereinbelow. The base unit 102 serves as support for preferably two carriage assemblies 104 and 106, which are fixedly attached thereto. It is noted that the base unit 102 is arranged along a longitudinal axis 107 and having a forward end 108 and a rearward end 110.

The first carriage assembly 104 is preferably fixedly attached to the base unit 102 adjacent the rearward end 110 thereof. The second carriage assembly 106 is preferably fixedly attached to the base unit 102 approximately at an intermediate location along the longitudinal extent thereof and is forwardly spaced from the first carriage assembly 104.

A cartridge 120 is preferably fixedly attached adjacent the forward end 108 of the base unit 102, and preferably a portion of the cartridge 120 protrudes forwardly from the forward end 108 of the base unit 102. It is a particular feature of an embodiment of the present invention that a medicament 122 is preferably contained within a portion of the cartridge 120.

As seen in FIGS. 1A & 1B, a syringe holder element 130 is preferably coupled with a portion of the second carriage assembly 106. The syringe holder element 130 is adapted to support a syringe 140. It is noted that a needle 142 is attached or integrally formed with the forward end of the syringe 140 and a plunger rod 144 is slidably inserted through the rearward end of the syringe 140 and adapted to conceal a first medicament 150 within the inner volume of the syringe 140.

It is noted that the needle 142 in accordance with an embodiment of the present invention is a standard hollow-bore hypodermic needle. Alternatively, the needle-syringe complex may be replaced by any of the following: a vacuum collection tube connected to a blood collection needle such that the overall function of the device becomes to introduce a blood collection needle in a painless manner into the lumen of a vein or artery with subsequent withdrawal of a blood sample by means of the vacuum collection tube pneumatically linked to the needle; an intravascular catheter such as an intravenous or arterial catheter such that the overall function of the device becomes to introduce an intravascular catheter in a painless manner into the lumen of a vein or artery; a finger-stick lancet such that the overall function of the device becomes to introduce a finger-stick lancet into the tissues in a painless manner; a piercing needle such that the overall function of the device becomes to introduce a piercing needle into the tissues in a painless manner or any other instrument that penetrates a patient's tissue, such as for example a rotary tool with an abrading bit installed therein, which is configured to abrade the tissues in a painless manner.

It is a particular feature of an embodiment of the present invention that the needle 142 partially protrudes forwardly from the second carriage assembly 106 and is preferably at least partially received within a portion of the cartridge 120 which contains medicament 122.

It is a further particular feature of an embodiment of the present invention that the syringe 140 is configured to be displaced relative to the base unit 102 and relative to the cartridge 120 upon receipt of an appropriate signal from a computerized controller of the MPAI 100.

It is further seen in FIGS. 1A & 1B that a plunger driver 160 is coupled with a portion of the first carriage assembly 104.

It is a particular feature of an embodiment of the present invention that the plunger driver 160 is disposed rearwardly of the plunger rod 144 and is configured to displace the plunger rod 144 relative to the syringe 140 upon receipt of an appropriate signal from the computerized controller of the MPAI 100 to effect ejection of the medicament 150 from the syringe 140 through needle 142.

Figure 3A:
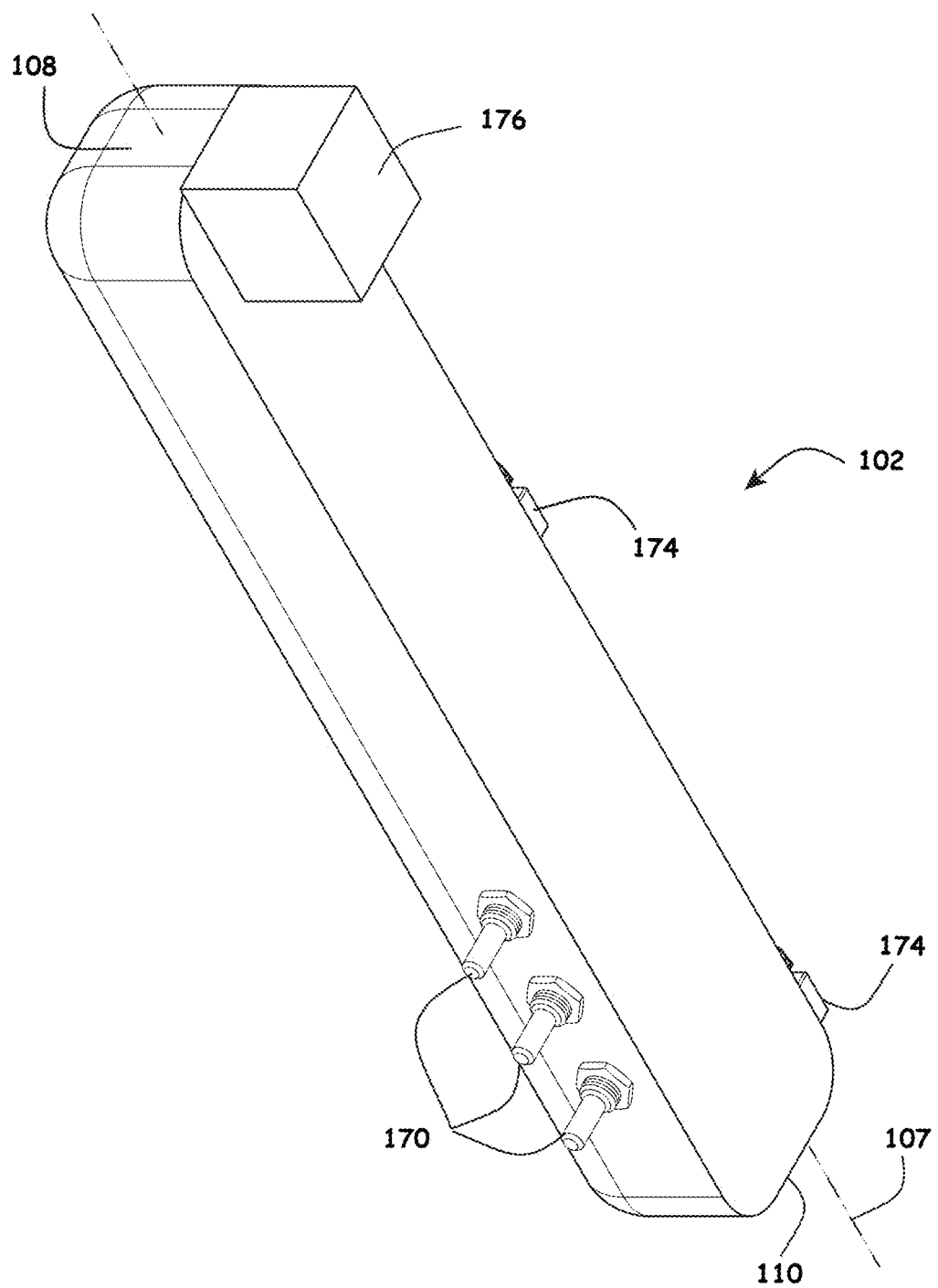

Reference is now made to FIGS. 3A-3C, which are simplified respective pictorial and two different elevation illustrations of the base unit 102, forming part of the MPAI 100 of FIGS. 1A & 1B.

It is seen in FIGS. 3A-3C that the base unit 102 preferably includes a plurality of user input elements 170 typically located on one side wall thereof and an on/off switch 172 typically located on the rearward end 110 wall thereof. It is also seen specifically in FIG. 3B that typically two sensors 174 are located on another side wall thereof and are generally axially spaced from each other. A cartridge holder 176 may be disposed adjacent the forward end 108 of the base unit 102.

A computerized controller may be housed within the base unit 102 and configured to operate and control the MPAI 100, as described in detail hereinbelow.

Figure 4A:
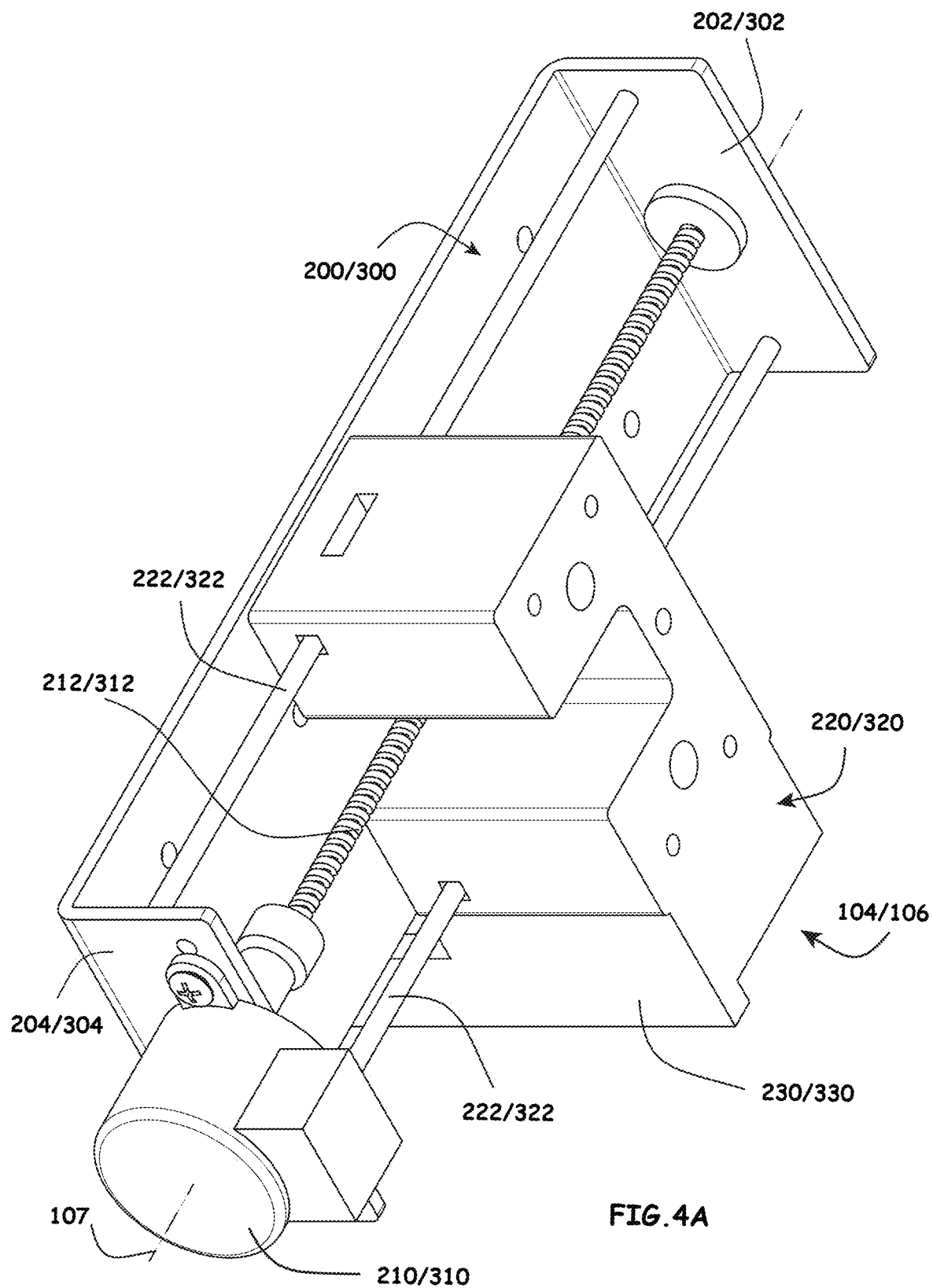
FIGS. 4A-4C are simplified respective pictorial and two different elevation illustrations of a carriage assembly, forming part of the MPAI of FIGS. 1A & 1B.
Figure 4C:
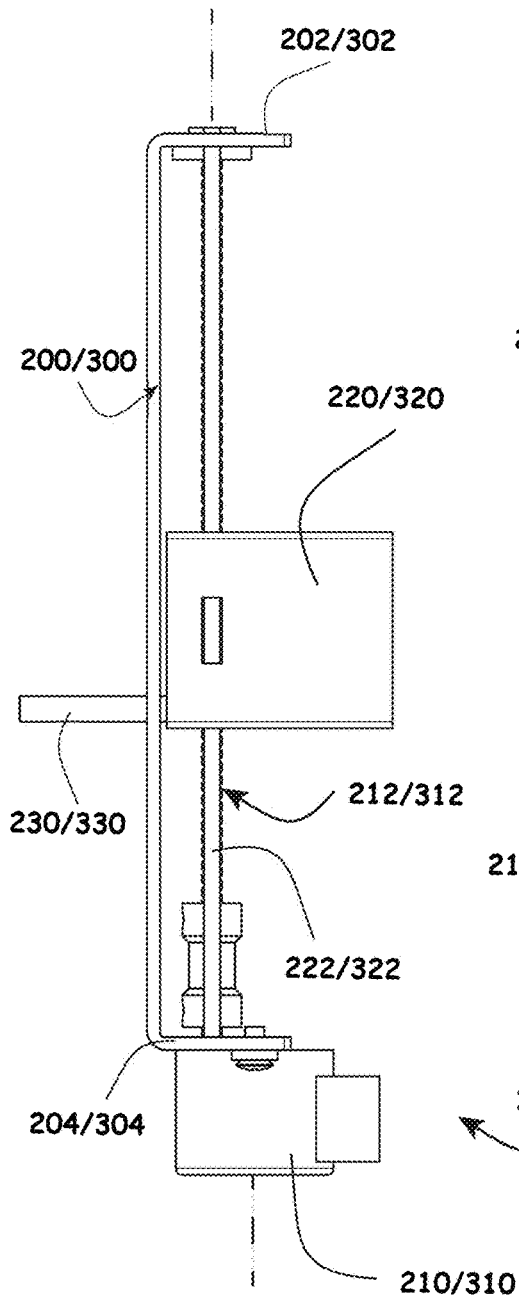
Figure 4B:
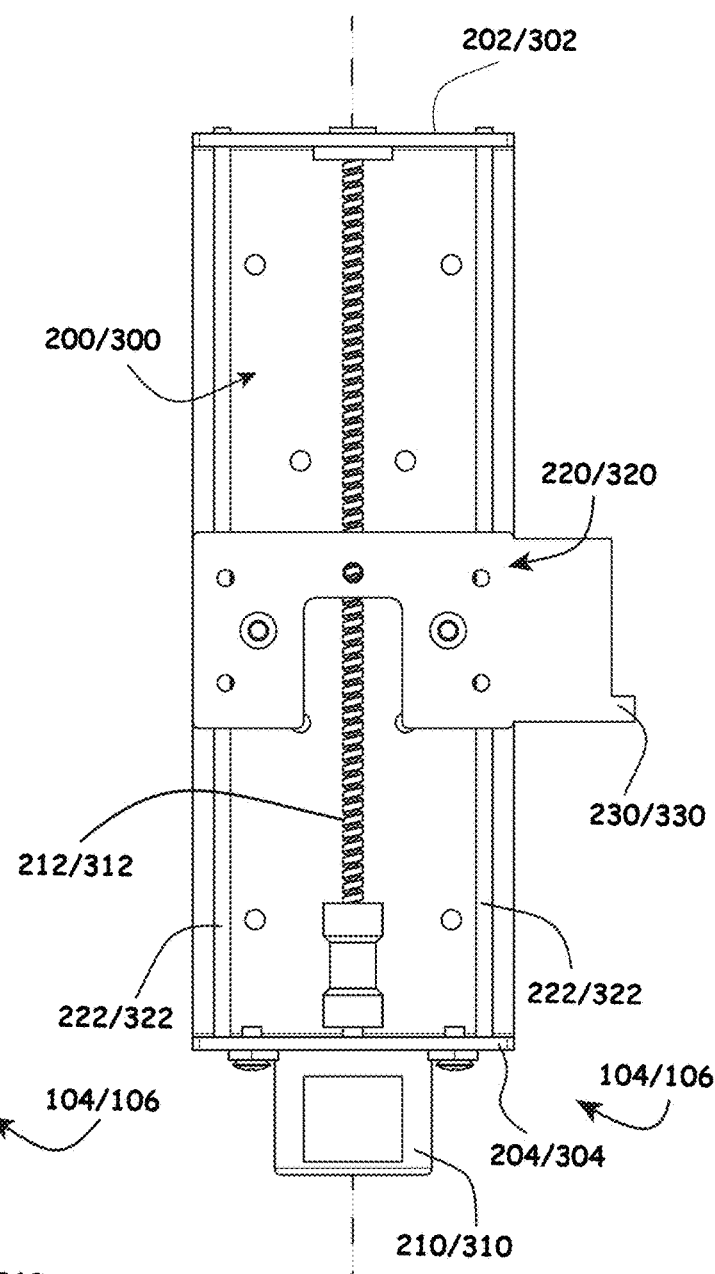

Reference is now made to FIGS. 4A-4C, which are simplified respective pictorial and two different elevation illustrations of the carriage assembly 104/106, forming part of the MPAI 100 of FIGS. 1A & 1B.

It is seen in FIGS. 4A-4C that the carriage assembly 104/106 preferably includes a support element 200/300 having a forward end 202/302 and a rearward end 204/304 and arranged along longitudinal axis 107. Preferably, an electrical motor 210/310 is fixedly mounted onto the support element 200/300 and a lead screw 212/312 is operatively coupled with the motor 210/310 and extends along the support element 200/300 from the rearward end 204/304 to the forward end 202/302 thereof.

Preferably, the lead screw 212/312 is inserted through a threaded bore formed in a driven element 220/320, thereby operatively connecting the motor 210/310 with the driven element 220/320. It is seen in FIGS. 4A-4C that torque exerted onto the lead screw 212/312 upon actuation of the motor 210/310, causes slidable displacement of the driven element 220/320 relative to the support element 200/300.

Typically, two guide pins 222/322 are inserted through the driven element 220/320 and extend longitudinally from the forward end 202/302 to the rearward end 204/304 of the support element 200/300, and are operative to guide and align the slidable displacement of the driven element 220/320 relative to the support element 200/300.

It is noted that the motors 210/310 may be any kind of programmable motors, such as stepper, encoded, brushless encoded, AC motor, which are operative for precisely displacing the driven elements 220/320 according to programmed algorithmic sequences.

The MPAI 100 includes a controller, which is operative for storing various programmed movement algorithms for the motors 210/310. Each one of the motors 210/310 has its own controller, which is adapted to interact with the MPAI controller for controlling operation of the motors 210/310 in accordance with the programmed algorithm.

It is seen in FIGS. 4A and 4C that an engagement wall 230/330 extends preferably downwardly from the driven element 220/320. The engagement wall 230/330 extends transversely with respect to the support element 200/300.

Figure 5:
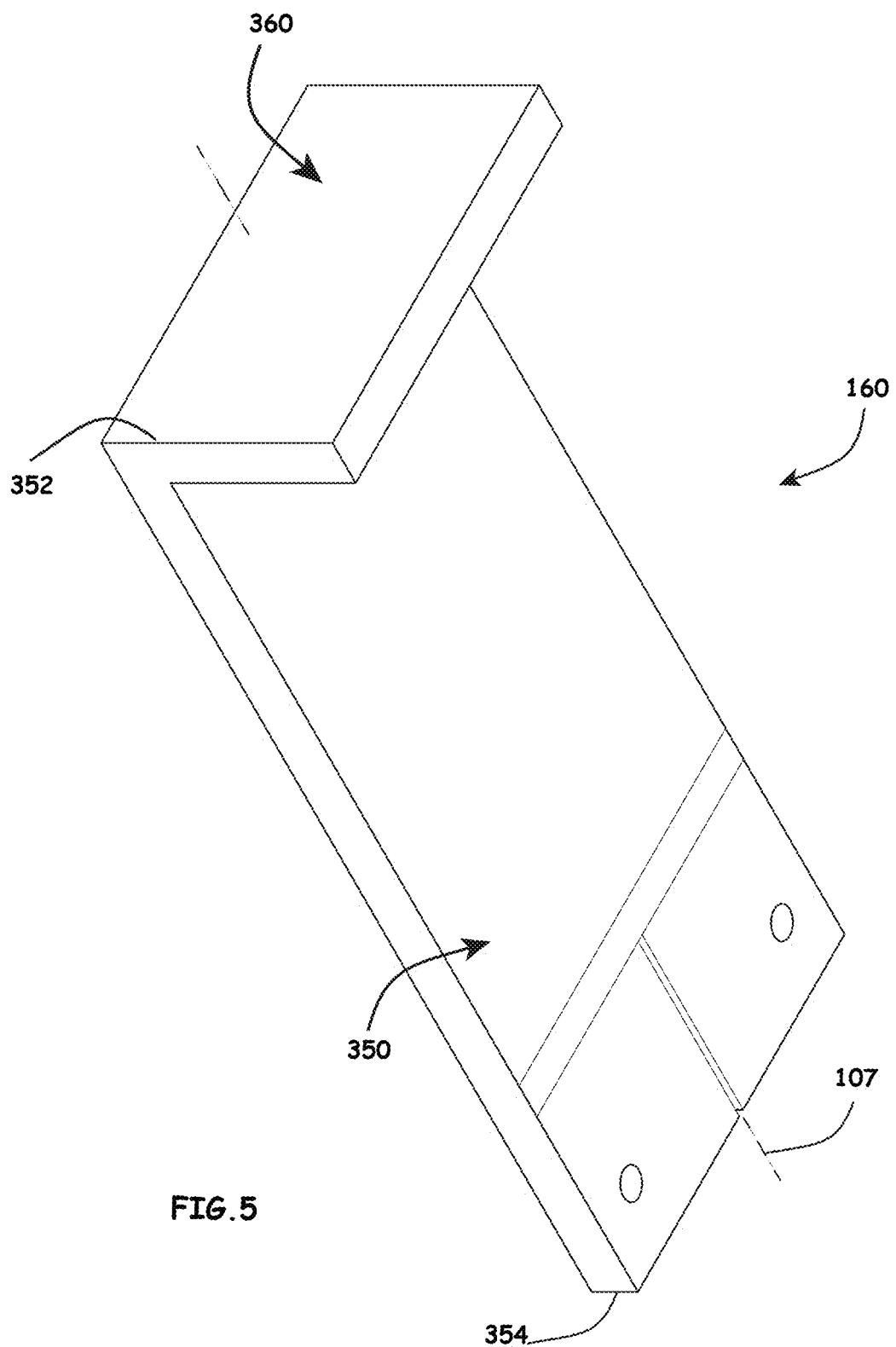
FIG. 5 is a simplified pictorial illustration of a plunger rod drive element, forming part of the MPAI of FIGS. 1A & 1B.

Reference is now made to FIG. 5, which is a simplified pictorial illustration of the plunger rod drive element 160, forming part of the MPAI 100 of FIGS. 1A & 1B.

It is seen in FIG. 5 that the plunger rod drive element 160 is preferably arranged along longitudinal axis 107 and has a base wall 350 with a forward end 352 and a rearward end 354 and plunger engaging wall 360, formed at the forward end 352 and generally extending transversely with respect to the base wall 350.

According to an embodiment of the present invention, the plunger rod drive element 160 is not connected to the plunger rod 144, rather only applies pressure to the plunger rod 144, in order to eject medicament 150 from the syringe 140.

Alternatively, the plunger rod drive element 160 is connected with the plunger rod 144, such that automated or manually-induced movement of the plunger rod driver element 160 is capable of effecting both positive and negative pressures within the syringe 140, thereby providing both injection and aspiration capabilities. Aspiration capabilities can be important when injecting some agents, such as local anesthesia and cosmetic filler products, for which aspiration is used to ensure a needle tip is not situated within a blood vessel in order to avoid intravascular injection of an agent contained within the syringe.

Further alternatively, both injection-only and injection-and-aspiration plunger rod drive elements can be employed by using a plunger rod drive element that is detachable from the MPAI 100, such that a different plunger rod drive element can be temporarily affixed thereto or allowing the user to perform manual injection or aspiration in the case that the plunger rod drive element is removed from the MPAI 100, and not replaced.

Figure 6:
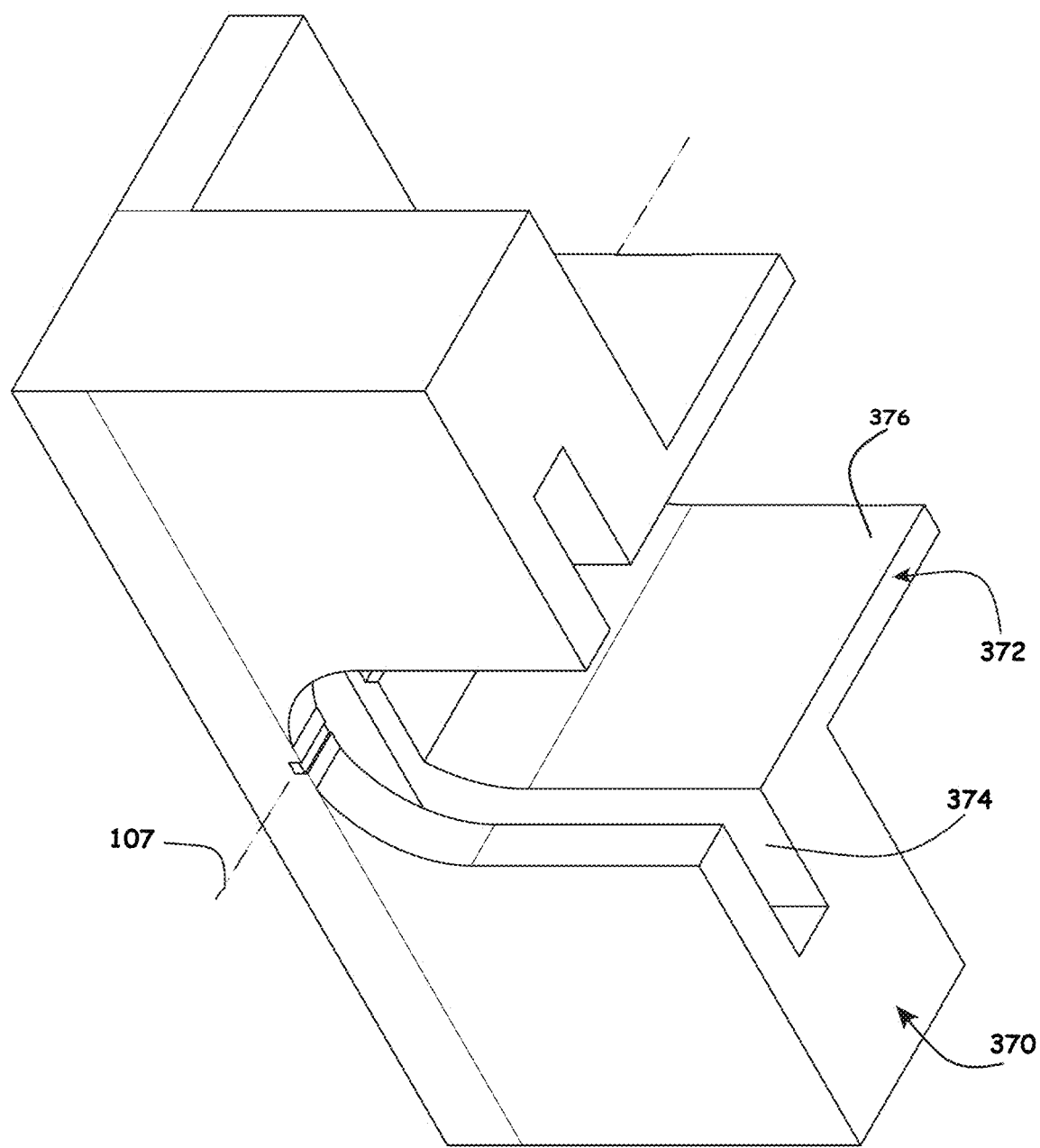
FIG. 6 is a simplified pictorial illustration of a syringe holder element, forming part of the MPAI of FIGS. 1A & 1B.

Reference is now made to FIG. 6, which is a simplified pictorial illustration of the syringe holder element 130, forming part of the MPAI 100 of FIGS. 1A & 1B.

It is seen in FIG. 6 that the syringe holder element 130 is preferably arranged along longitudinal axis 107 and has a base portion 370 and an extension portion 372 extending forwardly therefrom. The base portion 370 has a flange-like groove 374 formed therein and adapted to receive a flange of the syringe 140 thereinto. A semi-cylindrical opening 376 is preferably formed in the extension portion 372 and communicates with the groove 374.

It is noted that the syringe holder element 130 can alternatively be designed using any means for retaining the syringe 140 relative thereto. For example, any friction-fit systems, clamps, brackets, magnetic systems, chucks, set screws, resilient bands, hook and loop systems, and others. It is noted that in some embodiments, the syringe holder element 130 is detachable from the second carriage assembly 106 such that a different syringe holder element 130 can be attached in order to hold different sizes of syringes (e.g. 3 cc syringe, 5 cc, 10 cc, etc.).

Alternatively, the syringe holder element can be replaced by any of the following components: a component designed to hold a hypodermic needle that is not attached to a syringe; a component designed to hold a blood collection tube; a component designed to hold an intravenous catheter; a component designed to hold an arterial catheter; a component designed to hold a finger-stick lancet; a component designed to hold a piercing needle, or a component designed to hold any other instrument that penetrates a patient's tissue.

Figure 7A:
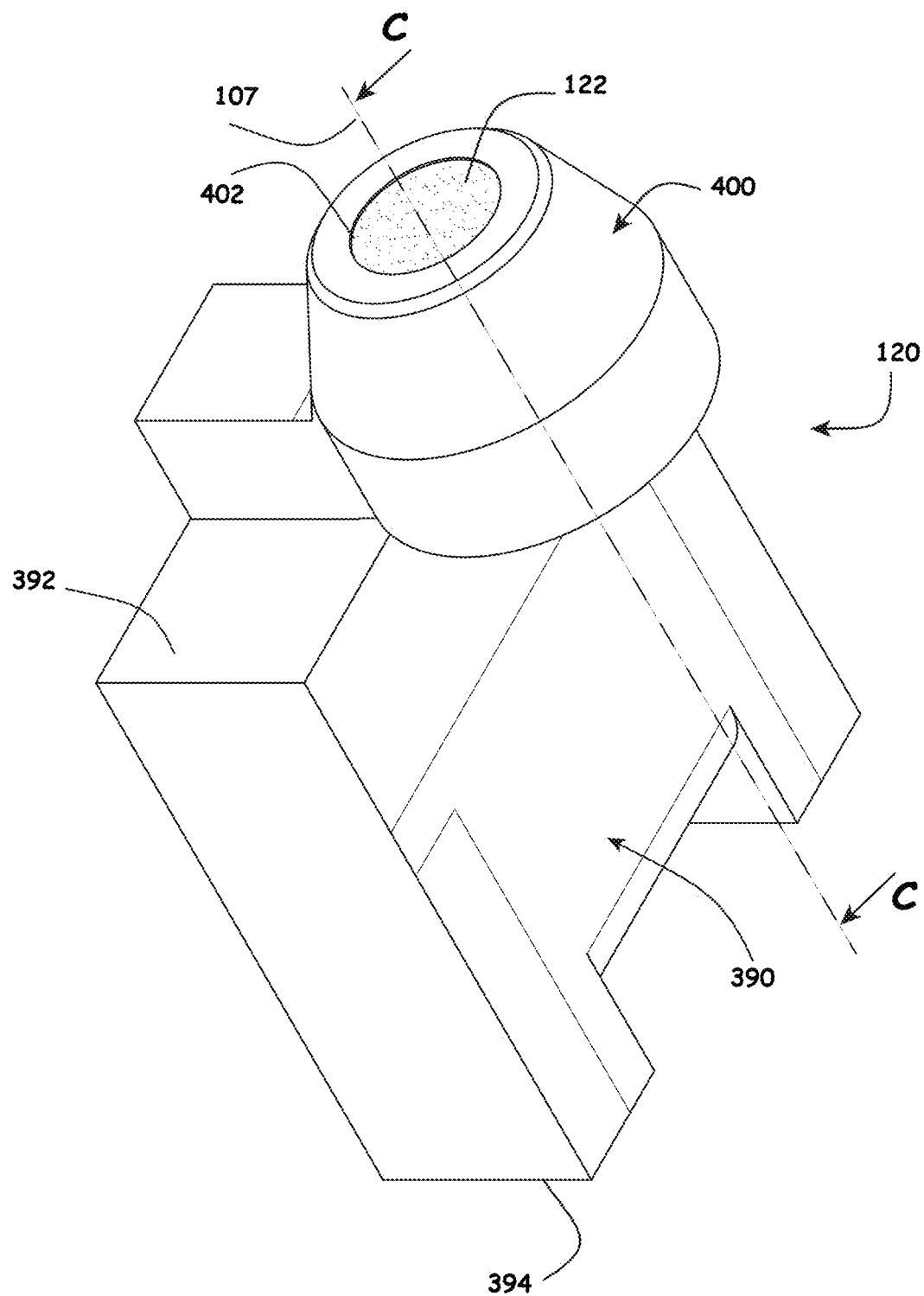
FIGS. 7A-7C are simplified respective two different pictorial illustrations and a sectional illustration of a cartridge forming part of the MPAI of FIGS. 1A & 1B, the cartridge is constructed and operative in accordance with a first embodiment of the invention, FIG. 7C being taken along lines C-C in FIG. 7A.
Figure 7B:
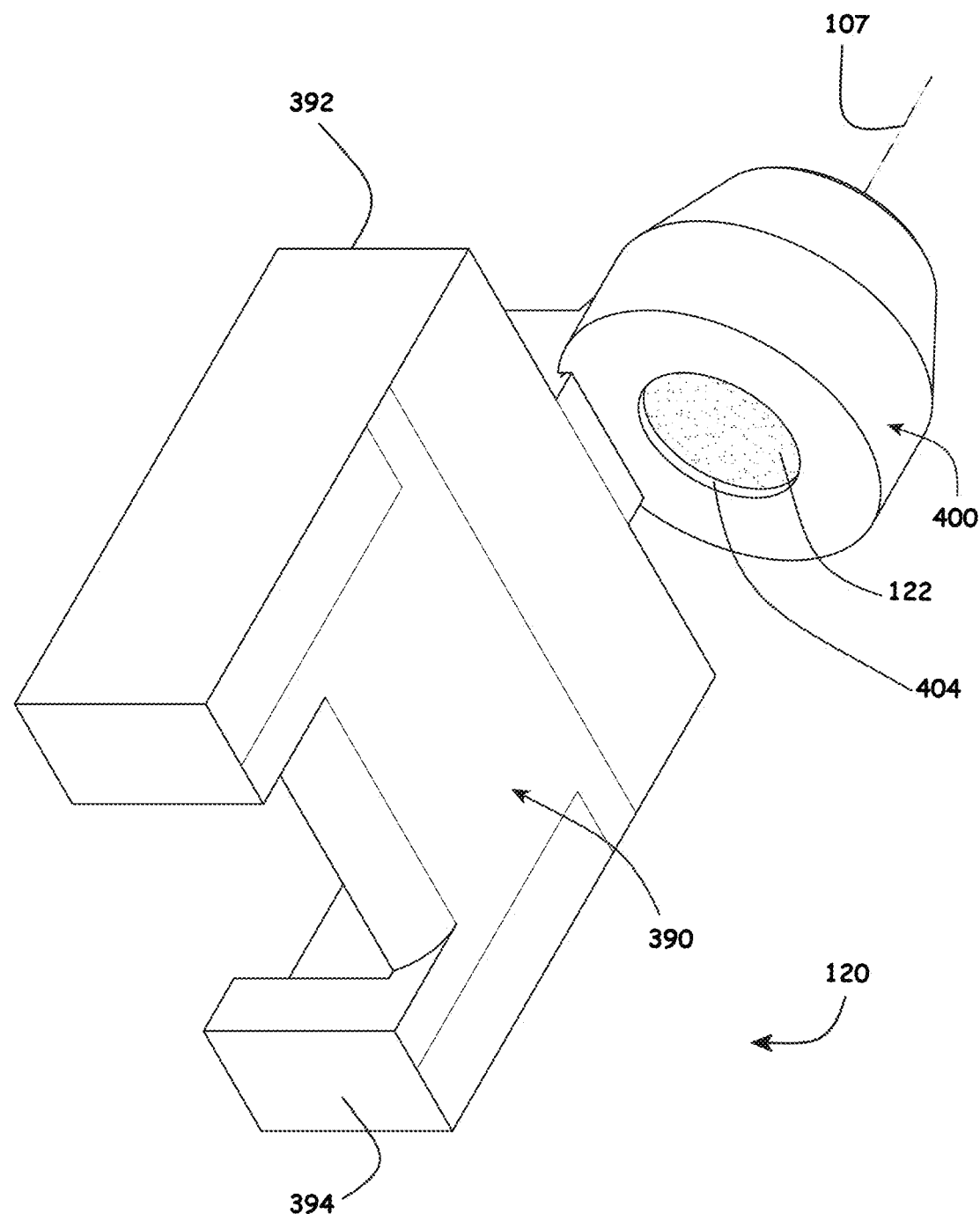
Figure 7C:
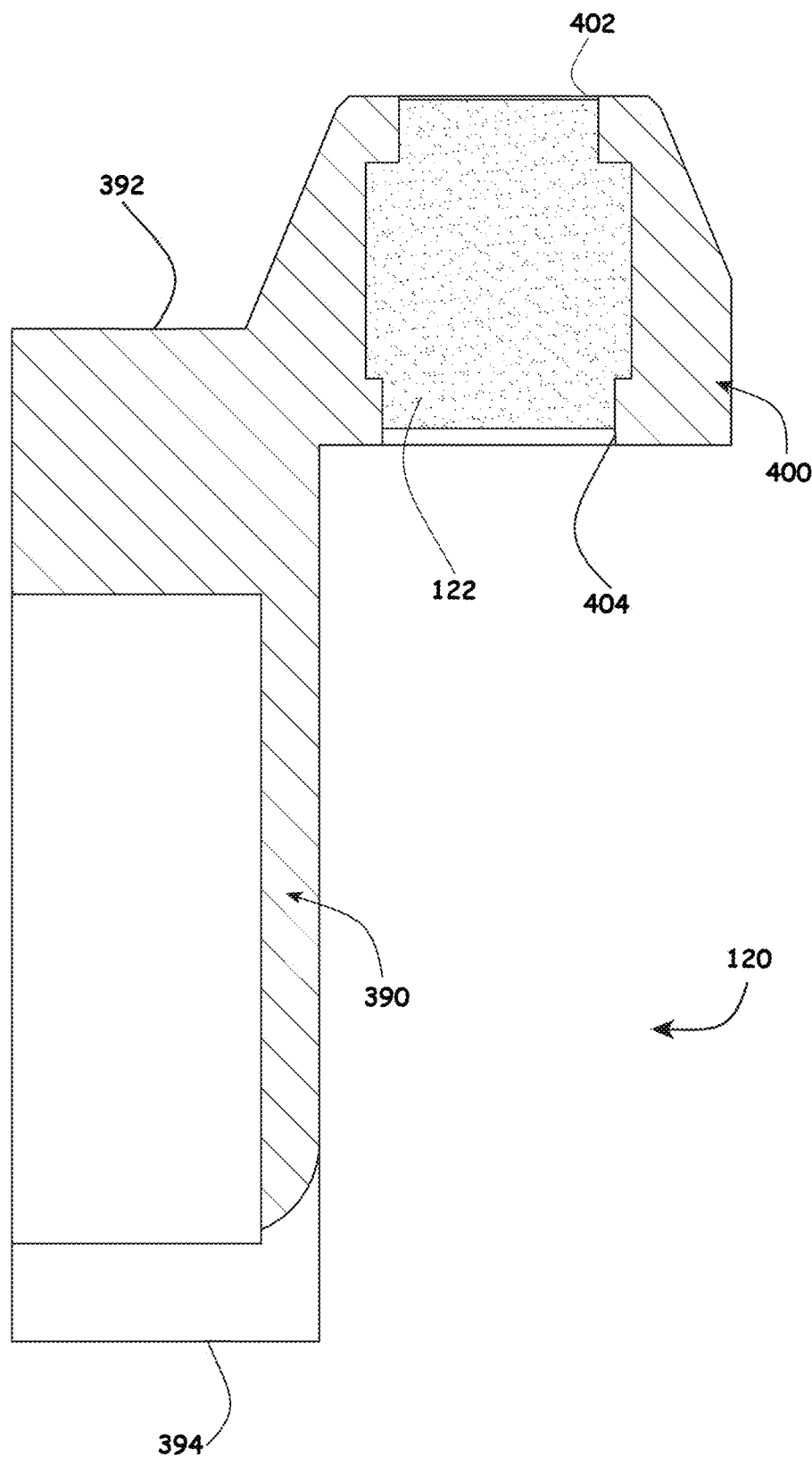

Reference is now made to FIGS. 7A-7C, which are simplified respective two different pictorial illustrations and a sectional illustration of the cartridge 120 forming part of the MPAI 100 of FIGS. 1A & 1B, the cartridge 120 is constructed and operative in accordance with a first embodiment of the invention, FIG. 7C being taken along lines C-C in FIG. 7A.

It is seen in FIGS. 7A-7C that the cartridge 120, in accordance with a first embodiment of the present invention, comprises a support element 390 having a forward end 392 and a rearward end 394 and a medicament reservoir 400 formed adjacent the forward end 392 and generally protruding axially forwardly therefrom.

It is a particular feature of an embodiment of the present invention that the medicament reservoir 400 has an inner volume adapted to contain medicament 122 therein. It is noted that the medicament 122 may be absorbed within a material, which is placed within the inner volume of the medicament reservoir 400. The medicament reservoir 400 preferably has a forward opening 402 and a rearward opening 404, preferably axially aligned therewith and spaced therefrom, both communicating with the inner volume of the medicament reservoir 400, where the medicament absorbed foam is placed.

In accordance with an embodiment of the present invention, the material can be any absorbent material, such as polyurethane or cellulose sponge, other fabrics or papers with are received into the medicament reservoir 400 and obstructs at least the opening 402 thereof. The absorbent material can be adhered to the internal surface of the medicament reservoir 400 by means such as glues and other adhesives. A reservoir of retained agent is preferably created in the absorbent material by means of applying a liquid agent such as injectable local anesthesia to the absorbent material, through which the needle 142 passes and retracts. Moreover, each time the needle 142 contacts and compresses the proximal edge of the absorbent material, the agent harbored in the absorbent material will exude onto the skin, further enhancing the volume of agent positioned for deposition into the skin.

It is a particular feature of an embodiment of the present invention that the absorbent material disposed within the medicament reservoir 400 of cartridge 120 provides for free-flowing liquid agent such as injectable LA, to remain within the reservoir cartridge 400 without significant spillage, and to maintain an interface of contact between the needle 142 and liquid agent during use, even against gravitational and other forces.

Figure 8A:
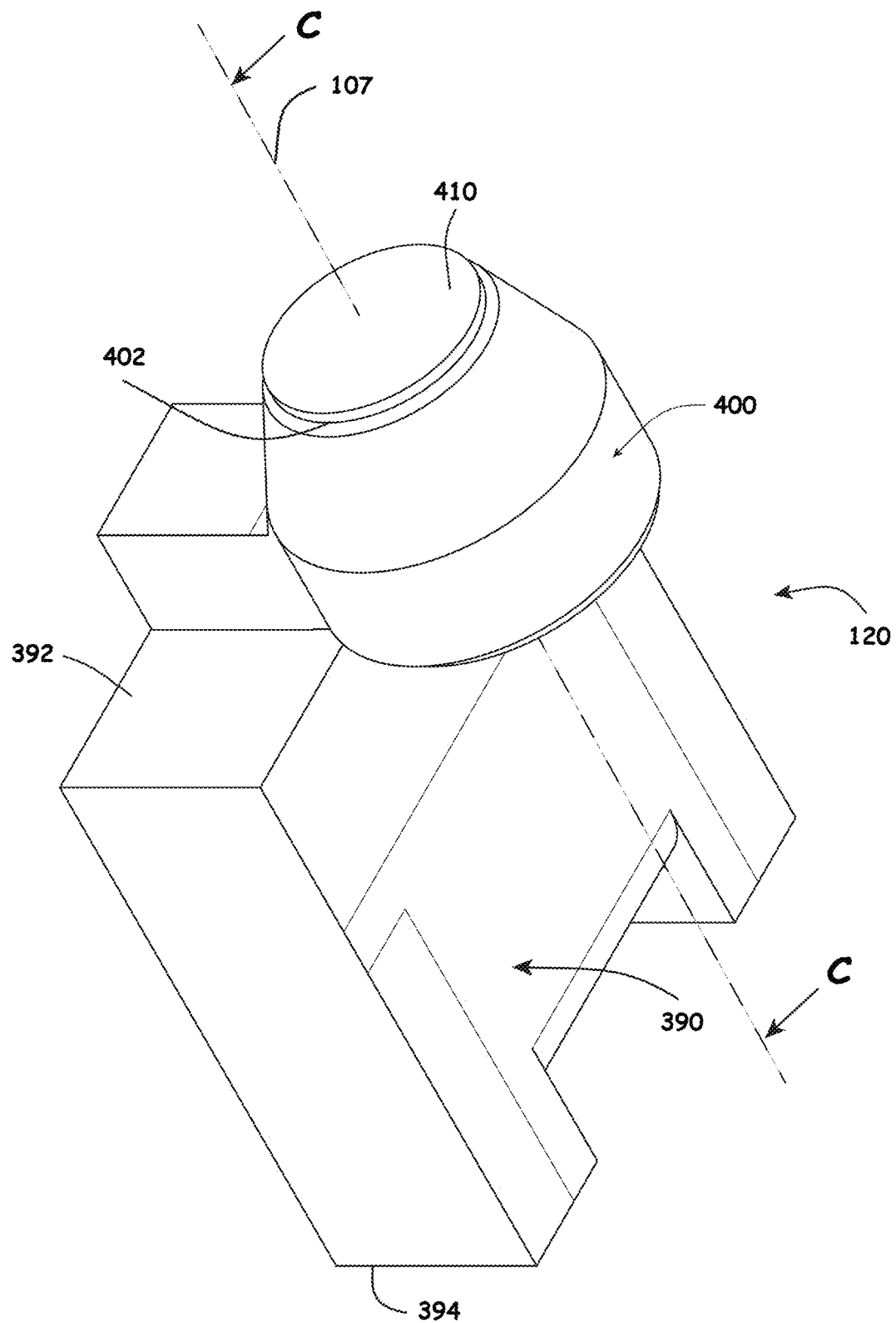
FIGS. 8A-8C are simplified respective two different pictorial illustrations and a sectional illustration of a cartridge forming part of the MPAI of FIGS. 1A & 1B, the cartridge is constructed and operative in accordance with a second embodiment of the invention, FIG. 8C being taken along lines C-C in FIG. 8A.
Figure 8B:
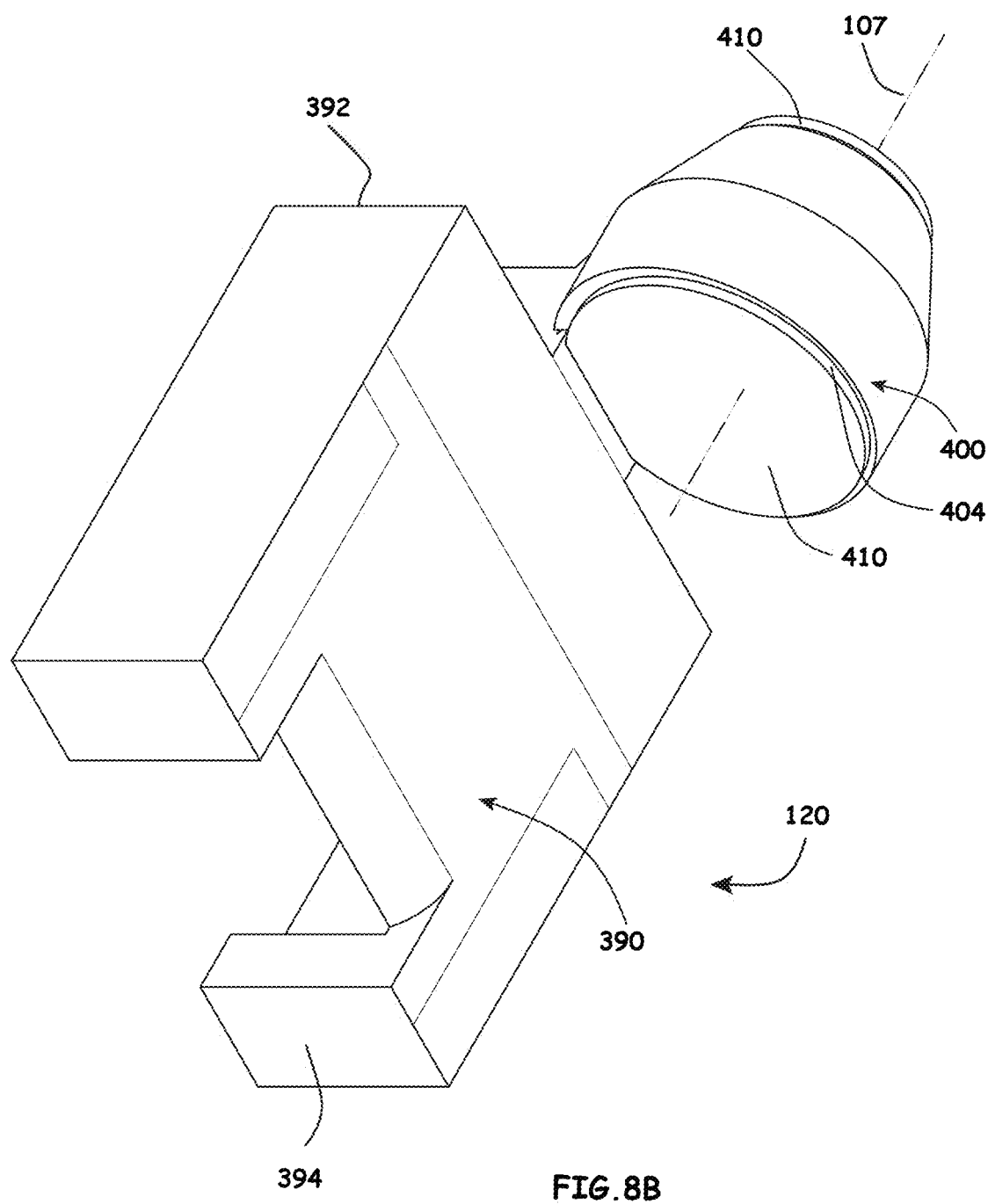
Figure 8C:
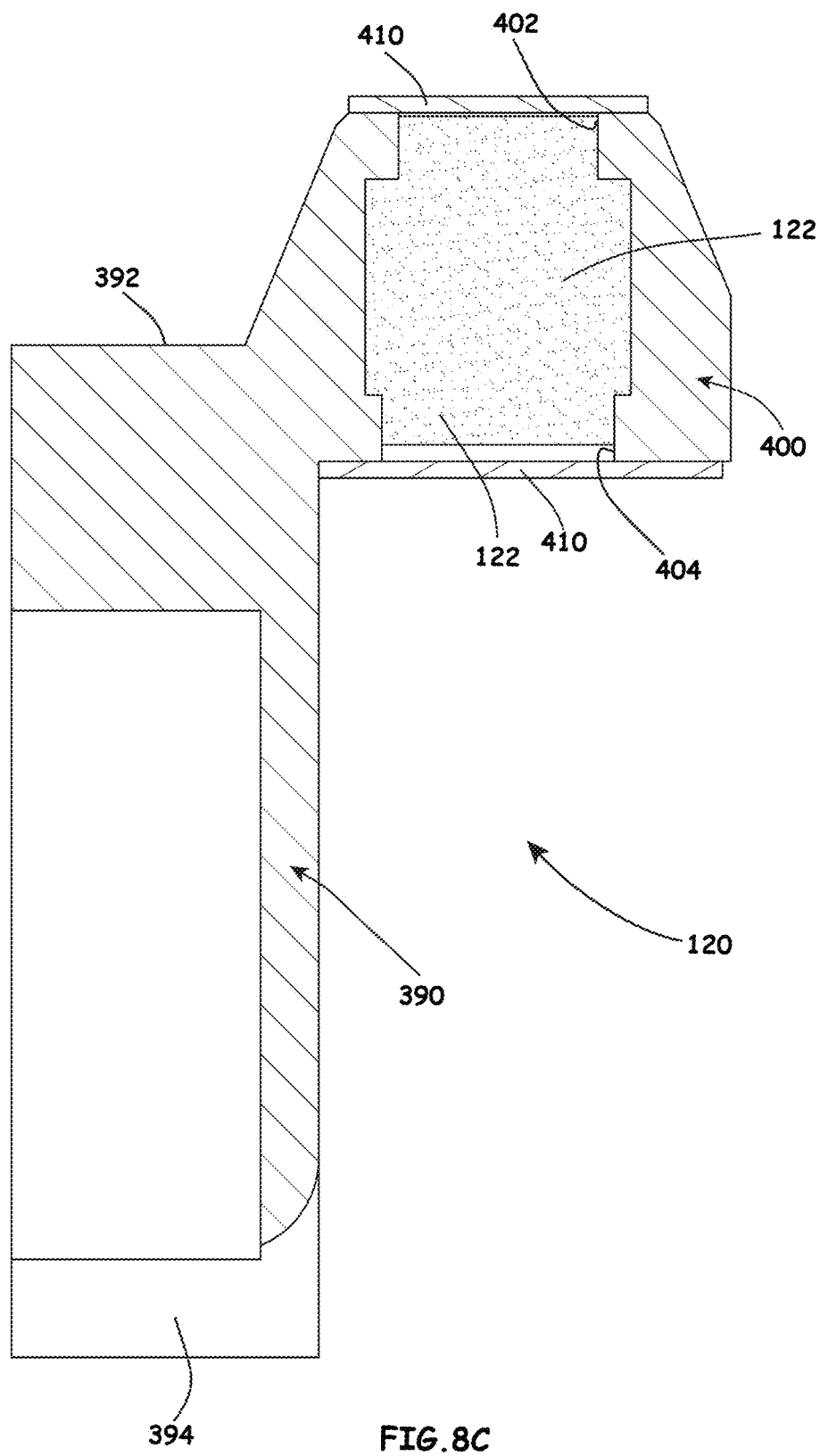

Reference is now made to FIGS. 8A-8C, which are simplified respective two different pictorial illustrations and a sectional illustration of the cartridge 120 forming part of the MPAI 100 of FIGS. 1A & 1B, the cartridge 120 is constructed and operative in accordance with a second embodiment of the invention, FIG. 8C being taken along lines C-C in FIG. 8A.

It is seen in FIGS. 8A-8C that the cartridge 120, in accordance with a second embodiment of the present invention, comprises a support element 390 having a forward end 392 and a rearward end 394 and a medicament reservoir 400 formed adjacent the forward end 392 and generally protruding axially forwardly therefrom. It is seen in FIGS. 8A-8C that the medicament reservoir 400 is generally disposed above the upper surface of the support element 390.

It is a particular feature of an embodiment of the present invention that the medicament reservoir 400 has an inner volume adapted to contain medicament 122 therein. It is noted that the medicament 122 may be in a form of liquid or alternatively may be absorbed within a material, which is placed within the inner volume of the medicament reservoir 400. The medicament reservoir 400 preferably has a forward opening 402 and a rearward opening 404, preferably axially aligned therewith and spaced therefrom, both communicating with the inner volume of the medicament reservoir 400, where the medicament absorbed foam is placed.

It is a further particular feature of an embodiment of the present invention that a fluid-impermeable seal element 410 is attached to both the forward opening 402 and the rearward opening 404 of the cartridge reservoir 400, such seal element 410 is adapted to protect the medicament 122 from contamination and prevent spillage thereof due to changes in the orientation of the MPAI 100.

It is noted that three such fluid-impermeable seal elements 410 may be used, one at each of the openings 402 and 404 of the medicament reservoir 400 and one situated between these two seal elements 410 so as to divide the medicament reservoir 400 into two, separated fluid-tight compartments into which different fluids can be stored prior to use including injectable local anesthesia in one compartment and a buffering solution in the other compartment.

Sealing elements 410 may be formed of silicone, rubber, gel, fabric, tape, paper etc. The sealing element 410 may be integrally formed with the medicament reservoir 400 or be an independent element that is attached to the medicament reservoir 400 by means of adhesives, friction-fit, and external compression force such as by an elastic ring placed around the sealing element 410 and the medicament reservoir 400.

It is noted that alternatively, both the absorbed material and the sealing elements 410 may be used together in accordance with an embodiment of the present invention.

It is a particular feature of an embodiment of the present invention that the forward end of the cartridge 120 may bear a transferable ink, dye, paint or other material on its surface such that application of the forward end of the cartridge 120 to the patient's skin transfers the ink/dye onto the skin, thereby creating a reference demarcation. In case that the cartridge 120 is intentionally or unintentionally moved from its intended location of placement onto the patient's skin, the demarcation left on the skin can be used to replace the forward end of the cartridge 120 onto the skin in essentially the same location as the original placement, thereby ensuring that an interrupted reciprocation sequence of the needle 142 through the cartridge 120 can be continued with the needle 142 penetrating the original skin location that has already been partially anesthetized prior to the movement of the cartridge 120.

Alternatively, an adhesive such as a glue, segment of adhesive tape, or other may be applied to the forward end of the cartridge 120 so as to create temporary adhesion between the patient's skin and the forward end of the cartridge 120 in order to minimize the chance of cartridge movement relative to the patient's skin during use of the device.

It is noted that the cartridge 120 may be of various shapes and may include a C-clamp mechanism, which is incorporated at the forward end of the cartridge 120, similar to the design of a piercing tool. The rearward jaw of the C-clamp serves as the face of the cartridge 120 through which the needle 142 reciprocates, the forward jaw of the C-clamp is oriented generally parallel to the rearward jaw. The longitudinal clearance between the two jaws is preferably adjustable to allow for clamping of body areas such as fingers, and earlobes of varying dimensions.

Figure 9A:
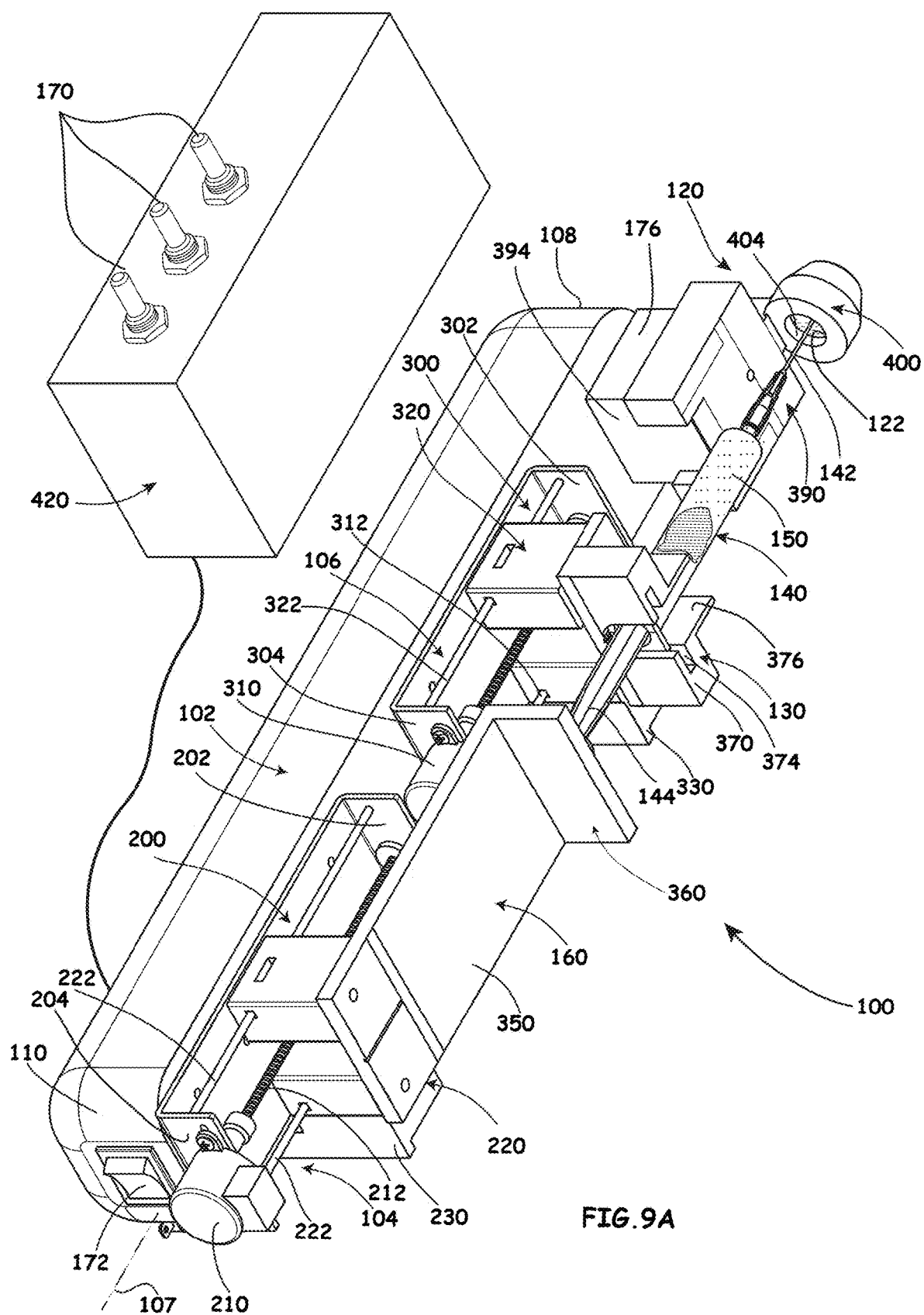
FIGS. 9A & 9B are two different simplified pictorial illustrations of a corded assembled MPAI, constructed and operative in accordance with an embodiment of the invention.
Figure 9B:
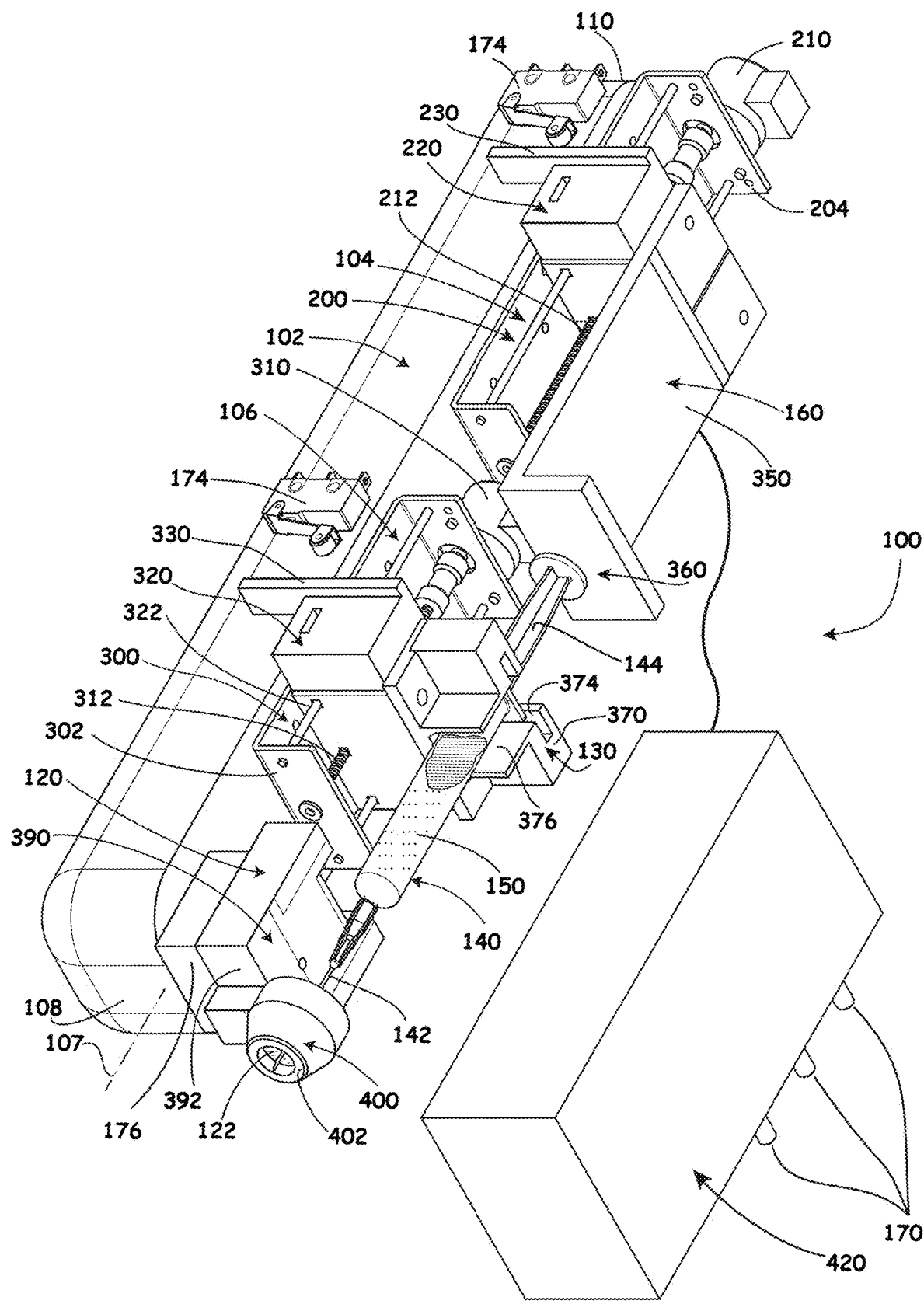

Reference is now made to FIGS. 9A & 9B, which are two different simplified pictorial illustrations of a corded assembled MPAI 100, constructed and operative in accordance with an embodiment of the invention.

It is seen in FIGS. 9A & 9B that in accordance with an embodiment of the present invention the base unit 102 is configured to be in a wired connection with an external electronic unit 420, which contains various electronic components therewithin that are configured to operate and control the MPAI 100.

It is specifically seen in FIGS. 9A & 9B that the first carriage assembly 104 is fixedly attached onto the base unit 102, adjacent the rearward end 110 thereof. The first driven element 220 is adapted to be axially displaceable relative to the first support element 200 of the first carriage assembly 104 and thus relative to the base unit 102 upon actuation of the first electrical motor 210.

The plunger driver 160 is preferably fixedly attached to the first driven element 220, therefore configured to be displaced axially along with the first driven element 220 upon actuation of the first motor 210.

It is also specifically seen in FIGS. 9A & 9B that the second carriage assembly 106 is fixedly attached onto the base unit 102, generally at an intermediate location thereof. The second support element 300 of the second carriage assembly 106 is disposed such that its rearward end 304 is generally axially forwardly spaced from the forward end 202 of the first support element 200 of the first carriage assembly 104.

The second driven element 320 is adapted to be axially displaceable relative to the second support element 300 of the second carriage assembly 106 and thus relative to the base unit 102 upon actuation of the second electrical motor 310.

The syringe holder element 130 is preferably fixedly attached to the second driven element 320, therefore configured to be displaced axially along with the second driven element 320 upon actuation of the second motor 310.

The syringe 140 is at least partially received within the syringe holder element 130, such that a portion of the syringe barrel is received within opening 376 and the flange of the syringe 140 is fixedly retained within groove 374 of the syringe holder element 130.

It is a particular feature of an embodiment of the present invention that the syringe 140 is fixedly attached to the second driven element 320 through the syringe holder element 130, and therefore displaceable together therewith.

The plunger rod 144 is partially inserted into the syringe barrel such that the rearward flange of the plunger rod 144 is generally forwardly spaced from the plunger engaging wall 360 of the plunger driver 160 in storage, before use of the MPAI 100.

It is specifically seen in FIGS. 9A & 9B that the cartridge 120 is fixedly attached to the cartridge holder 176 of the base unit 102 or to the base unit 102 directly, adjacent the forward end 108 thereof. The medicament reservoir 400 preferably protrudes forwardly from the forward end 108 of the base unit 102.

It is a particular feature of an embodiment of the present invention that the syringe 140 protrudes forwardly from the syringe holding element 130, such that the needle 142 thereof is configured to be received into the inner volume of the medicament reservoir 400 of cartridge 120 through opening 404 thereof.

It is seen in FIGS. 9A & 9B that in accordance with one embodiment of the present invention, the cartridge 120 as illustrated in FIGS. 7A-7C is used. Alternatively, the cartridge 120 as illustrated in FIGS. 8A-8C may alternatively be used, so that the needle 142 penetrates the seal element 410 covering opening 404 to be partially received within the inner volume of the medicament reservoir 400.

It is a further particular feature of an embodiment of the present invention, as specifically seen in FIG. 9B, that the first engagement wall 230 of the first driven element 220 is adapted to be engageable with switch 174 in order to provide indication of a particular position of the plunger driver 160 relative to the rearward flange of the plunger rod 144, namely a home position. Additionally, the second engagement wall 330 of the second driven element 320 is adapted to be engageable with switch 174 in order to provide indication of a particular position of the syringe holder element 130 relative to the medicament reservoir 400 of the cartridge 120, namely a home position.

It is noted that the switches 174 are particularly operative for providing an indication of when the first carriage assembly 104 or the second carriage assembly 106 returned to initial storage position. Alternatively, the switch 174 of the first carriage assembly 104 can be used for indicating completion of an aspiration process due to full rearward displacement of the plunger rod 144 relative to the syringe 104.

It is noted that the first driven element 230 is positioned at its home position in order to dispose the plunger driver 160 at a sufficiently rearward position so as to allow spatial clearance for the syringe 140 with a fully retracted plunger rod 144 to be inserted into the syringe holder element 130 without obstruction by the plunger driver 160.

It is further noted that the second driven element 330 is positioned at its home position to dispose the tip of the needle 142 entirely rearwardly of the medicament reservoir 400 in order to enable removal of the syringe 1740 from the MPAI 100.

In a usage sequence, the controller ensures that the plunger driver 160 and syringe holder element 130 are homed, using their respective limit switches 174, when the device is powered on. After completion of a reciprocation algorithm and associated insertion of the needle 142 to the desired depth, and optional ejection of the first medicament 150 from the syringe 140, homing of the plunger driver 160 is preferably repeated in order to allow clearance for subsequent homing of the syringe holder element 130 without interference by the plunger driver 160. Homing of the syringe holder element 130 withdraws the needle 142 from the medicament reservoir 400 completely, thereby allowing the syringe 140 to be removed from the MPAI 100. When both the plunger driver 160 and the syringe holder element 130 are homed, the MPAI 100 may be re-used.

It is specifically seen that according to this embodiment of the present invention where the MPAI 100 is connected to the external electronic unit 420 in a wired manner, the user input elements 170 can be positioned on the external electronic unit 420 and manipulated by the user thereon.

Figure 10A:
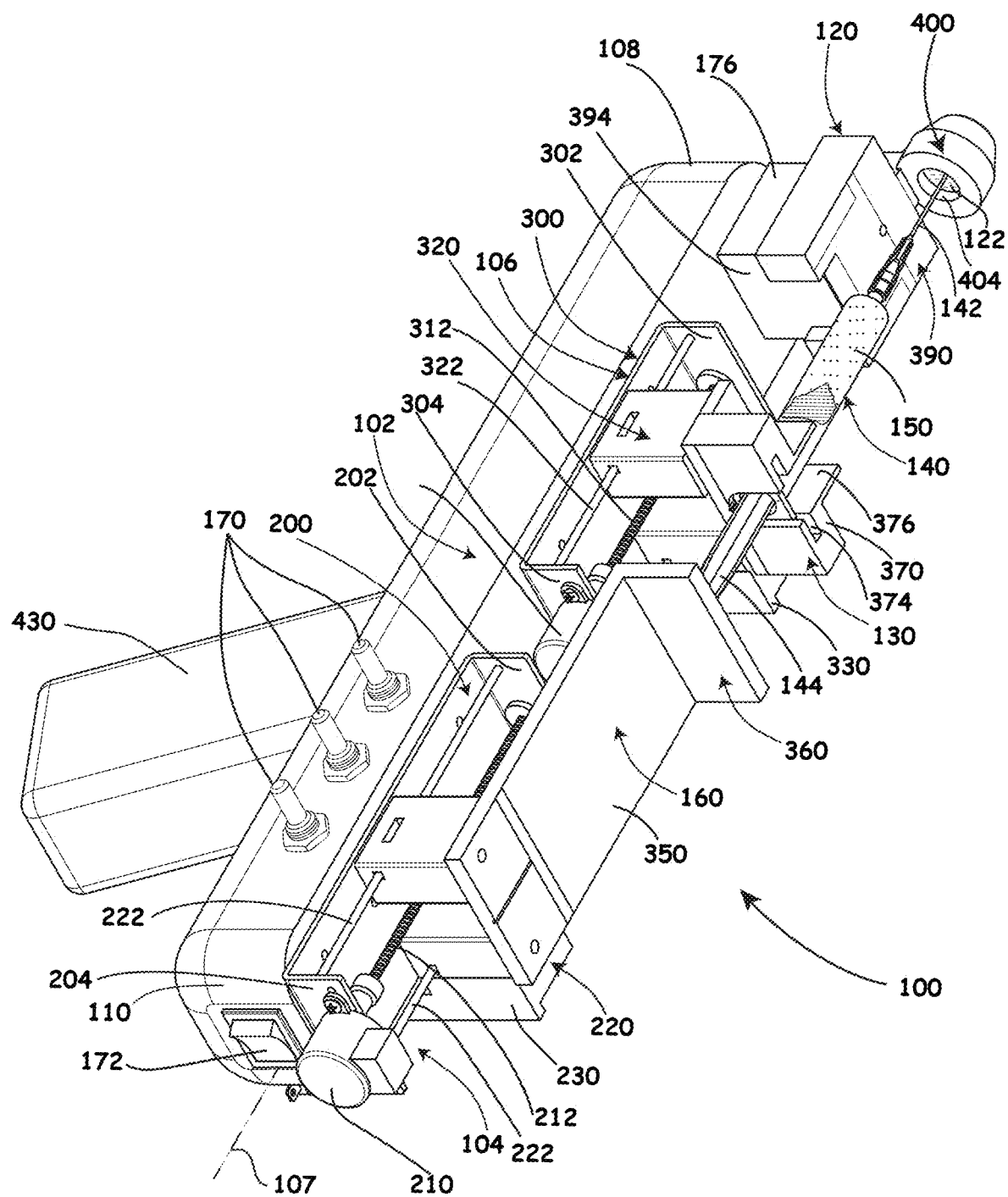
FIGS. 10A-10C are simplified respective two different pictorial illustrations and an elevation illustration of a handheld assembled MPAI having two motors, constructed and operative in accordance with an embodiment of the invention and showing the MPAI in a first operative orientation.
Figure 10B:
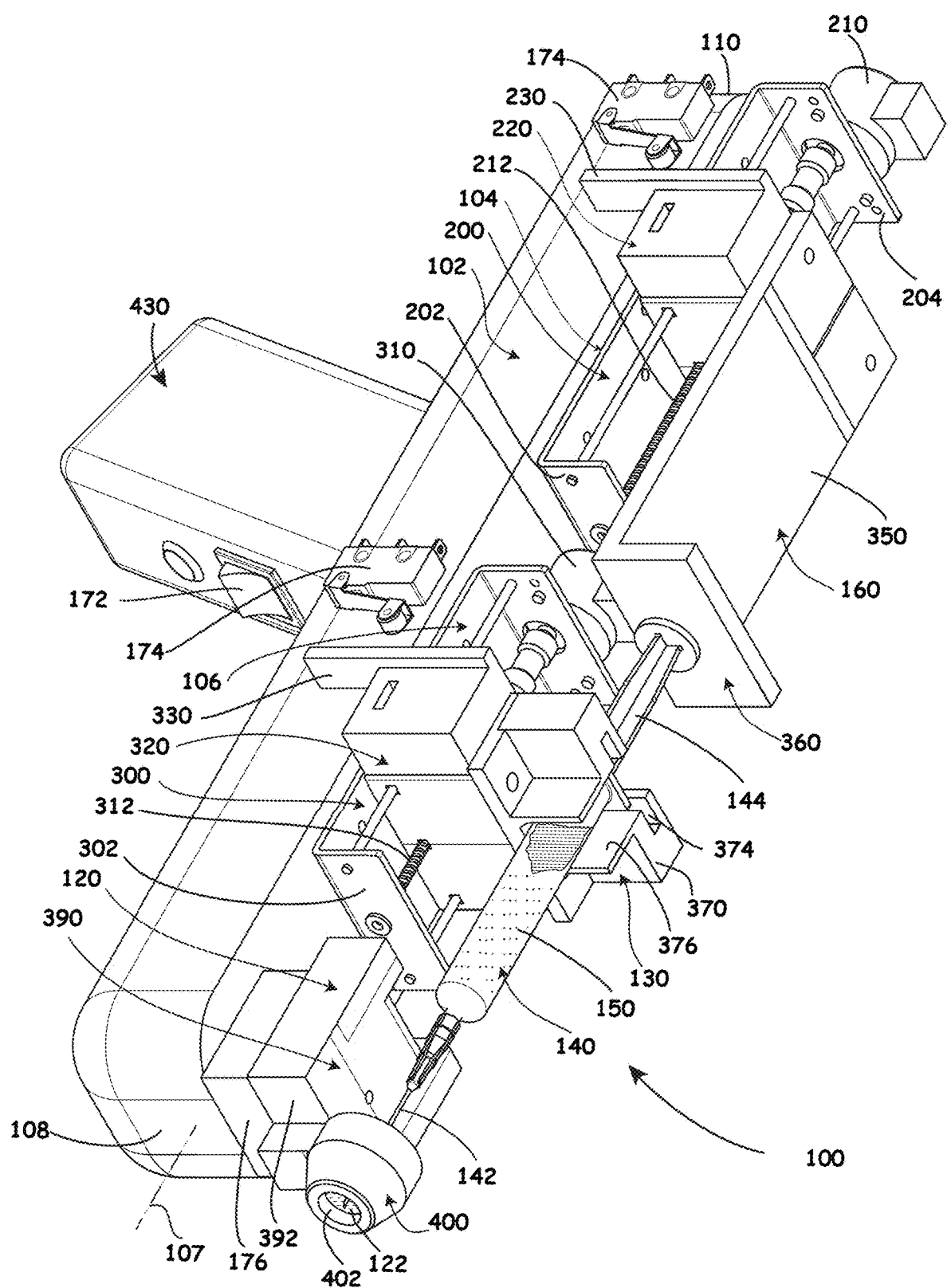
Figure 10C:
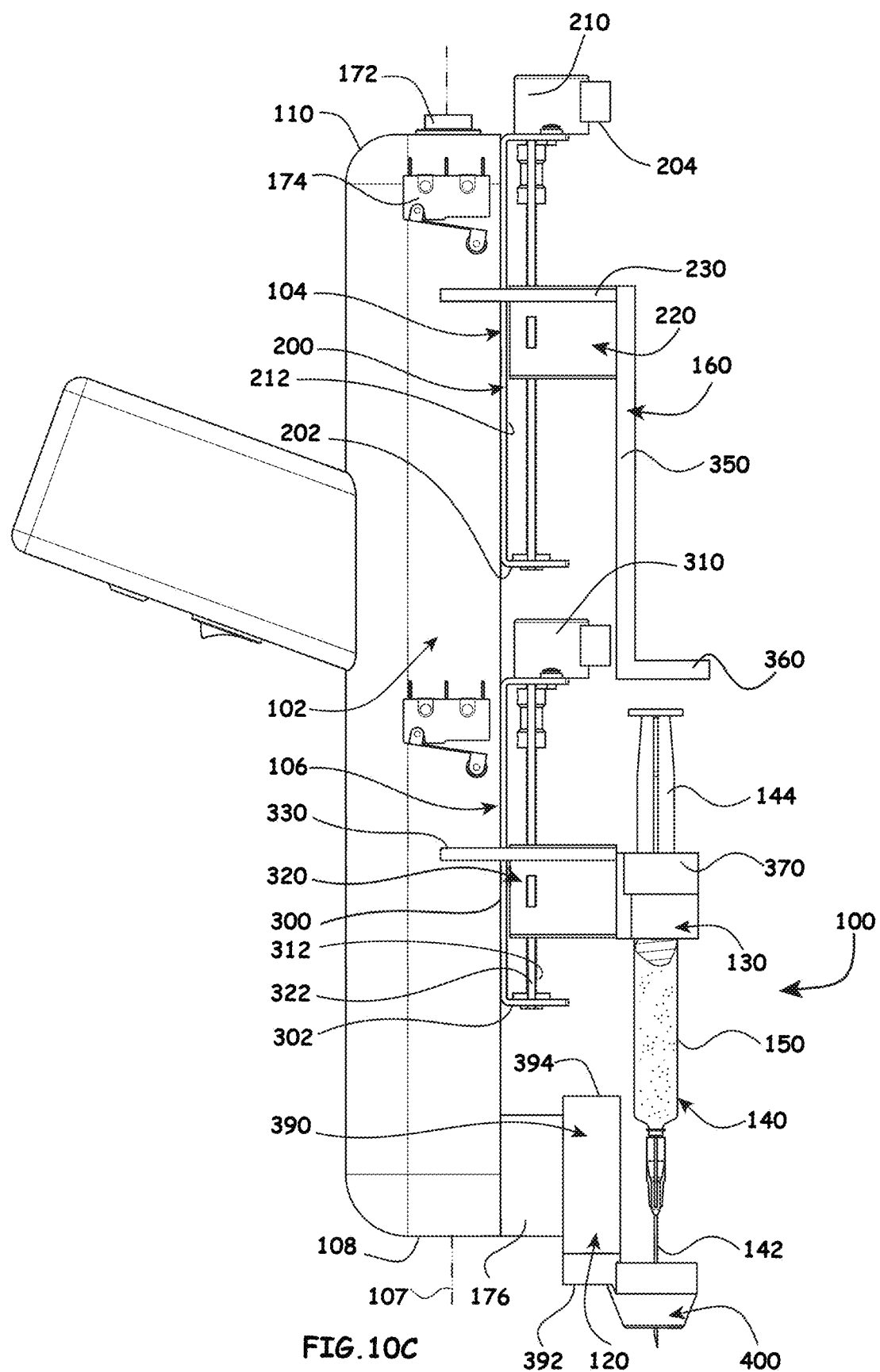

Reference is now made to FIGS. 10A-10C, which are simplified respective two different pictorial illustrations and an elevation illustration of a handheld assembled MPAI 100 having two motors, constructed and operative in accordance with an embodiment of the invention and showing the MPAI 100 in a first operative orientation.

It is appreciated that all spatial relationships between the various components of the MPAI 100 remain the same as described hereinabove with respect to the corded MPAI 100 illustrated in FIGS. 9A & 9B, besides that a handle 430 is attached to the base unit 102 and the user input elements 170 are disposed on the base unit 102 itself for manipulation by the user. The on/off switch 172, in accordance with an embodiment of the present invention, may be disposed on the base unit 102 itself, as illustrated in FIG. 10A or on the handle 430, as illustrated in FIG. 10B.

It is noted that the various electronic components, such as the controller, the various user input elements 170, the on-off switch 172 may be located within the base unit 102 or the handle 430. The MPAI 100 can be powered by rechargeable batteries or by AC, or AC to DC power supply.

It is a particular feature of another embodiment of the present invention that the needle 142 or an array of needles/micro-needles may reciprocate and contact skin or other tissues of the patient at variable angles relative to the handle 430 for proper function and optimal ergonomics. An example of this includes using the MPAI 100 on the oral palate. Modifiable angles between the reciprocating needles 142 and handle 430 can be achieved by employing mechanisms such as a hinge or constructing segments of the handle from materials with high plasticity. Hydraulic and pneumatic systems that transfer motion via pressure changes to the needle 142 to induce reciprocating needle motion are particularly advantageous to embodiments of the invention in which the angle between the longitudinal axis 107 of the needle 142 and the handle 430 are easily modified.

The MPAI 100 is illustrated in FIGS. 10A-10C in a storage operative orientation, in which the needle 142 is protected and the forward end thereof is concealed within the inner volume of the medicament reservoir 400 of the cartridge 120, such that the forward protrusion length of the needle 142 from the medicament reservoir 400 is defined as L0.

It is a particular feature of an embodiment of the present invention that the forward end of the needle 142 protrudes into a material disposed within the medicament reservoir 400, whereas the material is absorbed with medicament, which is in turn deposited onto the outer surface of the needle 142.

It is particularly seen in FIGS. 10A-10C that the first carriage assembly 104 is disposed at its initial storage operative orientation where the plunger rod driver 160 is not yet displaced relative to the base unit 102, so that the plunger engaging wall 360 of the plunger rod driver 160 is rearwardly spaced from the rearward flange of the plunger rod 144.

It is further particularly seen in FIGS. 10A-10C that the second carriage assembly 106 is disposed at its initial storage operative orientation where the syringe holder element 130 is not yet displaced relative to the base unit 102, so that the forward end of the needle 142 is disposed within the medicament reservoir 400 of the cartridge 120 and is protected therewithin.

Figure 11A:
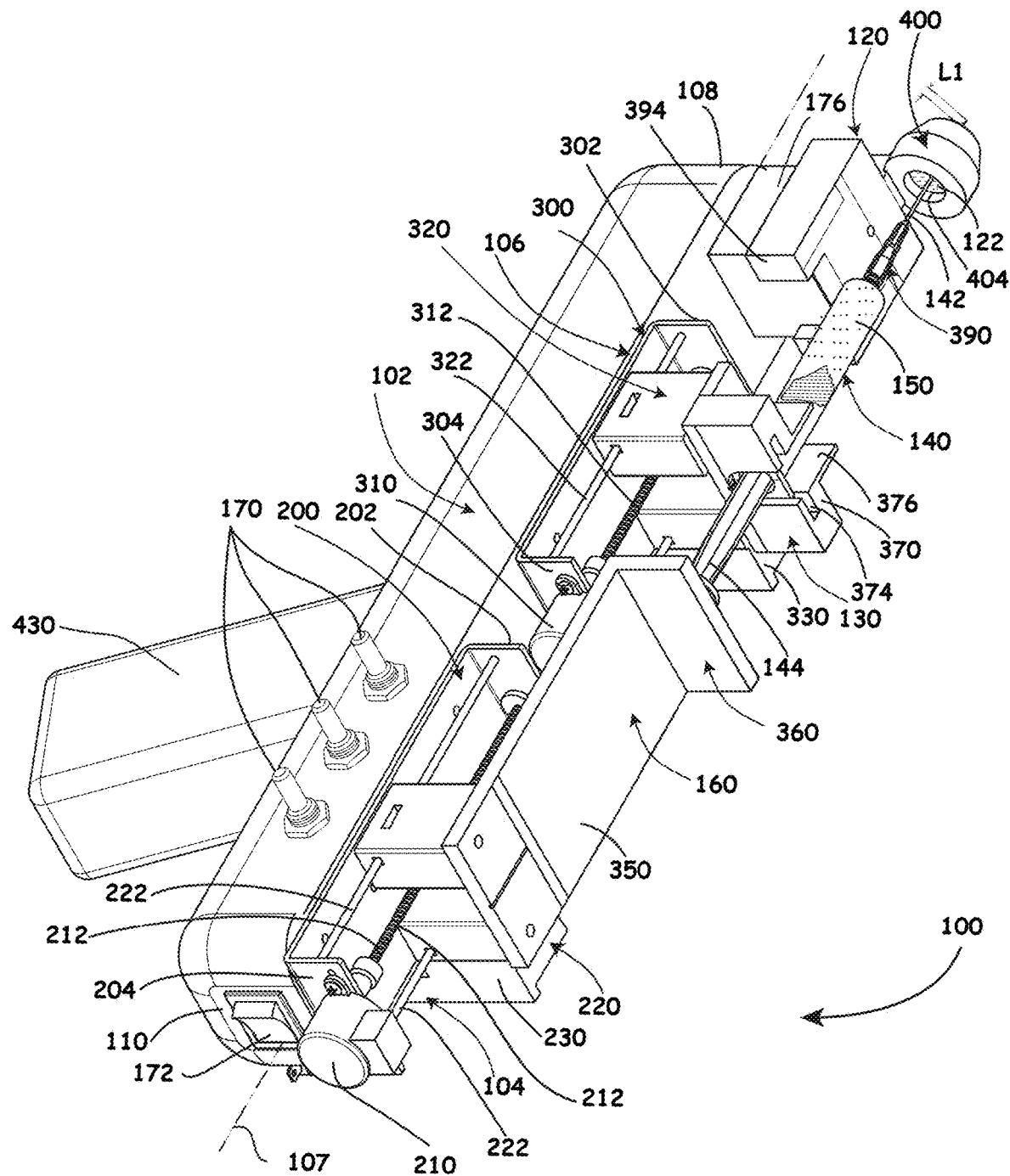
FIGS. 11A & 11B are simplified respective two different pictorial illustrations of the handheld assembled MPAI of FIGS. 10A-10C, showing the MPAI in a second operative orientation.
Figure 11B:
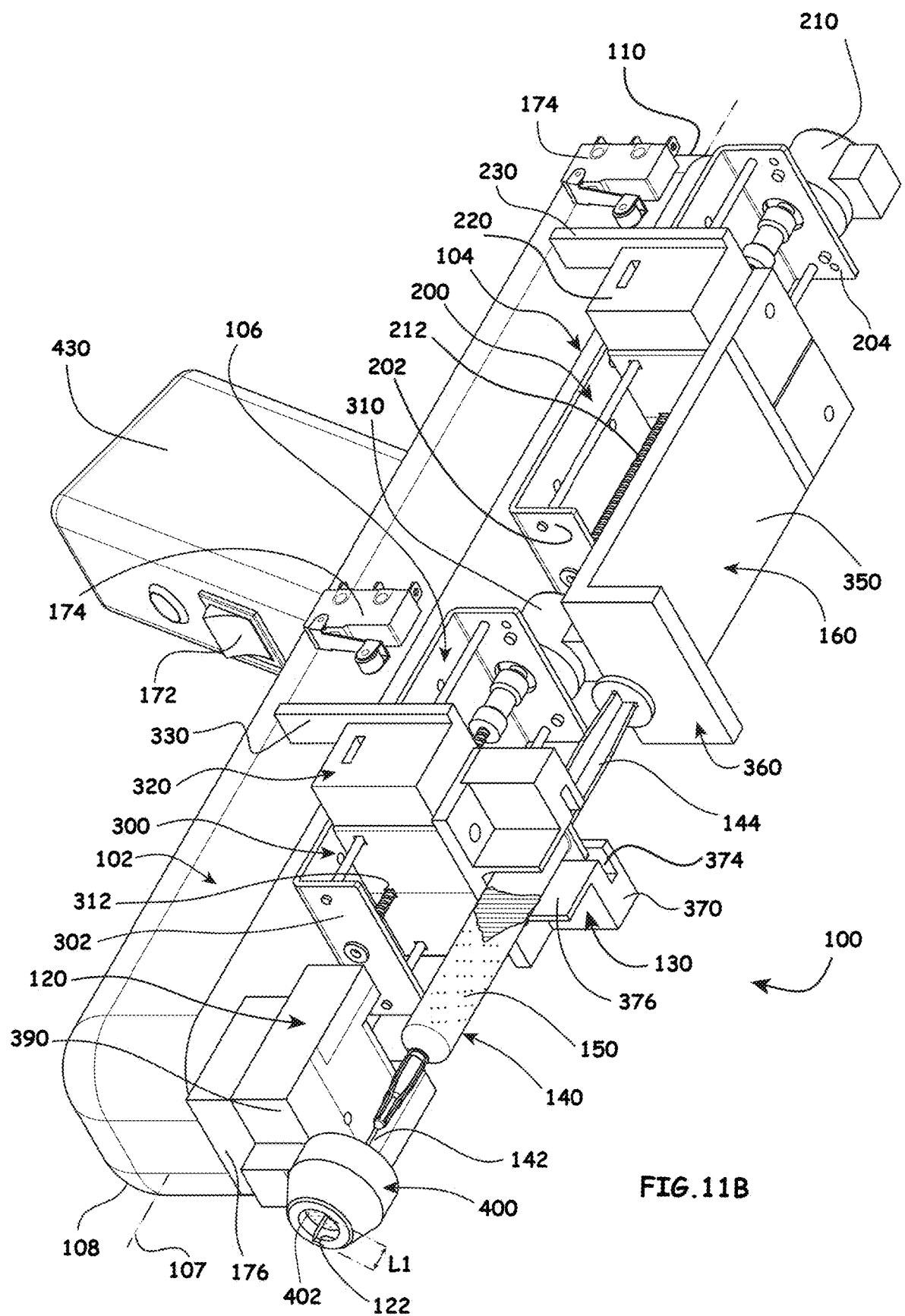

Reference is now made to FIGS. 11A & 11B, which are simplified respective two different pictorial illustrations of the handheld assembled MPAI 100 of FIGS. 10A-10C, showing the MPAI 100 in a second operative orientation.

It is appreciated that all spatial relationships between the various components of the MPAI 100 remain the same as described hereinabove and illustrated in FIGS. 10A-10C, besides the following:

The MPAI 100 is illustrated in FIGS. 11A & 11B in a first stage of reciprocating motion operative orientation, in which the needle 142 protrudes forwardly from the medicament reservoir 400 of the cartridge 120 to a first longitudinal extent L1, thus the needle 142 protrudes into the injection site under the skin of the patient to an initial depth L1.

It is a particular feature of an embodiment of the present invention that the medicament from the medicament cartridge 400 of cartridge 120 that is deposited onto the outer surface of needle 142 is delivered at depth L1 at the injection site and is deposited there in a tattoo-like manner.

It is particularly seen in FIGS. 11A & 11B that the first carriage assembly 104 is disposed at its initial storage operative orientation where the plunger rod driver 160 is not yet displaced relative to the base unit 102, so that the plunger engaging wall 360 of the plunger rod driver 160 is rearwardly spaced from the rearward flange of the plunger rod 144.

It is further particularly seen in FIGS. 11A & 11B that the second carriage assembly 106 is disposed at its first stage of reciprocating motion operative orientation where the syringe holder element 130 is forwardly axially displaced relative to the base unit 102 to a longitudinal extent L1, so that the forward end of the needle 142 protrudes forwardly from the forward end of medicament reservoir 400 of cartridge 120 to a distance of L1.

It is a particular feature of an embodiment of the present invention that the first stage of reciprocating motion is a repetitive stage, in which multiple reciprocations of the needle 142 to a depth of L1 under the skin of the patient are typically performed in order to deposit a sufficient amount of medicament from the medicament reservoir 400 of the cartridge 120 into depth L1 at the injection site.

Upon receipt of an appropriate signal from the controller of the MPAI 100, the second motor 310 is actuated and is operative to drive the second lead screw 312, which causes displacement of the second driven element 320 and thus the displacement of the syringe holder element 130 therealong. The syringe 140 is fixedly retained within the syringe holding element 130 and thus is displaced axially together therewith.

It is a particular feature of an embodiment of the present invention that the penetration depth of the needle 142 is controlled by second motor 310, thereby increasing the control and accuracy of needle depth penetration. The needle 142 is preferably displaced during its reciprocating motion according to specific algorithms related to the timing of a sequence of incremental increases in needle penetration depth, as described in detail hereinbelow. The specific algorithms can be selected by the user by means of mechanical or digital inputs, such as user input elements 170, for example.

In accordance with an algorithm controlling the operation of the MPAI 100, as described in detail hereinbelow, during each reciprocation of the needle 142, the syringe holder element 130 is displaced axially forwardly relative to base unit 102 to distance L1 and returns axially rearwardly relative to the base unit 102 to distance L0, as specifically illustrated in FIGS. 10A-10C.

Figure 12A:
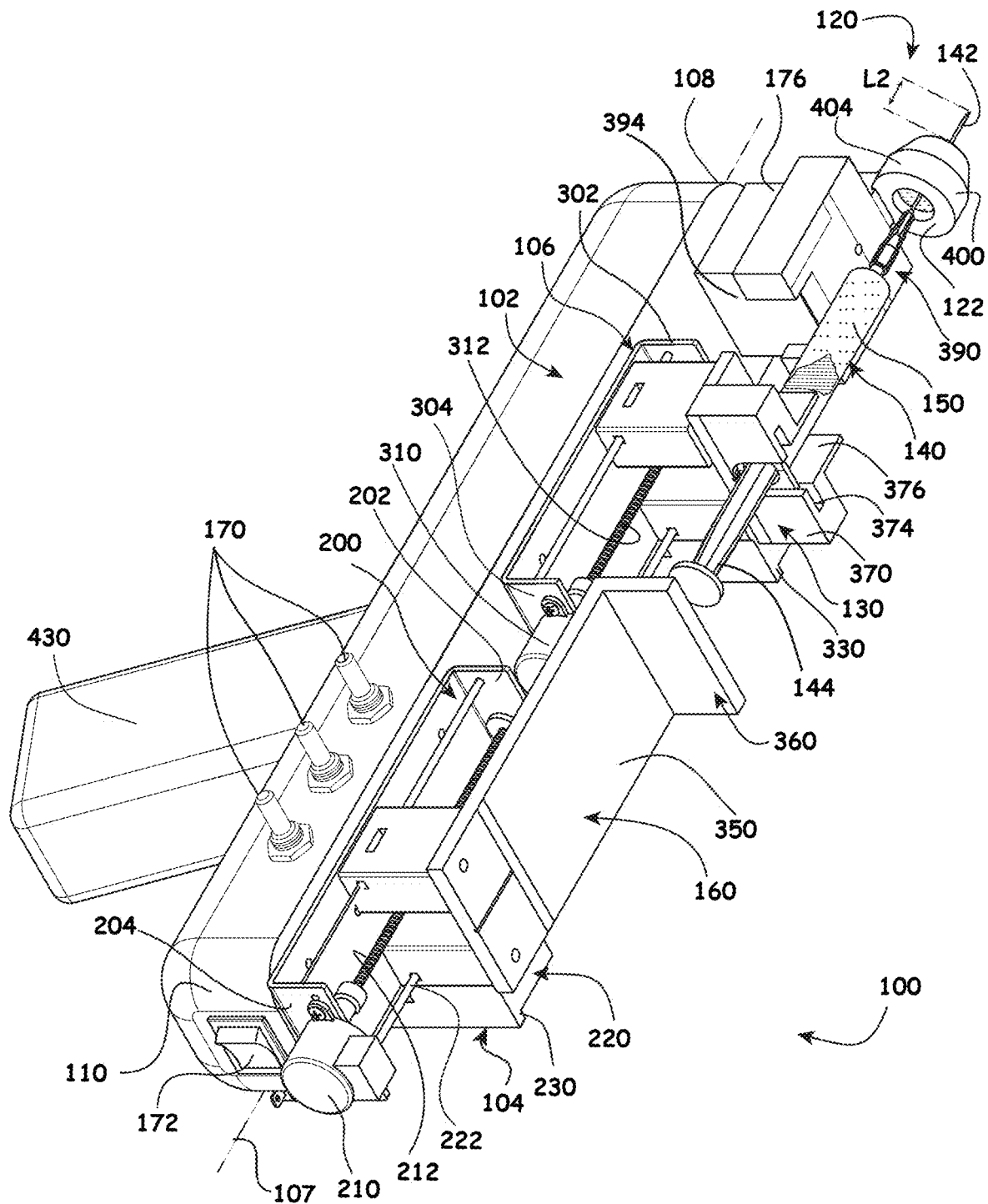
FIGS. 12A & 12B are simplified respective two different pictorial illustrations of the handheld assembled MPAI of FIGS. 10A-10C, showing the MPAI in a third operative orientation.
Figure 12B:
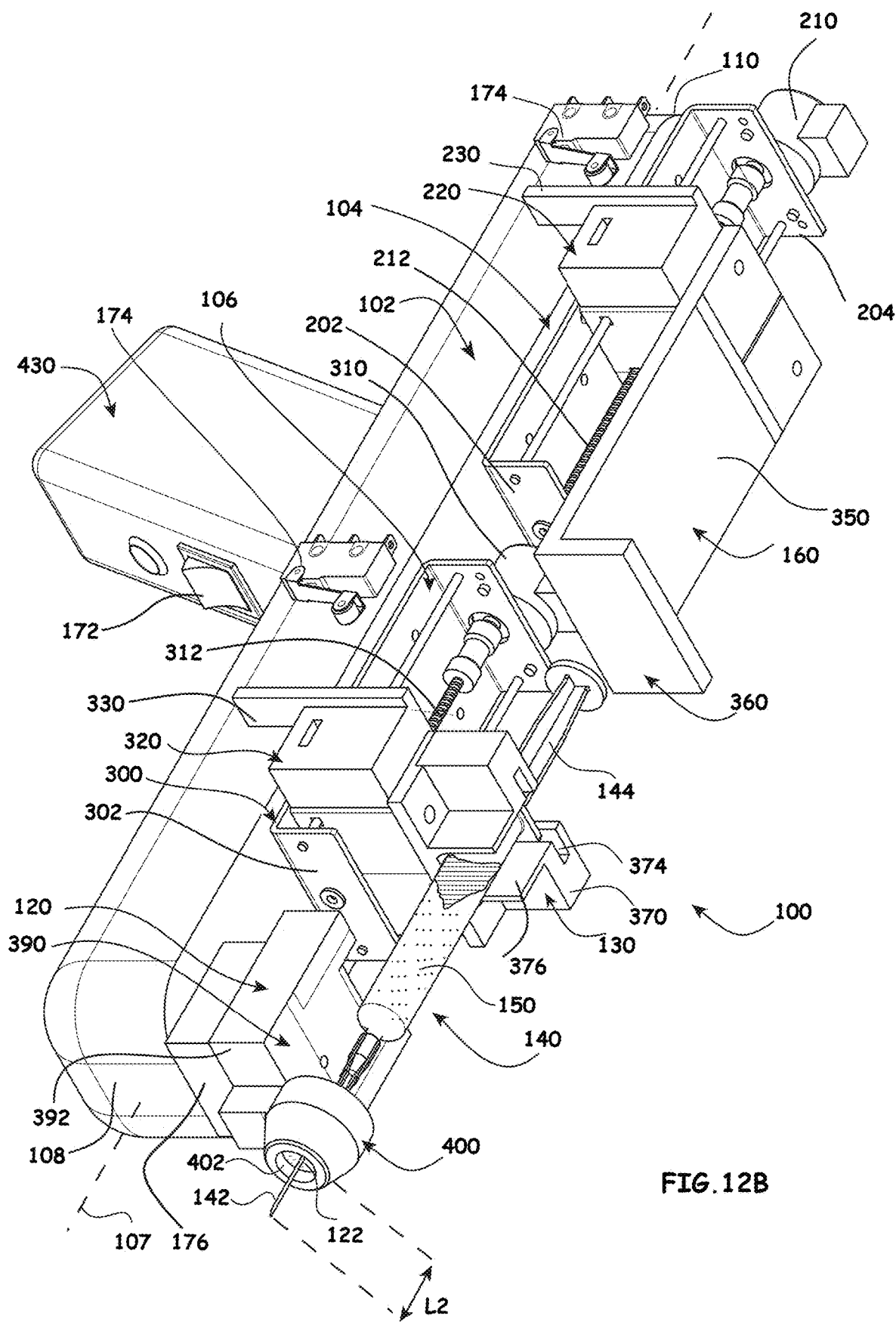

Reference is now made to FIGS. 12A & 12B, which are simplified respective two different pictorial illustrations of the handheld assembled MPAI 100 of FIGS. 10A-10C, showing the MPAI 100 in a third operative orientation.

It is appreciated that all spatial relationships between the various components of the MPAI 100 remain the same as described hereinabove and illustrated in FIGS. 11A & 11B, besides the following:

The MPAI 100 is illustrated in FIGS. 12A & 12B in a second stage of reciprocating motion operative orientation, in which the needle 142 protrudes forwardly from the medicament reservoir 400 of the cartridge 120 to a second longitudinal extent L2, generally greater than the first longitudinal extent L1, thus the needle 142 protrudes into the injection site under the skin of the patient to depth L2, greater than depth L1.

It is a particular feature of an embodiment of the present invention that the medicament from the medicament cartridge 400 of cartridge 120 that is deposited onto the outer surface of needle 142 is delivered at depth L2 at the injection site and is deposited there in a tattoo-like manner.

It is particularly seen in FIGS. 12A & 12B that the first carriage assembly 104 is disposed at its initial storage operative orientation where the plunger rod driver 160 is not yet displaced relative to the base unit 102, so that the plunger engaging wall 360 of the plunger rod driver 160 is rearwardly spaced from the rearward flange of the plunger rod 144.

It is further particularly seen in FIGS. 12A & 12B that the second carriage assembly 106 is disposed at its second stage of reciprocating motion operative orientation where the syringe holder element 130 is further forwardly axially displaced relative to the base unit 102 to a longitudinal extent L2, generally greater than longitudinal extent L1, so that the forward end of the needle 142 protrudes more forwardly from the forward end of medicament reservoir 400 of cartridge 120 to a distance of L2.

It is a particular feature of an embodiment of the present invention that the second stage of reciprocating motion is a repetitive stage, in which multiple reciprocations of the needle 142 to a depth of L2 under the skin of the patient are typically performed in order to deposit a sufficient amount of medicament from the medicament reservoir 400 of the cartridge 120 into depth L2 at the injection site.

In accordance with an algorithm controlling the operation of the MPAI 100, as described in detail hereinbelow, during each reciprocation of the needle 142, the syringe holder element 130 is displaced axially forwardly relative to base unit 102 to distance L2 and returns axially rearwardly relative to the base unit 102 to distance L0, as specifically illustrated in FIGS. 10A-10C.

It is noted that the first stage of reciprocating motion and the second stage of reciprocating motion are defined as the first mode of operation of the MPAI 100. It is a particular feature of an embodiment of the present invention that in the first mode of operation of the MPAI 100, the driven unit 220 of the first carriage assembly 104 is static with respect to the base unit 102 and the driven unit 320 of the second carriage assembly 106 is axially movable relative to the base unit 102, thus the plunger rod 144 is static relative to the syringe 140, thereby preventing ejection of the medicament 150 therefrom and the syringe 140 is axially displaceable relative to the base unit 102, thereby providing for administration of medicament 122 from the cartridge 120 at various depths under the skin of the patient by means of depositing the needle into the medicament reservoir 400 of the cartridge 120, which is filled with medicament 122.

In accordance with an embodiment of the present invention, any injectable pharmaceutical can be administered with reduced pain. The reduction of pain is achieved by the multiple-stage reciprocating motion of the syringe 140, as described and illustrated with reference to FIGS. 11A-12B, whereas a local anesthetic can be administered at depth L1 in a tattoo-like deposition manner and then additional anesthetic can be administered in an incremental fashion at depth L2. Upon delivery of anesthetic at depth L1, due to diffusion of the anesthetic, further needle advancement is achieved without pain, thereby providing for painless penetration of the hollow-bore needle 142 into the injection site.

It is appreciated that alternatively other methods of converting the second motor's 310 rotary motion to reciprocating linear motion of the needle 142 include mechanisms such as scotch yoke, swash plate, slider crank, electromagnetic systems, cam systems, etc. These mechanisms can replace the carriage assembly 106.

Further alternatively, hydraulic or pneumatic pressure mechanisms can be employed. In these mechanisms, a pump, such a peristaltic pump or piston pump, connected to a microcontroller, moves liquid or air within a tubing in a reciprocating positive and negative displacement manner Hydraulic pressure is transferred to a mechanism such as piston linked to the needle 142 which correspondingly moves forwardly and rearwardly in response to positive and negative fluid displacement driven by the pump.

It is an additional feature of an embodiment of the present invention that rotation of the syringe 140 along with needle 142, hypodermic needle, finger-stick lancet, piercing needle, burr, bit, or any other instrument capable of penetrating or abrading tissues for cosmetic or therapeutic interventions is employed. Rotary motion of the penetrating or abrading instrument around its longitudinal axis can be induced via electric rotary tools into which the penetrating or abrading instrument is secured, such as via a chuck. The rotary tool can be mounted onto the carriage assembly 104/106 instead of the syringe holding element 130. In these embodiments, progressive and intermittent forward displacement of the rotary tool into which the penetrating/abrading instrument is secured occurs according to the algorithms described and via the motor 210/310 linked to the carriage assembly 104/106 onto which the rotary tool is secured. Activating an algorithm while the rotary tool is actively spinning the penetrating or abrading instrument, causes the incremental and progressive advancement of the tip of the penetrating or abrading instrument beyond the forward end of the cartridge 120. Resulting penetration and/or abrasion of tissues at progressively increased depths results in deposition of medicament 122 within the medicament reservoir 400 of the cartridge 120 into the tissues at each incremental tissue depth.

It is noted that in accordance with embodiments of the present invention, vibrating tools, that are known to reduce sensitivity to painful stimulus may be incorporated into MPAI 100. Electric vibratory mechanisms, such as a motor spinning an offset weight on its shaft, can be integrated into the MPAI 100 to induce vibration that is transferred to the cartridge/patient interface so as to further decrease needle penetration and injection pain.

It is further noted that in accordance with embodiments of the present invention, lasers that are known to reduce sensitivity to a painful stimulus may be incorporated into MPAI 100. Lasers, with wavelengths including, but not limited to, 808 nm-830 nm, can be integrated into the MPAI 100 in a manner that focuses laser light onto the anatomic site intended for skin penetration during usage of the MPAI 100 so as to further decrease needle penetration and injection pain.

In accordance with a further embodiment of the present invention, a touch switch such as a capacitance switch, piezo switch, resistance switch, or other may be incorporated into the MPAI 100 and configured to be electronically linked to the needle 142. Contact of the needle 142 with the patient's skin is configured to be detected by the sensor to further enhance the precision of the reciprocation algorithms with respect to incremental depth advancements of the needle 142.

It is noted that tattooing method of depositing local anesthesia into the skin of the patient to minimize needle penetration pain requires that the location of contact between the forward end of the cartridge 120 and patient's body surface, therefore the needle penetration location, should not be altered once a reciprocation sequence is initiated. A change in the location of this interface would cause the next forward movement of the needle 142 to penetrate tissues that have not been anesthetized by the previous reciprocation and local anesthesia deposition, thereby stimulating pain.

It is a particular feature of an embodiment of the present invention that a motion sensor is incorporated into the MPAI 100 and is generally disposed on the forward end of the cartridge holder 176 of the forward end of the medicament reservoir 400 of the cartridge 120. It is noted that the motion sensor is configured to be activated upon initiation of a reciprocation algorithm. Motion of the patient relative to the MPAI 100 detected by the sensor during a reciprocation sequence triggers a pause in the reciprocation sequence and initiates any rearward movement of the needle 142 required to ensure the needle 142 is protected and the forward end thereof is concealed within the inner volume of the medicament reservoir 400 of the cartridge 120. Alternative methods to pause a reciprocation sequence in response to movement at the cartridge/patient interface include incorporation of a pressure or contact sensor into the MPAI 100 that detects pressure/contact between the MPAI 100 and the patient's tissues, such as by means of a limit switch. Alterations in the pressure measurement during a reciprocation cycle, as detected by the pressure/contact sensor, cause a pause in the reciprocation cycle and initiate any rearward movement of the needle 142 required to ensure the needle 142 is protected and the forward end thereof is concealed within the inner volume of the medicament reservoir 400 of the cartridge 120.

Motion or proximity sensors may be chosen from the group of passive infrareds (PIR), microwave, ultrasonic, hybrid, etc. Touch switches such as a capacitance switch, piezo switch, resistance switches that detects contact with a patient's skin can also be used to detect motion of the cartridge 120 relative to the patient after a reciprocation cycle is initiated.

In accordance with a still further embodiment of the present invention, a temperature-controlled heating mechanism such as a temperature-controlled electric axial fan heater, crossflow blow heater, polyimide heater, silicone rubber heater, foil heater, tubular heater, duct heater, strip heater, positive temperature coefficient heater, or other heat-generating mechanism is incorporated into the cartridge holder 176 or other part of the MPAI 100 to transmit heat to the medicament reservoir 400 of the cartridge 120, and ultimately to the medicament 122 stored therein. Heating of the medicament 122 can be accomplished by exposing the medicament reservoir 400 directly to heat emitted from said heating mechanism or by incorporating one or more heat-conductive elements into the construct of the cartridge 120, which, via contact with the heating mechanism, conducts heat into the medicament reservoir 400 of the cartridge 120. It is appreciated that heating of medicament 122 decreases the duration of onset of local anesthetic, thereby increasing the efficacy of the MPAI 100.

In accordance with yet another embodiment of the present invention a temperature-controlled warming cabinet is incorporated into the MPAI 100 or external electronic unit 420. The ambient temperature within the warming cabinet can be controlled by means such as a temperature-controlled electric axial fan heater, crossflow blow heater, polyimide heater, silicone rubber heater, foil heater, tubular heater, duct heater, strip heater, positive temperature coefficient heater, or other heat-generating mechanism. The warming cabinet can be used for storage of cartridge 120 prior to its use with the MPAI 100, so as to warm the medicament reservoir 400 and any medicament 122 stored therein. It is appreciated that heating of medicament 122 decreases the duration of onset of local anesthetic, thereby increasing the efficacy of the MPAI 100.

Figure 13A:
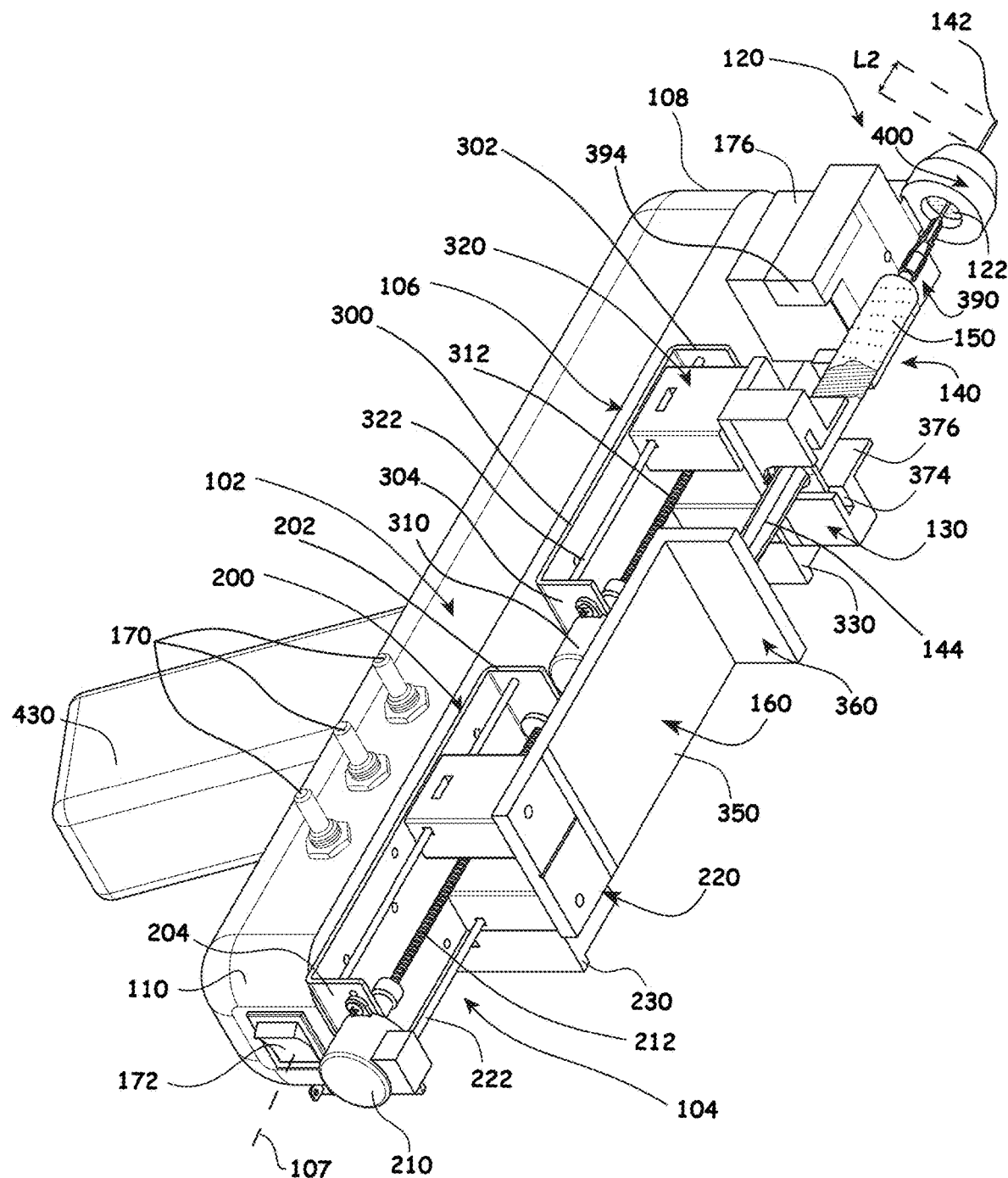
FIGS. 13A & 13B are simplified respective two different pictorial illustrations of the handheld assembled MPAI of FIGS. 10A-10C, showing the MPAI in a fourth operative orientation.
Figure 13B:
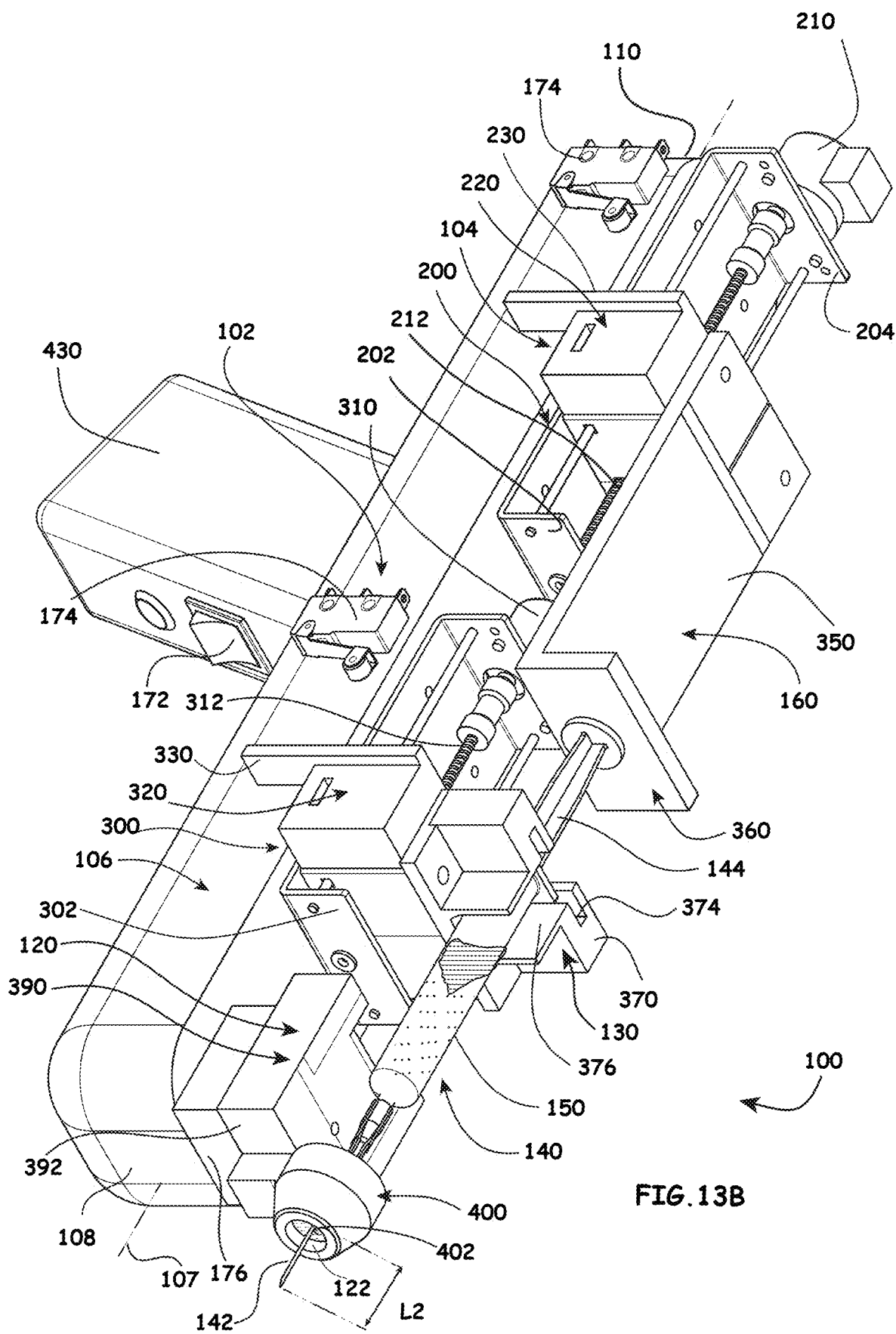

Reference is now made to FIGS. 13A & 13B, which are simplified respective two different pictorial illustrations of the handheld assembled MPAI 100 of FIGS. 10A-10C, showing the MPAI 100 in a fourth operative orientation.

It is appreciated that all spatial relationships between the various components of the MPAI 100 remain the same as described hereinabove and illustrated in FIGS. 12A & 12B, besides the following:

The MPAI 100 is illustrated in FIGS. 13A & 13B in a plunger rod engagement operative orientation, in which the needle 142 still protrudes forwardly from the medicament reservoir 400 of the cartridge 120 to a second longitudinal extent L2 and the plunger rod driver 160 engages the rearward flange of the plunger rod 144.

It is particularly seen in FIGS. 13A & 13B that the first carriage assembly 104 is disposed at its plunger rod engagement operative orientation where the plunger rod driver 160 is slightly axially forwardly displaced relative to the base unit 102, so that the plunger engaging wall 360 of the plunger rod driver 160 now engages the rearward flange of the plunger rod 144.

It is further particularly seen in FIGS. 13A & 13B that the second carriage assembly 106 remains at its second stage of reciprocating motion operative orientation where the syringe holder element 130 is disposed at its forward position relative to the base unit 102, where the forward end of the needle 142 protrudes forwardly from the forward end of medicament reservoir 400 of cartridge 120 to a distance of L2.

Upon receipt of an appropriate signal from the controller of the MPAI 100, the second motor 310 is deactivated at a state where the needle protrudes from the forward end of the medicament reservoir 400 of the cartridge to a distance L2. It is a particular feature of an embodiment of the present invention that the deactivation of the second motor 310 is based on a pre-determined value of needle protrusion from the forward end of the medicament reservoir 400, such as L2 for example. Alternatively, the deactivation of the second motor 310 is based on a reading of a sensor, such as a proximity sensor, as described in detail hereinbelow.

It is a particular feature of an embodiment of the present invention, that upon deactivation of the second motor 310, and upon receipt of an appropriate signal from the controller of the MPAI 100, the first motor 210 is now actuated and is operative to drive the first lead screw 212, which causes displacement of the first driven element 220 and thus the displacement of the plunger rod driver 160 therealong. It is seen in FIGS. 13A & 13B that in this plunger rod engagement operative orientation the plunger rod driver 160 is forwardly axially displaced up to engagement of the plunger engaging wall 360 with the rearward flange of the driver rod 144.

It is noted that the syringe 140 along with the needle 142 remain in the same axial orientation as described and illustrated with reference to FIGS. 12A & 12B.

Figure 14A:
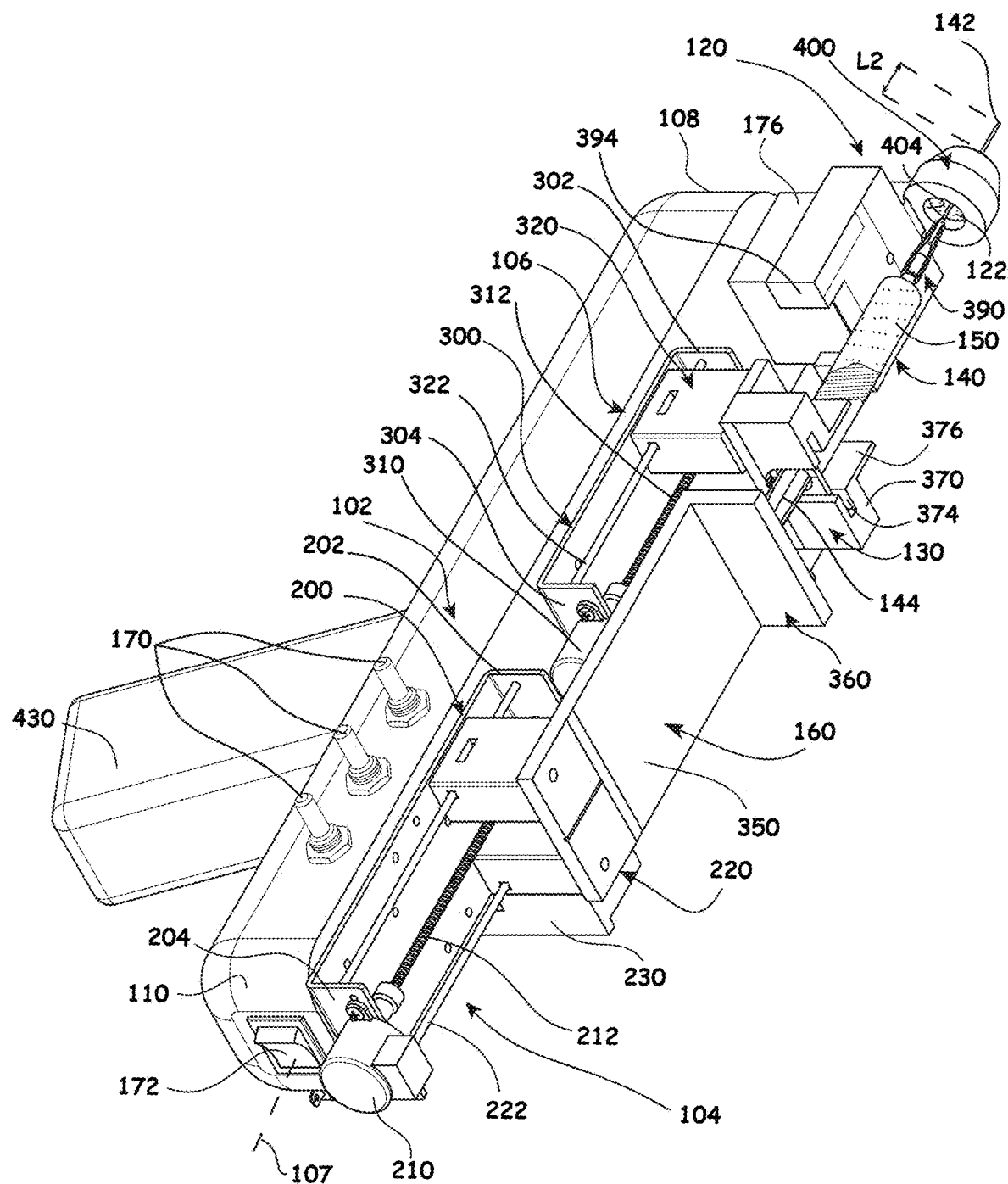
FIGS. 14A & 14B are simplified respective two different pictorial illustrations of the handheld assembled MPAI of FIGS. 10A-10C, showing the MPAI in a fifth operative orientation.
Figure 14B:
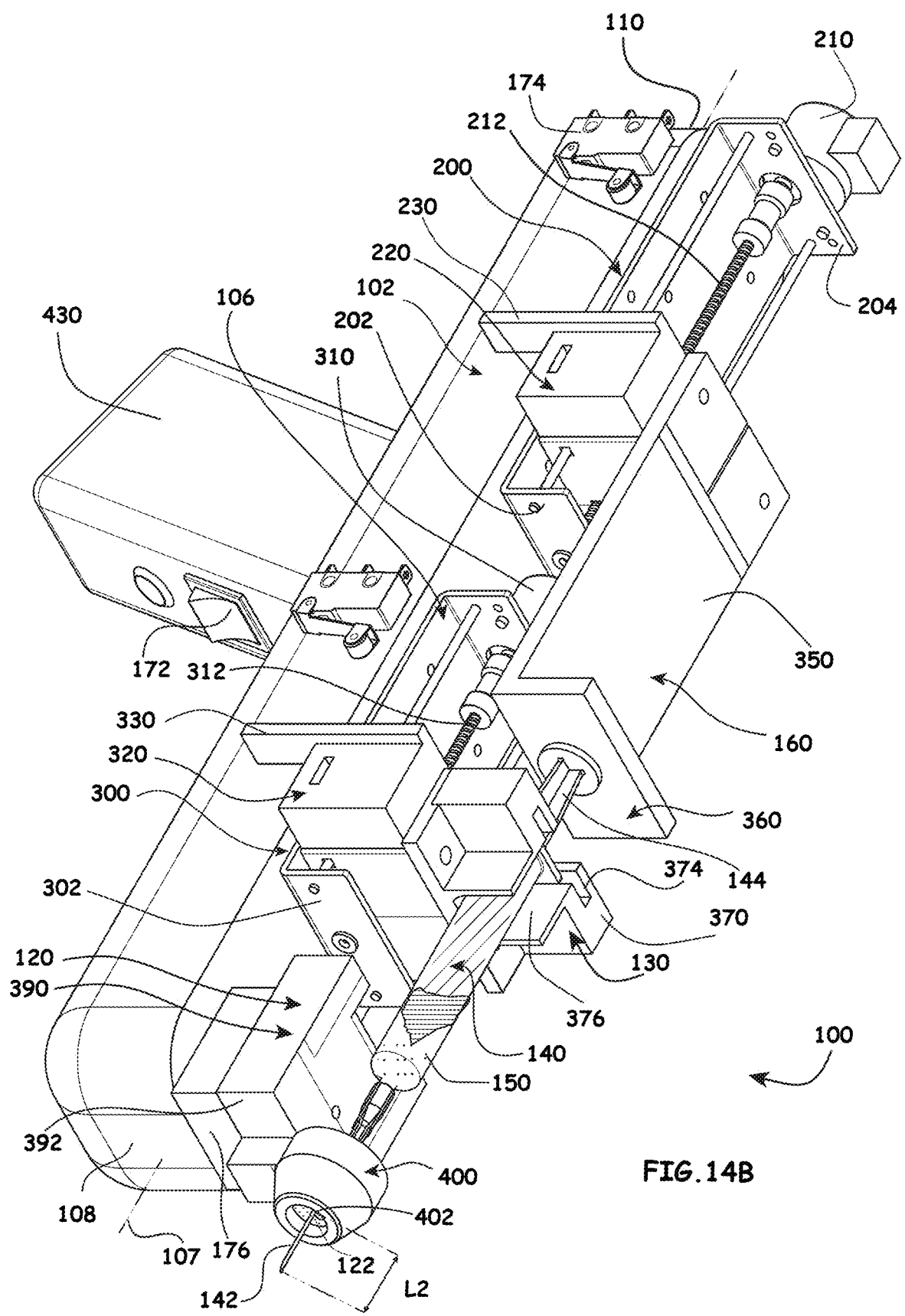

Reference is now made to FIGS. 14A & 14B, which are simplified respective two different pictorial illustrations of the handheld assembled MPAI 100 of FIGS. 10A-10C, showing the MPAI 100 in a fifth operative orientation.

It is appreciated that all spatial relationships between the various components of the MPAI 100 remain the same as described hereinabove and illustrated in FIGS. 13A & 13B, besides the following:

The MPAI 100 is illustrated in FIGS. 14A & 14B in an injection operative orientation, in which the needle 142 still protrudes forwardly from the medicament reservoir 400 of the cartridge 120 to a second longitudinal extent L2 and the plunger rod driver 160 is axially displaced forwardly relative to the base unit 102, thereby axially forwardly displacing the plunger rod 144 relative to the syringe 140, causing ejection of the medicament 150 from the syringe 140 via the needle 142 and into the injection site. Preferably, the medicament 150 is injected at a depth L2 under the skin of the patient, at which the needle reciprocations have stopped in accordance to the instructions provided to the controller by the algorithm controlling the operation of the MPAI 100. Alternatively, the medicament 150 may be injected at any other depth, as defined by the user. For example, once the needle 142 is penetrated to depth L2, it may be retracted slightly prior to injection of medicament 150.

It is particularly seen in FIGS. 14A & 14B that the first carriage assembly 104 is disposed at its injection operative orientation where the plunger rod driver 160 is further axially forwardly displaced relative to the base unit 102, so that the plunger engaging wall 360 of the plunger rod driver 160 displaces the plunger rod 144 relative to the syringe 140.

It is further particularly seen in FIGS. 14A & 14B that the second carriage assembly 106 remains at its second stage of reciprocating motion operative orientation where the syringe holder element 130 is disposed at its forward position relative to the base unit 102, where the forward end of the needle 142 protrudes forwardly from the forward end of medicament reservoir 400 of cartridge 120 to a distance of L2.

As seen in FIGS. 14A & 14B, the first motor 210 now drives the first lead screw 212, which causes further forward axial displacement of the first driven element 220 and thus the displacement of the plunger rod driver 160 therealong. It is seen in FIGS. 14A & 14B that in this injection operative orientation the plunger rod driver 160 is forwardly axially displaced by engagement thereof with the plunger engaging wall 360 to effect injection of the medicament 150 via the needle 142 into the injection site.

It is noted that the syringe 140 along with the needle 142 remain in the same axial orientation as described and illustrated with reference to FIGS. 12A & 12B.

It is noted that the plunger rod engagement operative orientation and the injection operative orientation are defined as the second mode of operation of the MPAI 100. It is a particular feature of an embodiment of the present invention that in the second mode of operation of the MPAI 100, the driven unit 320 of the second carriage assembly 106 is static with respect to the base unit 102 and the driven unit 220 of the first carriage assembly 104 is axially movable relative to the base unit 102. As a result, the syringe 140 and the needle 142 are static relative to the cartridge 120, thereby preventing depositing of medicament 122 from the cartridge 120 into the skin and the plunger rod 144 is axially movable relative to the syringe 140, thereby providing for ejection of the medicament 150 from the syringe 140 via the needle 142 and into the injection site under the skin of the patient, at the desired depth L2, or any other desired depth, as provided by the algorithm controlling the operation of the MPAI 100.

The medicament 150 may be an additional local anesthetic, insulin, a vaccine, steroid, or any other injectable agent. It is a further particular feature of an embodiment of the present invention that the medicament 150 can be administered through the same needle 142 at a controlled rate, governed by the controller based on either manual selection of the user or by a predefined schedule stored in the algorithm controlling the operation of the MPAI 100.

It is a particular feature of an embodiment of the present invention that the same needle 142 serves both for tattoo-like deposition of the second medicament 122, such as local anesthesia in the first mode of operation of the MPAI 100 and as conduit for injection of the first medicament 150.

It is noted that a traditional syringe 140 with plunger rod 144 engaged by a programmable plunger rod driver 160 can be used to inject medicament 150 through the needle 142 as described in detail with reference to FIGS. 14A & 14B. Alternatively, other means that deliver a medicament through a hollow-bored needle in a controlled, programmable manner can be used in place of the traditional syringe. These include other electric pump systems (centrifugal pumps, diaphragm pumps, lobe pumps, gear pumps, screw pumps, peristaltic pumps, and others) that are linked to a needle and are programmable with respect to rate of fluid movement. Further alternatively, manual pumps that allow for rate-controlled, incremental fluid movement, such as via a jack-screw, ratchet mechanism, or other manual mechanisms can also be utilized in accordance with other embodiments of the present invention.

It is further noted that a standard hypodermic needle 142 that is attached to a standard syringe 140 can be replaced by a needle platform consisting of a plurality of needles linked to a syringe or other pump. The needle platform may consist of a plurality of hollow-bored needles or solid needles. Each hollow-bore needle may be used to both deposit local anesthesia contained within the cartridge 120 in a tattoo-like manner and as a conduit through which medicament 150 is deliverable into the tissue by the syringe 140 or other pump. A solid needle can serve only to deposit local anesthesia. It is appreciated that a needle platform may increase the surface area and volume of tissue that is subjected to local anesthesia deposition and/or medicament injection during single use of the MPAI 100.

In accordance with a further embodiment of the present invention, playback of electronically stored audio tunes, or sounds is incorporated into MPAI 100, by means of digital audio stored in a microprocessor and transmitted to audio speakers integrated into the MPAI 100. Playback of audio, such as a comforting melody, during a reciprocation and/or injection sequence assists in decreasing patient anxiety associated with hearing the sounds of the working device and alleviates the more general anxiety felt by many patients during a medical injection procedure.

Figure 15A:
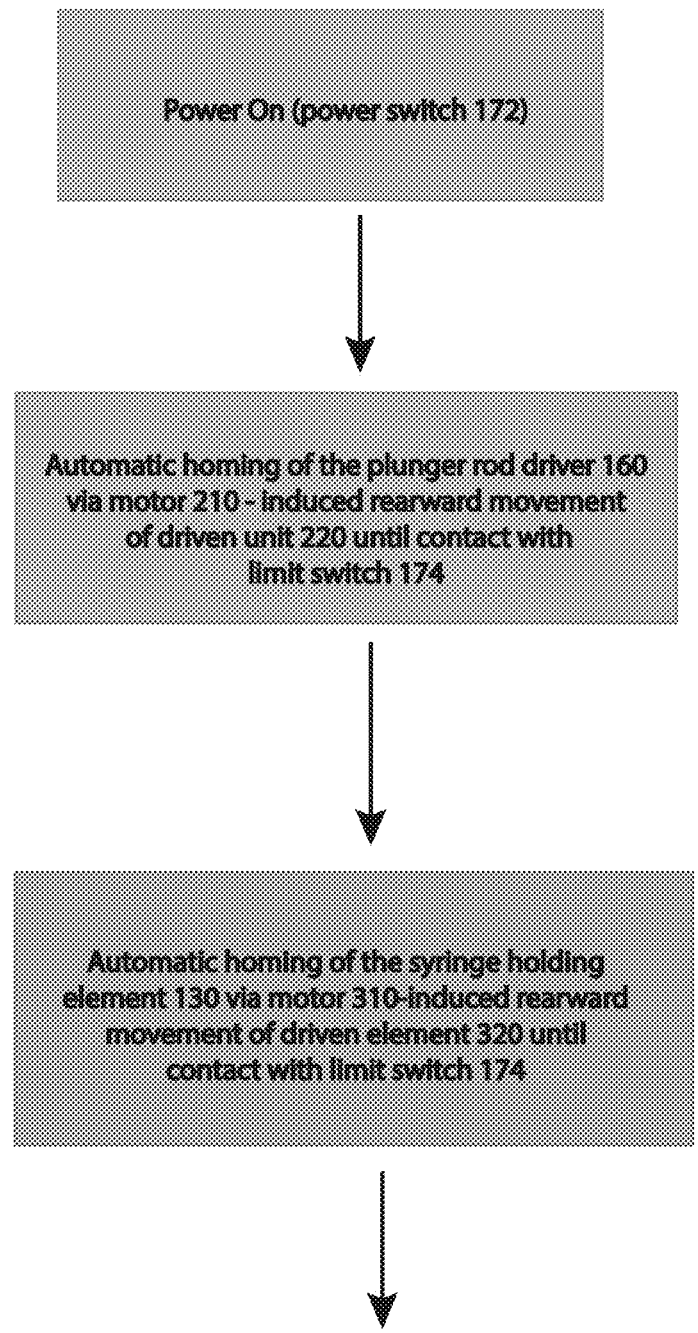
Figure 15C:
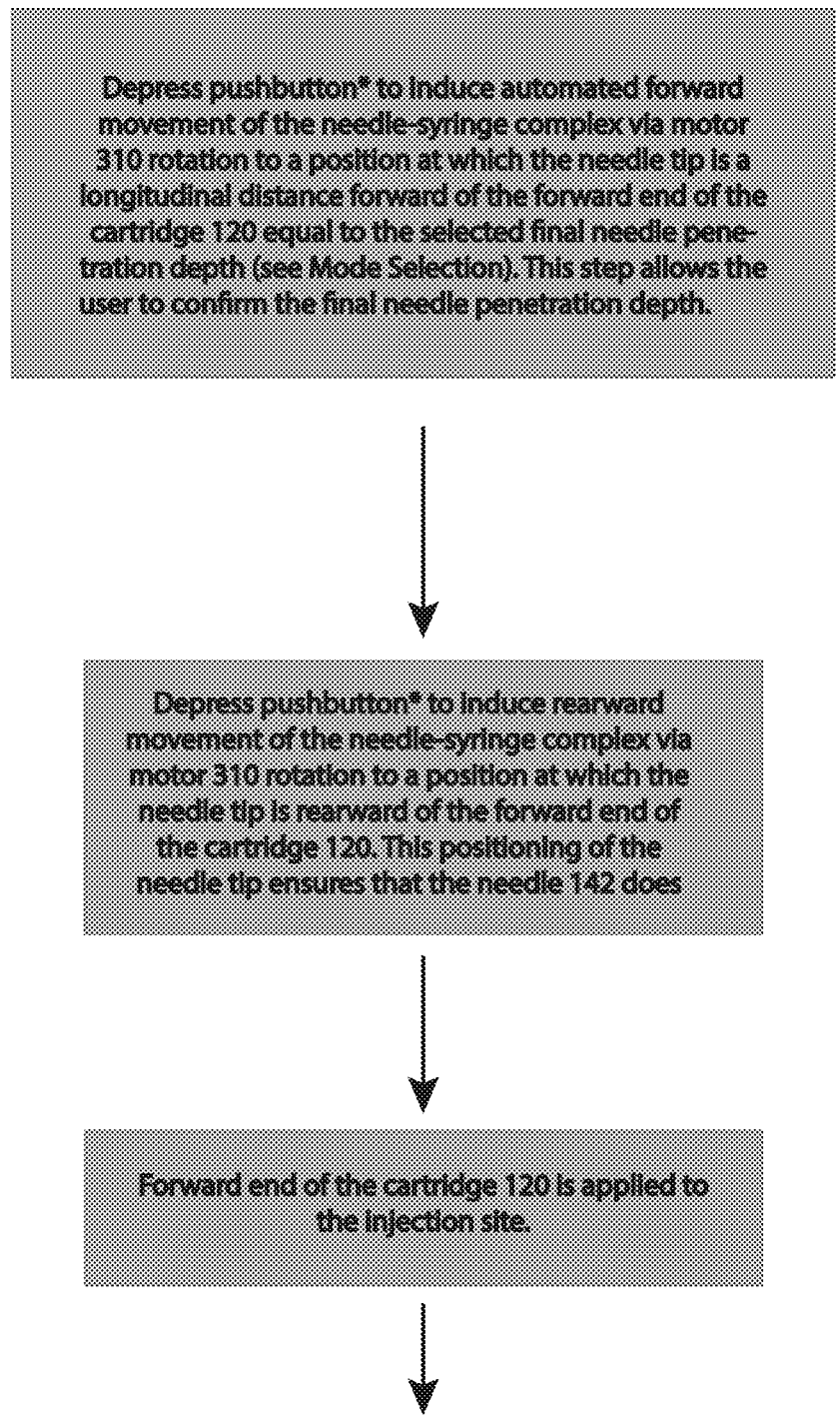
Figure 15D:
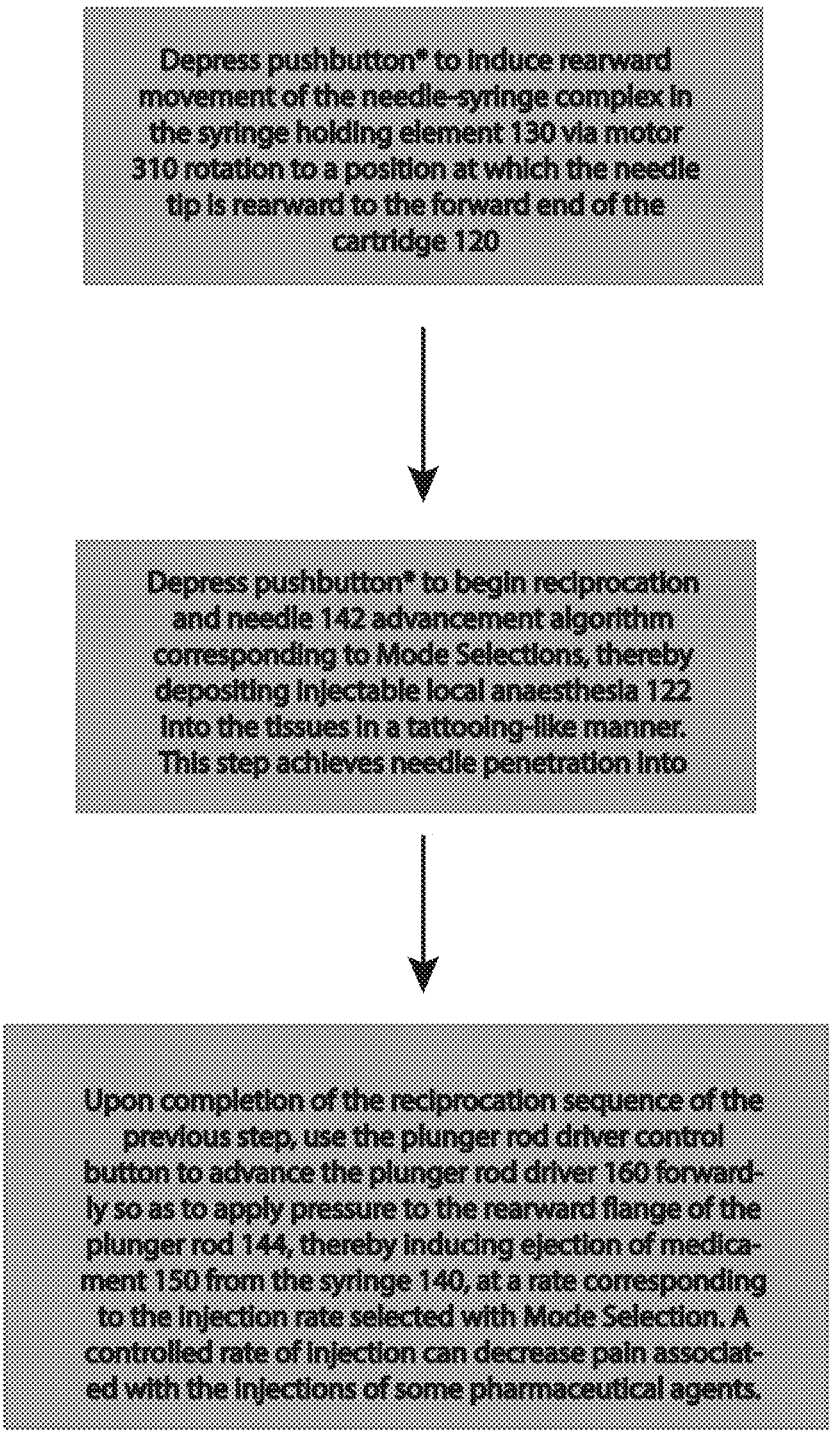

Reference is now made to FIG. 15, which is a simplified flow chart illustrating the usage of the MPAI 100 of FIGS. 1A-14B and to FIGS. 16A-16D, which are a simplified diagram illustrating the usage of the MPAI 100 in several operative orientations, as specifically illustrated in FIGS. 10A-12B.

FIGS. 15A-15D and 16A-16D illustrated an exemplary method of usage of the MPAI 100, as described and illustrated in FIGS. 1A-14B.

It is seen in the various steps described in the flowchart of FIG. 15 that typically, the syringe 140 is filled with medicament 150 to be injected and needle 142 is attached to the syringe 140. Cartridge 120 is supplied with a volume of injectable local anesthesia 122 and installed onto the base unit 102. The syringe 140 is installed onto the syringe holder element 130. Mode selection is performed by a user, as described in detail hereinbelow. The user applies the forward end of the cartridge 120, specifically the forward end of the medicament reservoir 400 of the cartridge 120 to the patient's skin at the injection site. At this initial storage operative orientation, as specifically illustrated and described with reference to FIGS. 10A-10C, the needle tip remains, by virtue of the relative positions of the cartridge 120 and syringe holding element 130, rearward of the forward end of the medicament reservoir 400 of cartridge 120, so that the needle tip does not contact the patient's skin.

Using the user input elements 170, the MPAI 100 initiates algorithmic sequence of reciprocations and incremental linear advancements of the needle 142 such that local anesthesia 122 within the cartridge 120 is deposited in a tattooing manner into the skin at progressively increasing depths until a desired final depth has been reached, as specifically illustrated in FIGS. 16A-16D.

Upon completion of the sequence of reciprocations of needle 142, user input advances the plunger rod driving element 160 axially forwardly to engage the rearward flange of the plunger rod 144, as specifically illustrated and described with reference to FIGS. 13A & 13B. Resulting forward displacement of the plunger rod 144 relative to syringe 140 induces injection of the medicament 150, via the already penetrated needle 142, into the patient's tissues, as specifically illustrated and described with reference to FIGS. 14A & 14B.

The plunger rod driver 160 is displaced axially forwardly at a rate determined by mode selection, as described in detail hereinbelow, such that the rate of injection is controlled. In an alternative embodiment, an algorithm combines reciprocations of the needle 142 at incrementally increased needle penetration depths with coordinated, automated advancement of the plunger rod driver 160 such that volumes of medicament 150 within the syringe 140 are injected at select depths in the tissues as the reciprocation sequence progresses, and/or after it has completed.

Upon completion of injection of medicament 150, user input causes withdrawal of the needle 142 from the patient's skin via homing of the syringe holding element 130. Homing of the syringe holding element 130 also establishes baseline positioning of the components as illustrated in FIGS. 10A-10C, in which the needle 142 is protected within the medicament reservoir 400 of cartridge 120, such that the cartridge 120 can be removed from the skin and the syringe 140 with needle 142 can be removed from the MPAI 100.

It is a particular feature of an embodiment of the present invention that the algorithm of the MPAI 100 is configured to precisely control: (i) the initial position of the needle 142, and (ii) rate of needle penetration depth advancement. This allows for initial, painless, penetration of the skin into the most superficial layer of the skin that is above the level of the pain-sensitive nociceptors, as described in detail in Table 1, hereinbelow and illustrated in FIGS. 16A-16D.

Needle reciprocation at level L1, that is superficial to the nociceptors for a duration T1, will deposit local anesthetic 122 at this level, but also at a deeper level L2, due to the effects of (i) passive diffusion and (ii) active "pushing" of medicament 122 to a deeper level by reciprocating action of the needle tip. Once duration T1 has elapsed, the algorithm will then instruct the system to advance the needle 142 to the next depth level L2, which is expected to have already been anesthetized by reciprocations at level L1. A sequence of incremental needle advancements (L1 . . . Ln) each with corresponding durations (T1 . . . Tn) is repeated until a maximum depth of needle penetration is reached.

TABLE 1

| Advancement Level, L | Needle Penetration Depth | Duration, T (T is determined by the total number and frequency of reciprocations at a given level, L, and any pauses in reciprocation associated with that level) |
|---|---|---|
| L0 = Homed Position | reciprocating needles positioned so as to not penetrate skin at all | N/A |
| L1 | reciprocating needles advance to skin level above anticipated depth of local skin nociceptors based on empirical knowledge of tissue anatomy, thereby entering skin without a painful stimulus | T1 = time expected for medicament 122 deposited at this level to reach L2 by passive diffusion and needle action |
| L2 | depth that medicament 122 deposited at level L1 is expected to reach | T2 = time expected for medicament 122 deposited at this level to reach L3 by passive diffusion and needle action |
| L3 | depth that medicament 122 deposited at level L2 is expected to reach | T3 = time expected for medicament 122 deposited at this level to reach L4 by passive diffusion and needle action |
| Ln | depth that medicament 122 deposited at level (n − 1) is expected to reach | Tn = time expected for medicament 122 deposited at this level to reach level (n + 1) by passive diffusion and needle action |

It is a particular feature of an embodiment of the present invention that the controller stores a number of pre-programmed algorithms, selectable by the user, each of which choreographs a unique sequence of movements related to the magnitude of incremental increases in needle penetration depths, (L0 to L1), (L1 to L2), (L2 to L3) . . . , the number of reciprocations that occur and any pauses in reciprocations that are programmed to occur before further needle advancement as described in detail in Table 1 hereinabove. Mode-selection functionality, via a mechanical switch, dial, or digital input mechanism, such as user input elements 170 allows the user to change the "active" algorithm based on a variety of criteria.

According to one embodiment of the present invention, mode selection allows the user to choose the anatomical name of the body site being addressed (e.g. SCALP, FACE, NECK, CHEST, ABDOMEN, etc. . . . ), each selection initiating a unique algorithm designed to work most optimally and efficiently for that particular body site.

According to another embodiment of the present invention, mode selection allows the user to choose the generally accepted notion of pain-sensitivity that is associated with needle penetration at the body site (e.g. LOW, MODERATE, HIGH, EXTREME), each selection initiating a unique algorithm designed to work most optimally and efficiently for that pain-sensitivity level.

According to further embodiment of the present invention, mode selection allows the user to choose final needle penetration depth upon completion of incremental advancements (e.g. 1 mm, 2 mm, 3 mm . . . ).

According to still further embodiment of the present invention, mode selection allows the user to choose the rate of forward advancement of the plunger rod 144 relative to the syringe via forward movement of the associated driven element 220 (or rate of fluid delivery by alternate pump systems) so as to control the rate of injection of medicament 150 through the needle 142 and into the tissues (e.g. 0.1 cc/sec, 0.2 cc/sec, 0.3 cc/sec . . . OR 0.1 cc/button push, 0.2 cc/button push, etc.).

According to yet further embodiment of the present invention, mode selection allows the user to choose the syringe size and brand (e.g. by volume, 3 cc, 5 cc, 10 cc), and needle length and brand (e.g. 10 mm, 13 mm, 16 mm) to be used for the needle-syringe complex. This selection causes automated adjustments to the algorithms, including the baseline/homed position of the syringe holding element 130 to ensure correct relative positions between the syringe holding element 130 and cartridge holder 176, and therefore the tip of needle 142 and forward end of the cartridge 120.

Figure 17A:
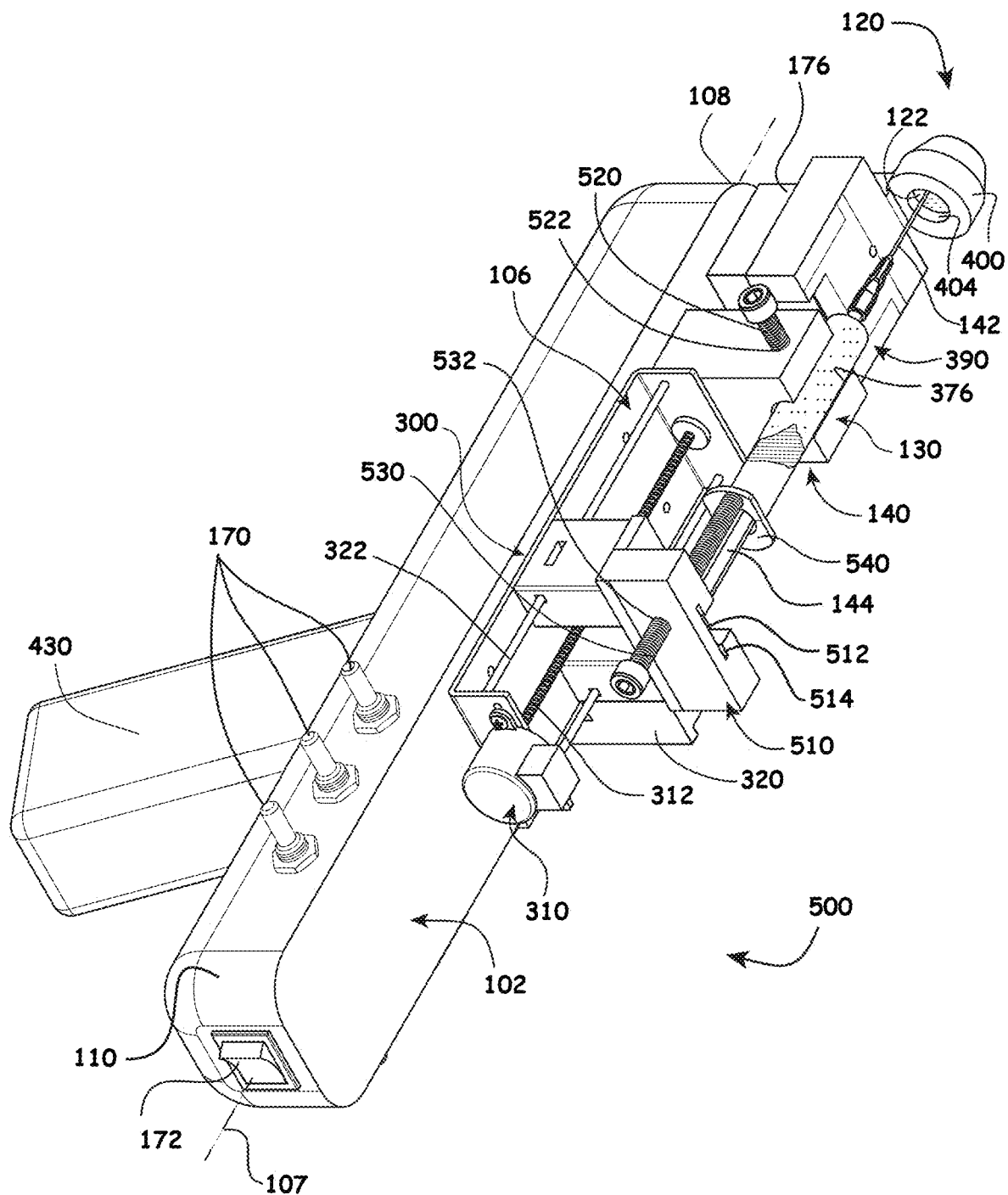
FIGS. 17A & 17B are simplified respective two different pictorial illustrations of a handheld assembled MPAI having a single motor, constructed and operative in accordance with another embodiment of the invention and showing the MPAI in a first operative orientation.
Figure 17B:
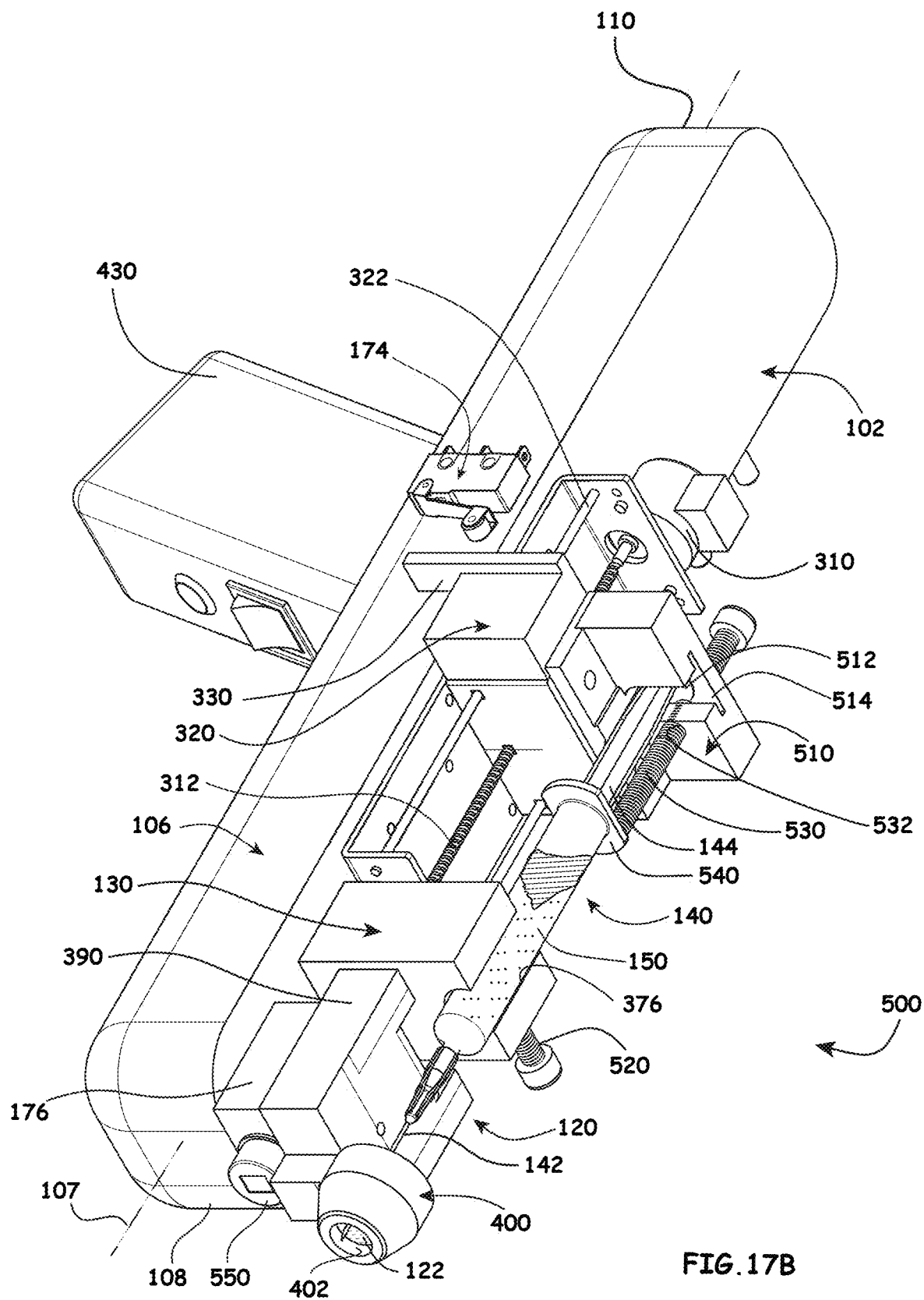

Reference is now made to FIGS. 17A & 17B, which are simplified respective two different pictorial illustrations of a handheld assembled MPAI 500 having a single motor, constructed and operative in accordance with another embodiment of the invention and showing the MPAI 500 in a first operative orientation.

The MPAI 500 in accordance to another embodiment of the present invention is similar in most respects to MPAI 100, illustrated and described with reference to FIGS. 1A-16D. It is a particular feature of an embodiment of the present invention that the MPAI 500 in accordance with another embodiment of the present invention includes a single electrical motor 310, which is operative both for actuating the repetitive reciprocating motion of the needle 142 to deposit medicament 122 from cartridge 120 in various depths within the injection site and for injecting the medicament 150 contained within the syringe 140 via the needle 142. Like components are numerated with like reference numerals hereinbelow.

A single carriage assembly 106 is fixedly attached onto the base unit 102, generally at an intermediate location thereof. The second driven element 320 is adapted to be axially displaceable relative to the second support element 300 of the carriage assembly 106 and thus relative to the base unit 102 upon actuation of the single electrical motor 310.

The syringe holder element 130 is preferably fixedly attached to base unit 102 and disposed forwardly to the carriage assembly 106. A plunger rod retainer 510 is fixedly coupled to the second driven element 320, and configured to be displaced axially along with the second driven element 320 upon actuation of the second motor 310.

The syringe 140 is at least partially selectably slidably received within the syringe holder element 130, such that a portion of the syringe barrel is received within opening 376.

It is particularly seen that a flange 512 of the plunger rod 144 is fixedly retained within groove 514 of the plunger rod retainer 510.

It is a particular feature of an embodiment of the present invention that the syringe 140 is initially slidably received through the syringe holder element 130, and therefore displaceable relative thereto in storage operative orientation. A screw 520 is received into a bore 522 formed in the syringe holder element 130 and in this storage operative orientation the screw 520 is not tightened against the barrel of the syringe 140, thereby allowing free axial displacement of the syringe 140 relative to the syringe holder element 130.

A stopper 530 is received through an opening 532 formed in the plunger rod retainer 510. The stopper 530 extends through the plunger rod retainer 510 and is supported against a flange 540 of the syringe 140 in this operative orientation.

It is a particular feature of an embodiment of the present invention that in this storage operative orientation when the stopper 530 is supported against the flange 540 of the syringe 140, the plunger rod 144, the syringe 140 and the needle 142 all move axially together as a single unit upon actuation of motor 310 and thus prevent relative movement of the plunger rod 144 and the syringe 140, thereby preventing inadvertent ejection of medicament 150 from the syringe 140 during the reciprocating motion of the needle 142, in accordance to the algorithm operating the MPAI 500, which is similar to the algorithm operating the MPAI 100, as illustrated and described in detail with reference to FIGS. 15-16D.

It is specifically seen in FIGS. 17A & 17B that the cartridge 120 is fixedly attached to the cartridge holder 176 of the base unit 102 or to the base unit 102 directly, adjacent the forward end 108 thereof. The medicament reservoir 400 preferably protrudes forwardly from the forward end 108 of the base unit 102. The syringe holder element 130 is preferably disposed between the cartridge 120 and the second carriage assembly 106 in accordance with an embodiment of the present invention.

It is a particular feature of an embodiment of the present invention that the syringe 140 protrudes forwardly from the syringe holding element 130, such that the needle 142 thereof is configured to be received into the inner volume of the medicament reservoir 400 of cartridge 120 through opening 404 thereof.

It is seen in FIGS. 17A & 17B that in accordance with one embodiment of the present invention, the cartridge 120 as illustrated in FIGS. 7A-7C is used. Alternatively, the cartridge 120 as illustrated in FIGS. 8A-8C may alternatively be used, so that the needle 142 penetrates the seal element 410 covering opening 404 to be partially received within the inner volume of the medicament reservoir 400.

It is a further particular feature of an embodiment of the present invention, as specifically seen in FIG. 17B, that the second engagement wall 330 of the second driven element 320 is adapted to be engageable with switch 174 in order to provide indication of a particular position of the plunger rod retainer 510 relative to the medicament reservoir 400 of the cartridge 120.

It is noted that the switch 174 is particularly operative for providing an indication of when the second carriage assembly 106 returned to initial storage position.

The MPAI 500 is illustrated in FIGS. 17A & 17B in storage operative orientation, in which the needle 142 is protected and the forward end thereof is concealed within the inner volume of the medicament reservoir 400 of the cartridge 120, such that the forward protrusion length of the needle 142 from the medicament reservoir 400 is defined as L0.

It is a particular feature of an embodiment of the present invention that the forward end of the needle 142 protrudes into a material disposed within the medicament reservoir 400, whereas the material is absorbed with medicament, which is in turn deposited onto the outer surface of the needle 142.

It is particularly seen in FIGS. 17A & 17B that the second carriage assembly 106 is disposed at its initial storage operative orientation where the plunger rod retainer 510 is not yet displaced relative to the base unit 102, so that the forward end of the needle 142 is disposed within the medicament reservoir 400 of the cartridge 120 and is protected therewithin.

It is a particular feature of an embodiment of the present invention that a motion sensor 550, as particularly seen in FIG. 17B is coupled to the forward end of the cartridge 120 to indicate movement of the cartridge 120 from the injection site during operation of the MPAI 500. Particular use and advantage of the motion sensor 550 coupled to cartridge 120 is described in detail with reference to FIGS. 12A & 12B.

Figure 18A:
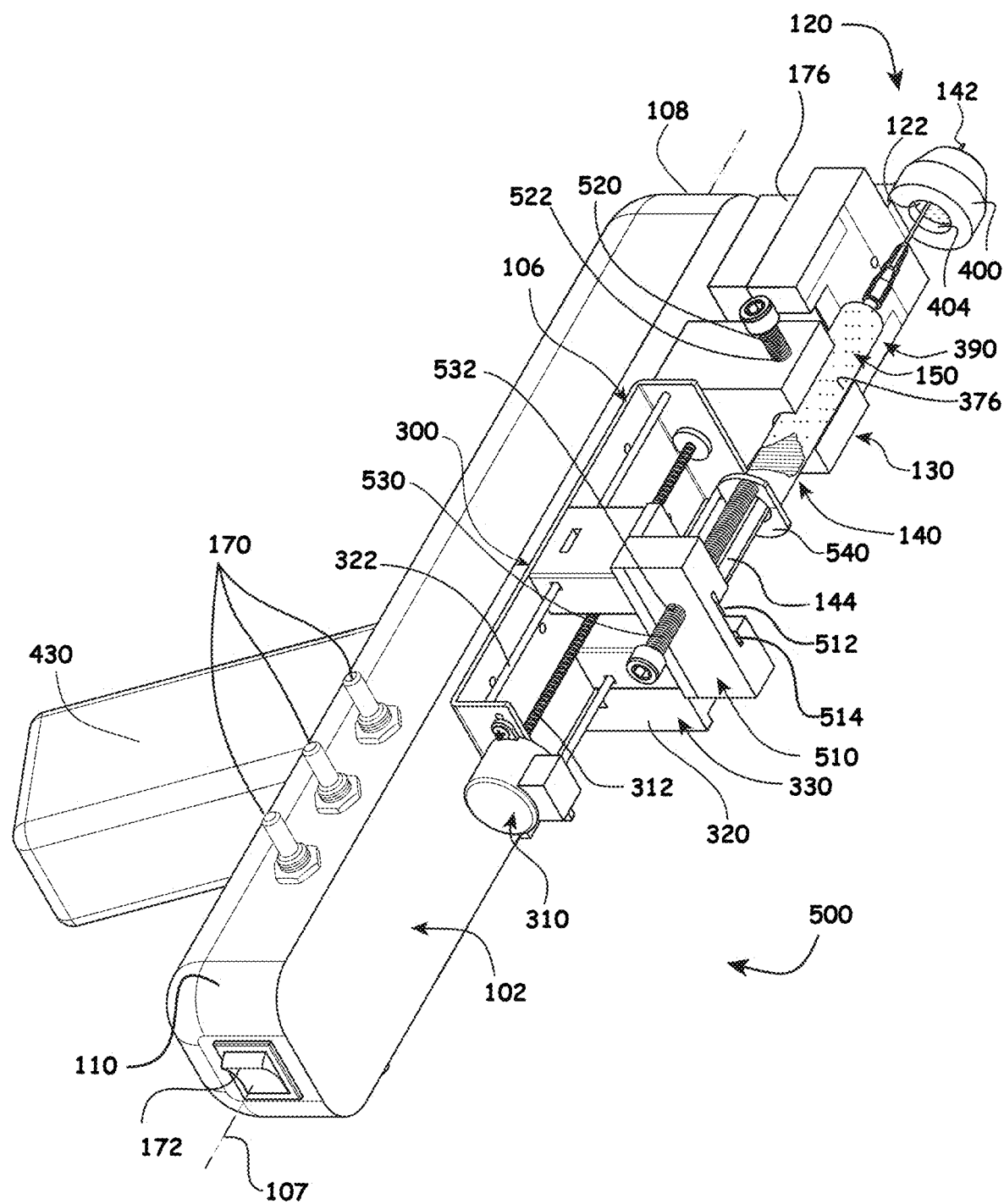
FIGS. 18A & 18B are simplified two different pictorial illustrations of the handheld assembled MPAI of FIGS. 17A & 17B, showing the MPAI in a second operative orientation.
Figure 18B:
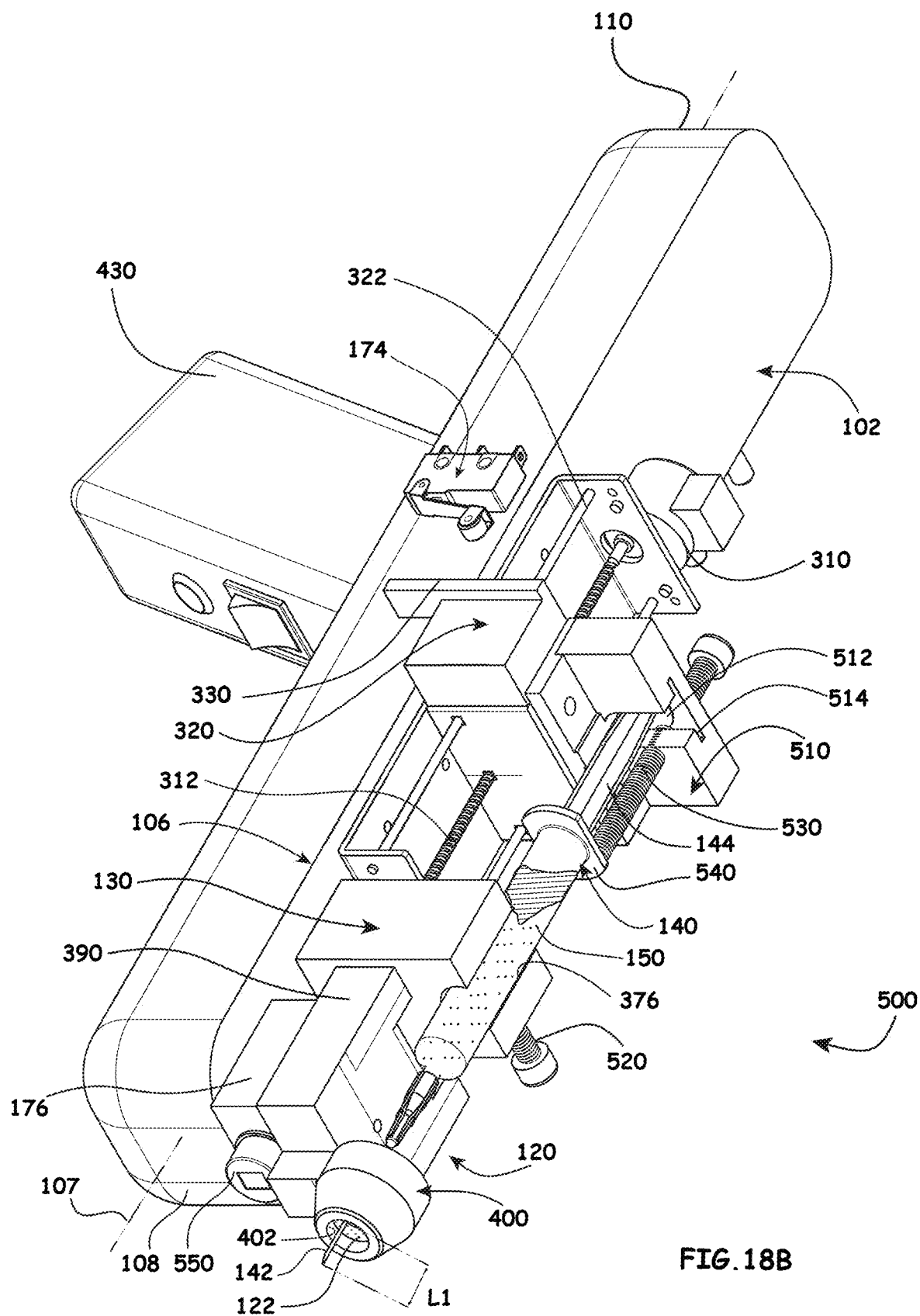

Reference is now made to FIGS. 18A & 18B, which are simplified two different pictorial illustrations of the hand-held assembled MPAI 500 of FIGS. 17A & 17B, showing the MPAI 500 in a second operative orientation.

It is appreciated that all spatial relationships between the various components of the MPAI 500 remain the same as described hereinabove and illustrated in FIGS. 17A &17B, besides the following:

The MPAI 500 is illustrated in FIGS. 18A & 18B in a first stage of reciprocating motion operative orientation, in which the needle 142 protrudes forwardly from the medicament reservoir 400 of the cartridge 120 to a first longitudinal extent L1, thus the needle 142 protrudes into the injection site under the skin of the patient to an initial depth L1.

It is a particular feature of an embodiment of the present invention that the medicament from the medicament cartridge 400 of cartridge 120 that is deposited onto the outer surface of needle 142 is delivered at depth L1 at the injection site and is deposited there in a tattoo-like manner.

It is particularly seen in FIGS. 18A & 18B that the carriage assembly 106 is disposed at its first stage of reciprocating motion operative orientation where the driven unit 320, along with the plunger rod retainer 510, the syringe 140 and the needle 142 are together forwardly axially displaced relative to the base unit 102 to a longitudinal extent L1, so that the forward end of the needle 142 protrudes forwardly from the forward end of medicament reservoir 400 of cartridge 120 to a distance of L1.

It is a particular feature of an embodiment of the present invention that the first stage of reciprocating motion is a repetitive stage, in which multiple reciprocations of the needle 142 to a depth of L1 under the skin of the patient are typically performed in order to deposit a sufficient amount of medicament from the medicament reservoir 400 of the cartridge 120 into depth L1 at the injection site.

Upon receipt of an appropriate signal from the controller of the MPAI 500, the motor 310 is actuated and is operative to drive the second lead screw 312, which causes displacement of the second driven element 320 and thus the displacement of the plunger rod retainer 510 therealong. The plunger rod 144 is fixedly retained within the plunger rod retainer 510 and relative displacement between the plunger rod 144 and the syringe 140 is prevented due to engagement of stopper 530 both with the plunger rod retainer 510 and with flange 540 of the syringe 140. Therefore, the syringe 140 and needle 142 are axially displaced forwardly in this operative orientation together with the plunger rod retainer 510.

It is a particular feature of an embodiment of the present invention that the penetration depth of the needle 142 is controlled by the motor 310, thereby increasing the control and accuracy of needle depth penetration. The needle 142 is preferably displaced during its reciprocating motion according to specific algorithms related to the timing of a sequence of incremental increases in needle penetration depth, as described in detail hereinbelow. The specific algorithms can be selected by the user by means of mechanical or digital inputs, such as user input elements 170, for example, as described in detail hereinabove.

In accordance with an algorithm controlling the operation of the MPAI 500, as described in detail hereinabove, during each reciprocation of the needle 142, the plunger rod retainer 510 is displaced axially forwardly relative to base unit 102 to distance L1 and returns axially rearwardly relative to the base unit 102 to distance L0, as specifically illustrated in FIGS. 17A & 17B.

Figure 19A:
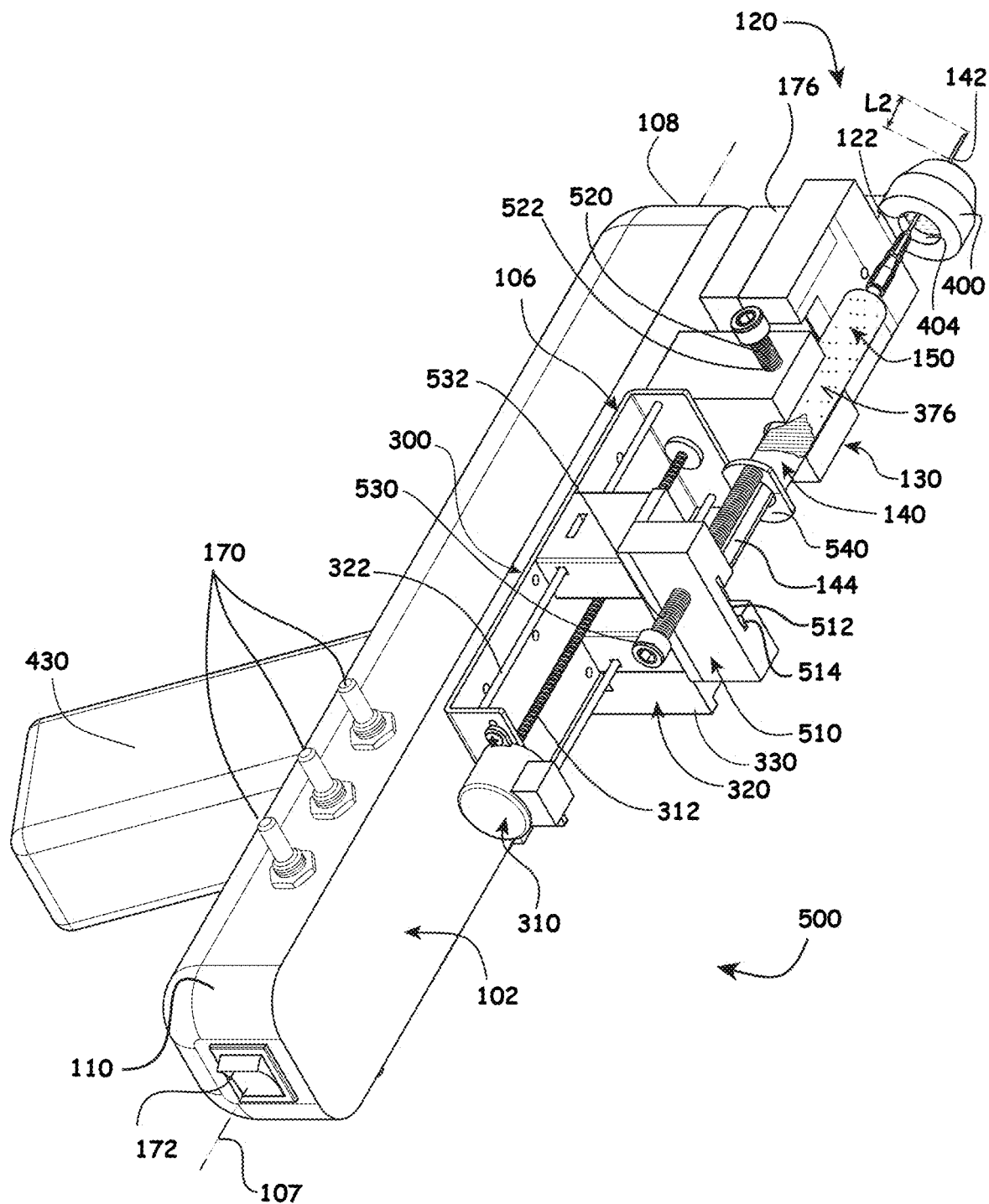
FIGS. 19A & 19B are simplified two different pictorial illustrations of the handheld assembled MPAI of FIGS. 17A & 17B, showing the MPAI in a third operative orientation.
Figure 19B:
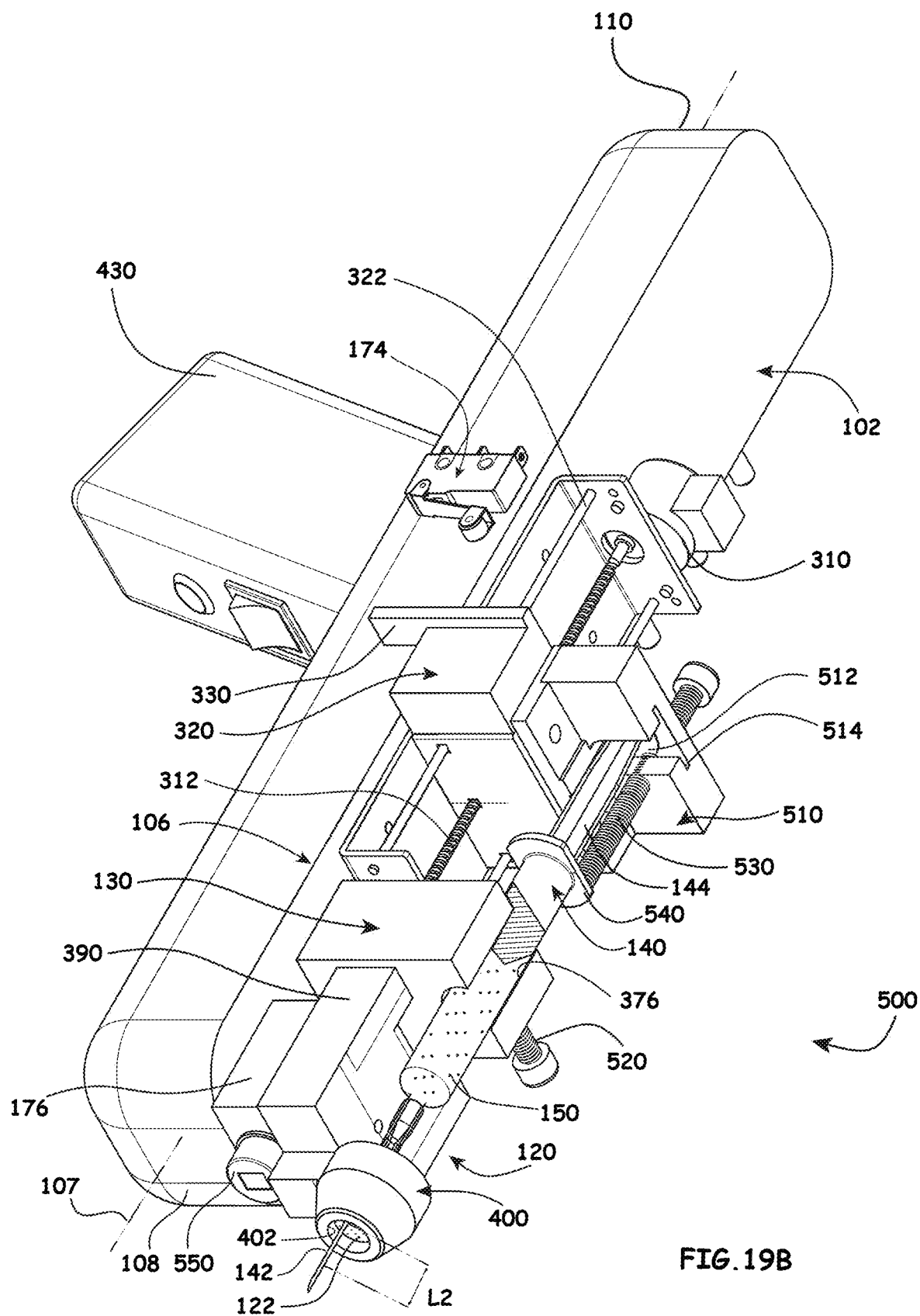

Reference is now made to FIGS. 19A & 19B, which are simplified two different pictorial illustrations of the handheld assembled MPAI 500 of FIGS. 17A & 17B, showing the MPAI 500 in a third operative orientation.

It is appreciated that all spatial relationships between the various components of the MPAI 500 remain the same as described hereinabove and illustrated in FIGS. 18A & 18B, besides the following:

The MPAI 500 is illustrated in FIGS. 19A & 19B in a second stage of reciprocating motion operative orientation, in which the needle 142 protrudes forwardly from the medicament reservoir 400 of the cartridge 120 to a second longitudinal extent L2, generally greater than the first longitudinal extent L1, thus the needle 142 protrudes into the injection site under the skin of the patient to depth L2, greater than depth L1.

It is a particular feature of an embodiment of the present invention that the medicament from the medicament cartridge 400 of cartridge 120 that is deposited onto the outer surface of needle 142 is delivered at depth L2 at the injection site and is deposited there in a tattoo-like manner.

It is particularly seen in FIGS. 19A & 19B that the carriage assembly 106 is disposed at its second stage of reciprocating motion operative orientation where the plunger rod retainer 510 is further forwardly axially displaced relative to the base unit 102 to a longitudinal extent L2, generally greater than longitudinal extent L1, so that the forward end of the needle 142 protrudes more forwardly from the forward end of medicament reservoir 400 of cartridge 120 to a distance of L2.

Upon receipt of an appropriate signal from the controller of the MPAI 500, the motor 310 is actuated and is operative to drive the second lead screw 312, which causes displacement of the second driven element 320 and thus the displacement of the plunger rod retainer 510 therealong. The plunger rod 144 is fixedly retained within the plunger rod retainer 510 and relative displacement between the plunger rod 144 and the syringe 140 is prevented due to engagement of stopper 530 both with the plunger rod retainer 510 and with flange 540 of the syringe 140. Therefore, the syringe 140 and needle 142 are further axially displaced forwardly in this operative orientation together with the plunger rod retainer 510.

It is a particular feature of an embodiment of the present invention that the second stage of reciprocating motion is a repetitive stage, in which multiple reciprocations of the needle 142 to a depth of L2 under the skin of the patient are typically performed in order to deposit a sufficient amount of medicament from the medicament reservoir 400 of the cartridge 120 into depth L2 at the injection site.

In accordance with an algorithm controlling the operation of the MPAI 100, as described in detail hereinbelow, during each reciprocation of the needle 142, the syringe holder element 130 is displaced axially forwardly relative to base unit 102 to distance L2 and returns axially rearwardly relative to the base unit 102 to distance L0, as specifically illustrated in FIGS. 17A & 17B.

It is noted that the first stage of reciprocating motion and the second stage of reciprocating motion are defined as the first mode of operation of the MPAI 100. It is a particular feature of an embodiment of the present invention that in the first mode of operation of the MPAI 500 the plunger rod 144 is static relative to the syringe 140, thereby preventing ejection of the medicament 150 therefrom and the syringe 140 is axially displaceable relative to the base unit 102, thereby providing for administration of medicament 122 from the cartridge 120 at various depths under the skin of the patient by means of depositing the needle into the medicament reservoir 400 of the cartridge 120, which is filled with medicament 122.

It is a particular feature of an embodiment of the present invention that motion sensor 550 is incorporated into the MPAI 500 and is generally disposed on the forward end of the cartridge holder 176 of the forward end of the medicament reservoir 400 of the cartridge 120. It is noted that the motion sensor is configured to be activated upon initiation of a reciprocation algorithm. Motion of the patient relative to the MPAI 500 detected by the sensor during a reciprocation sequence triggers a pause in the reciprocation sequence.

Figure 20A:
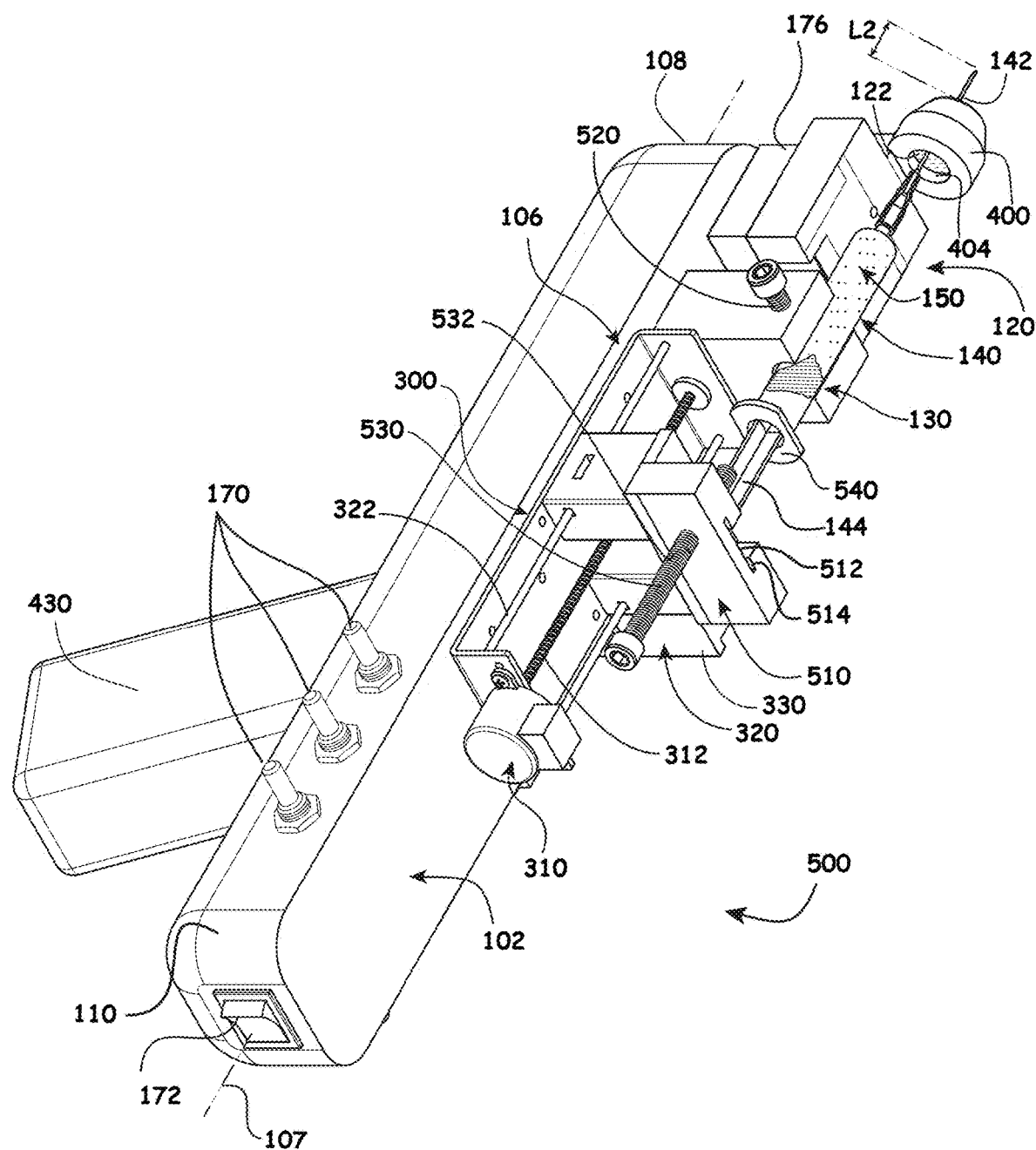
FIGS. 20A & 20B are simplified two different pictorial illustrations of the handheld assembled MPAI of FIGS. 17A & 17B, showing the MPAI in a fourth operative orientation.
Figure 20B:
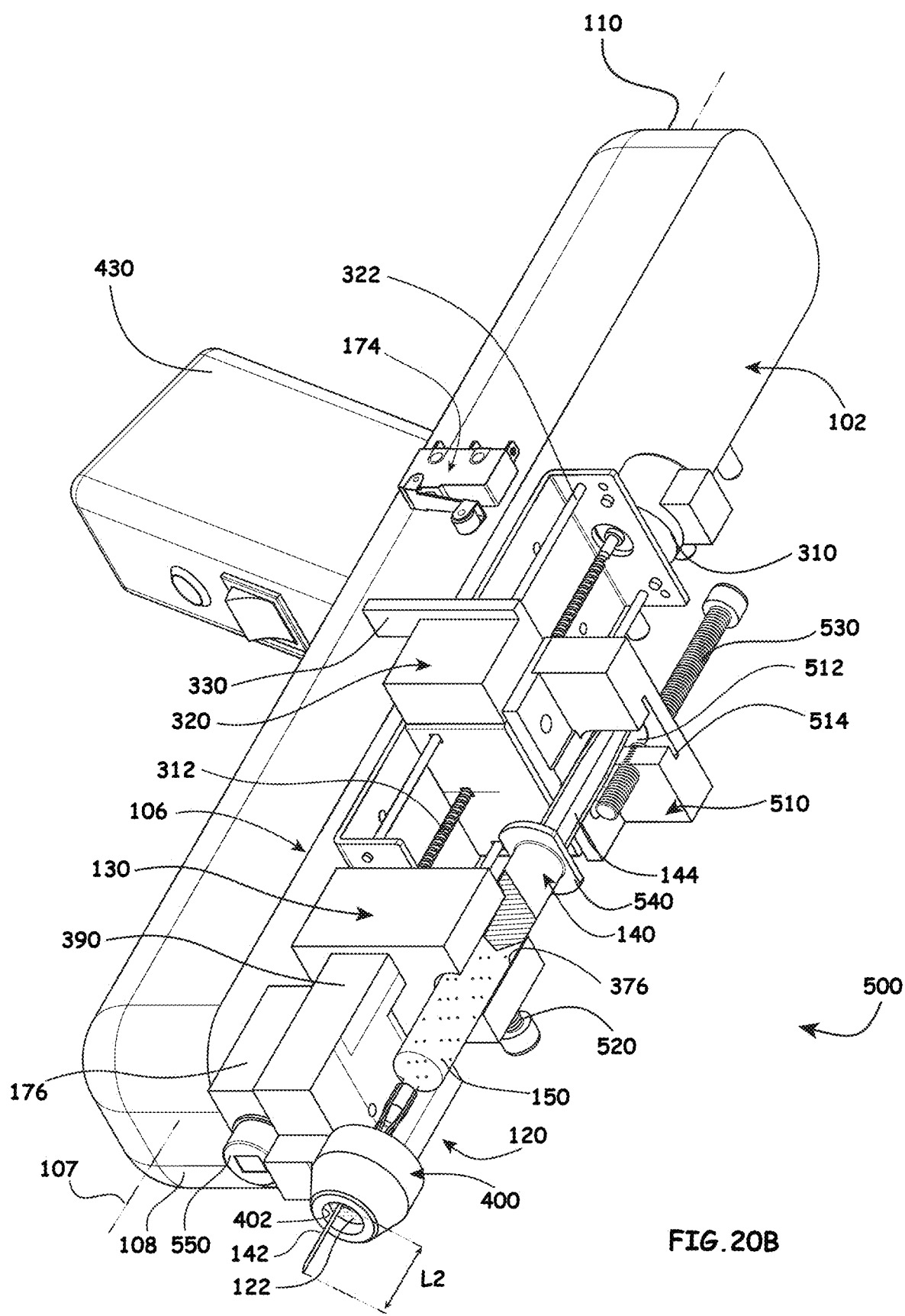

Reference is now made to FIGS. 20A & 20B, which are simplified two different pictorial illustrations of the handheld assembled MPAI 500 of FIGS. 17A & 17B, showing the MPAI 500 in a fourth operative orientation.

It is appreciated that all spatial relationships between the various components of the MPAI 500 remain the same as described hereinabove and illustrated in FIGS. 19A & 19B, besides the following:

The MPAI 500 is illustrated in FIGS. 20A & 20B in an injection initiation operative orientation, in which the needle 142 still protrudes forwardly from the medicament reservoir 400 of the cartridge 120 to a second longitudinal extent L2 and the stopper 530 is retracted axially rearwardly and disengages from the flange 540 of the syringe 140, such that a gap now exists between the forward end of the stopper 530 and the flange 540 of the syringe 140, thereby permitting relative displacement of the plunger rod 144 relative to the syringe 140 to effect ejection of medicament 150 therefrom.

It is additionally seen in FIGS. 20A & 20B that screw 520 is tightened to securely hold the syringe 140 within the syringe holding element 130 and prevents its further axial displacement relative to cartridge 120.

It is particularly seen in FIGS. 20A & 20B that the carriage assembly 106 is disposed at its injection initiation operative orientation where the plunger rod retainer 510 is allowed to be slightly axially forwardly displaced relative to the base unit 102, so that the plunger rod 144 is displaced relative to the syringe 140.

It is further particularly seen in FIGS. 20A & 20B that the syringe 140 now remains static relative to the base unit 102 and relative to the cartridge 120 due to tightening of the syringe 140 to the syringe holding element 130 by means of screw 520. Thus, the forward end of the needle 142 protrudes forwardly from the forward end of medicament reservoir 400 of cartridge 120 to a distance of L2.

Figure 21A:
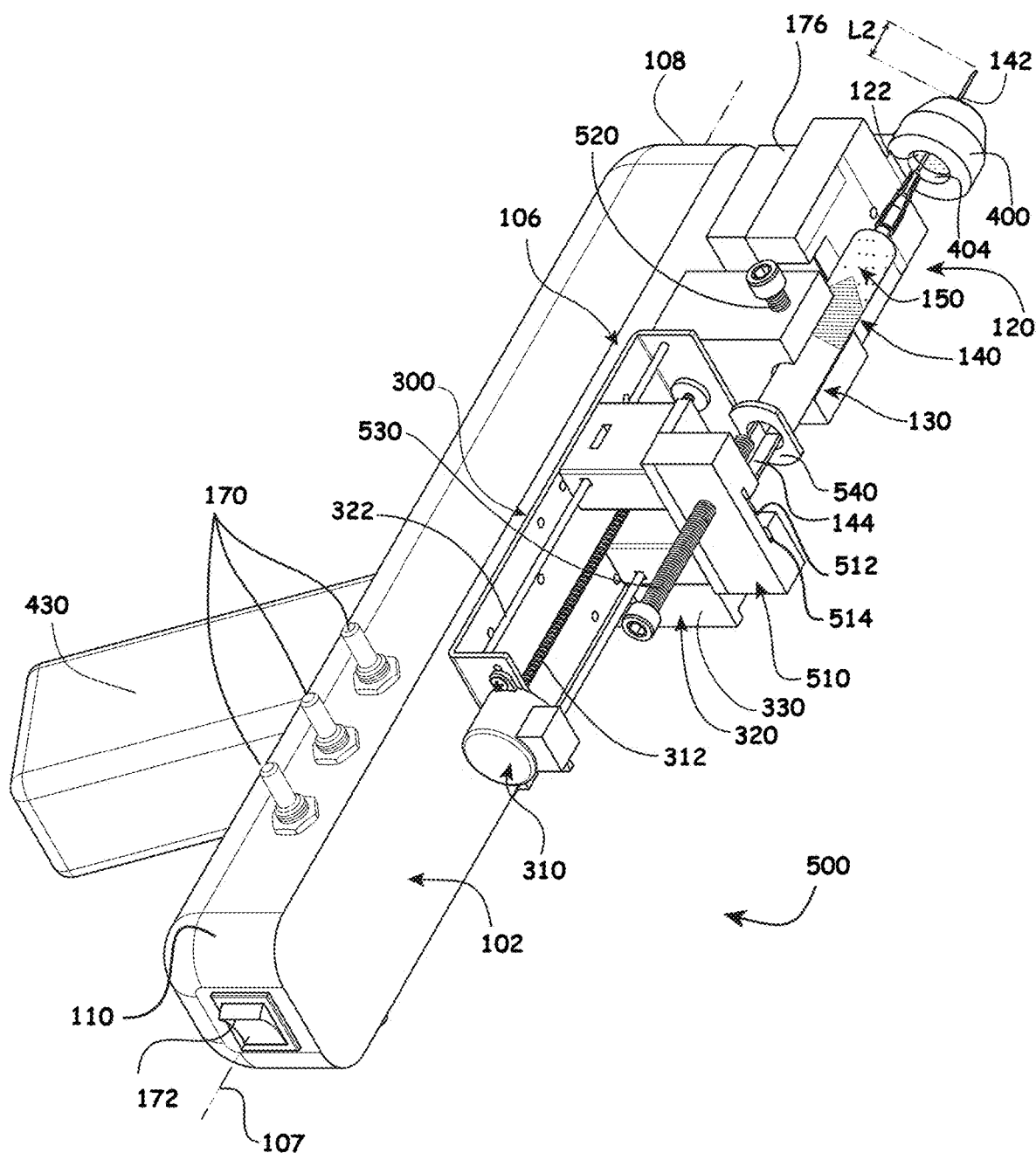
FIGS. 21A & 21B are simplified two different pictorial illustrations of the handheld assembled MPAI of FIGS. 17A & 17B, showing the MPAI in a fifth operative orientation.
Figure 21B:
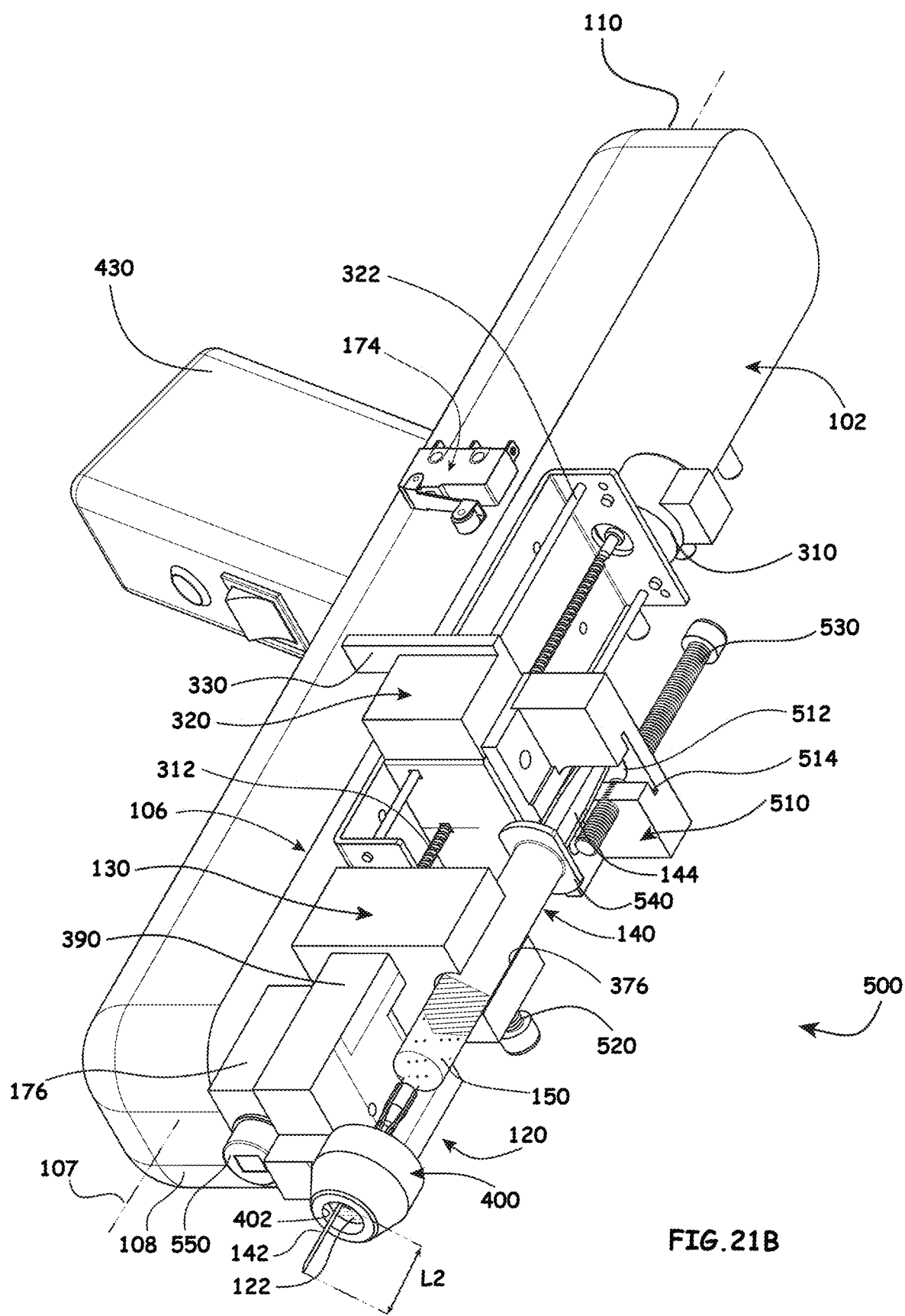

Reference is now made to FIGS. 21A & 21B, which are simplified two different pictorial illustrations of the handheld assembled MPAI 500 of FIGS. 17A & 17B, showing the MPAI 500 in a fifth operative orientation.

It is appreciated that all spatial relationships between the various components of the MPAI 500 remain the same as described hereinabove and illustrated in FIGS. 20A & 20B, besides the following:

The MPAI 500 is illustrated in FIGS. 21A & 21B in an injection operative orientation, in which the needle 142 still protrudes forwardly from the medicament reservoir 400 of the cartridge 120 to a second longitudinal extent L2 and the plunger rod retainer 510 is axially displaced forwardly relative to the base unit 102, thereby axially forwardly displacing the plunger rod 144 relative to the syringe 140, causing ejection of the medicament 150 from the syringe 140 via the needle 142 and into the injection site. The medicament 150 is injected at a depth L2 under the skin of the patient, at which the needle reciprocations have stopped in accordance with the instructions provided to the controller by the algorithm controlling the operation of the MPAI 500.

It is particularly seen in FIGS. 21A & 21B that the carriage assembly 106 is disposed at its injection operative orientation where the plunger rod retainer 510 is further axially forwardly displaced relative to the base unit 102, so that the plunger rod 144 is displaced relative to the syringe 140.

It is further particularly seen in FIGS. 21A & 21B that the syringe 140 and needle 142 remain at its second stage of reciprocating motion operative orientation where the forward end of the needle 142 protrudes forwardly from the forward end of medicament reservoir 400 of cartridge 120 to a distance of L2.

It is noted that the injection initiation operative orientation and the injection operative orientation are defined as the second mode of operation of the MPAI 500. It is a particular feature of an embodiment of the present invention that in the second mode of operation of the MPAI 500, the syringe 140 is static with respect to the base unit 102 and the driven unit 320 of the carriage assembly 106 is axially movable relative to the base unit 102. As a result, the syringe 140 and the needle 142 are static relative to the cartridge 120, thereby preventing depositing of medicament 122 from the cartridge 120 into the skin and the plunger rod 144 is axially movable relative to the syringe 140, thereby providing for ejection of the medicament 150 from the syringe 140 via the needle 142 and into the injection site under the skin of the patient, at the desired depth L2, as provided by the algorithm controlling the operation of the MPAI 500.

It is noted that all of the alternative embodiments related to the various components of the MPAI 100 and the method of use thereof are applicable to the same extent in MPAI 500.

Figure 22A:
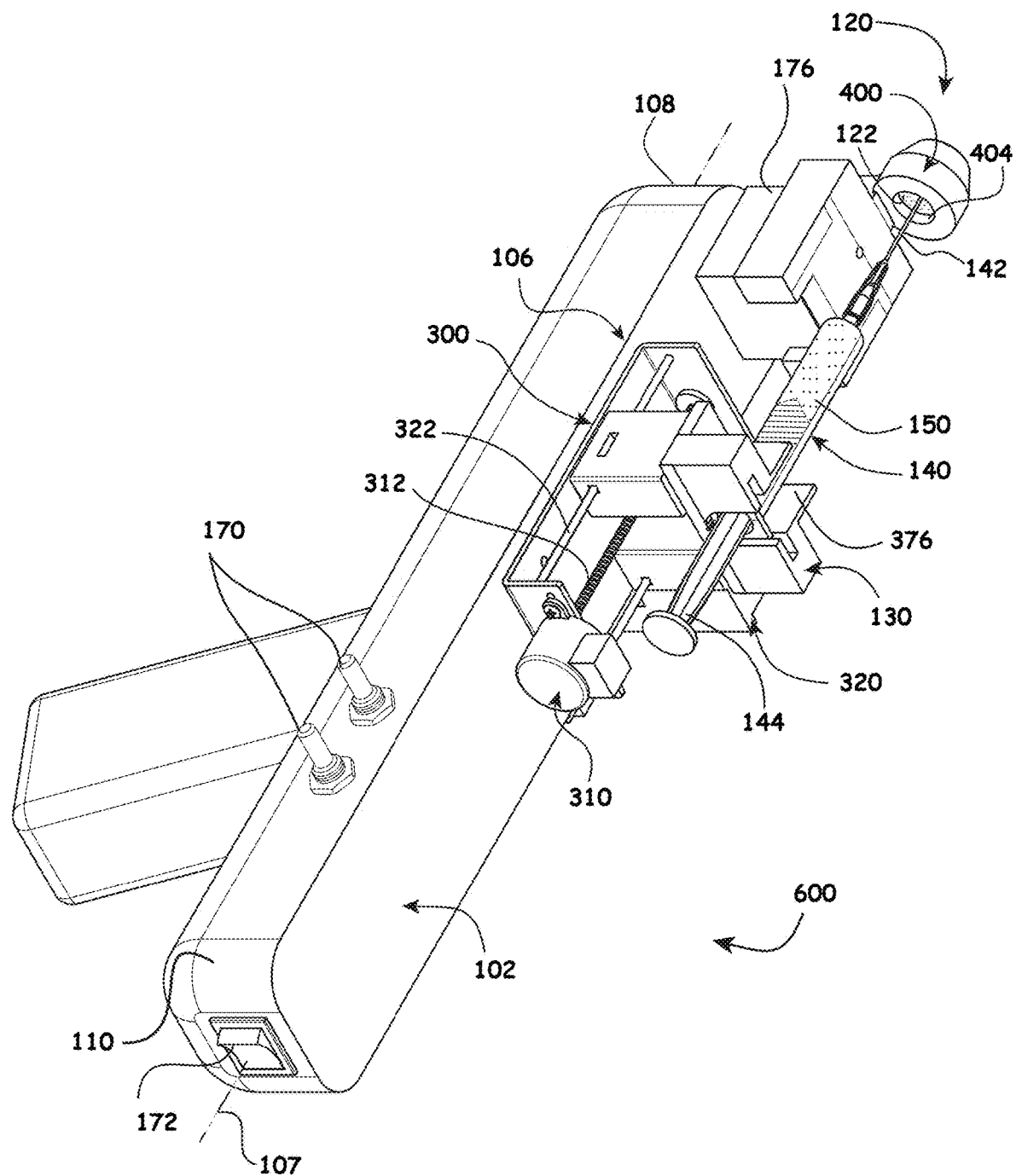
FIGS. 22A & 22B are simplified two different pictorial illustrations of a handheld assembled MPAI with a manually operated plunger rod, constructed and operative in accordance with still another embodiment of the invention and showing the MPAI in a first operative orientation.
Figure 22B:
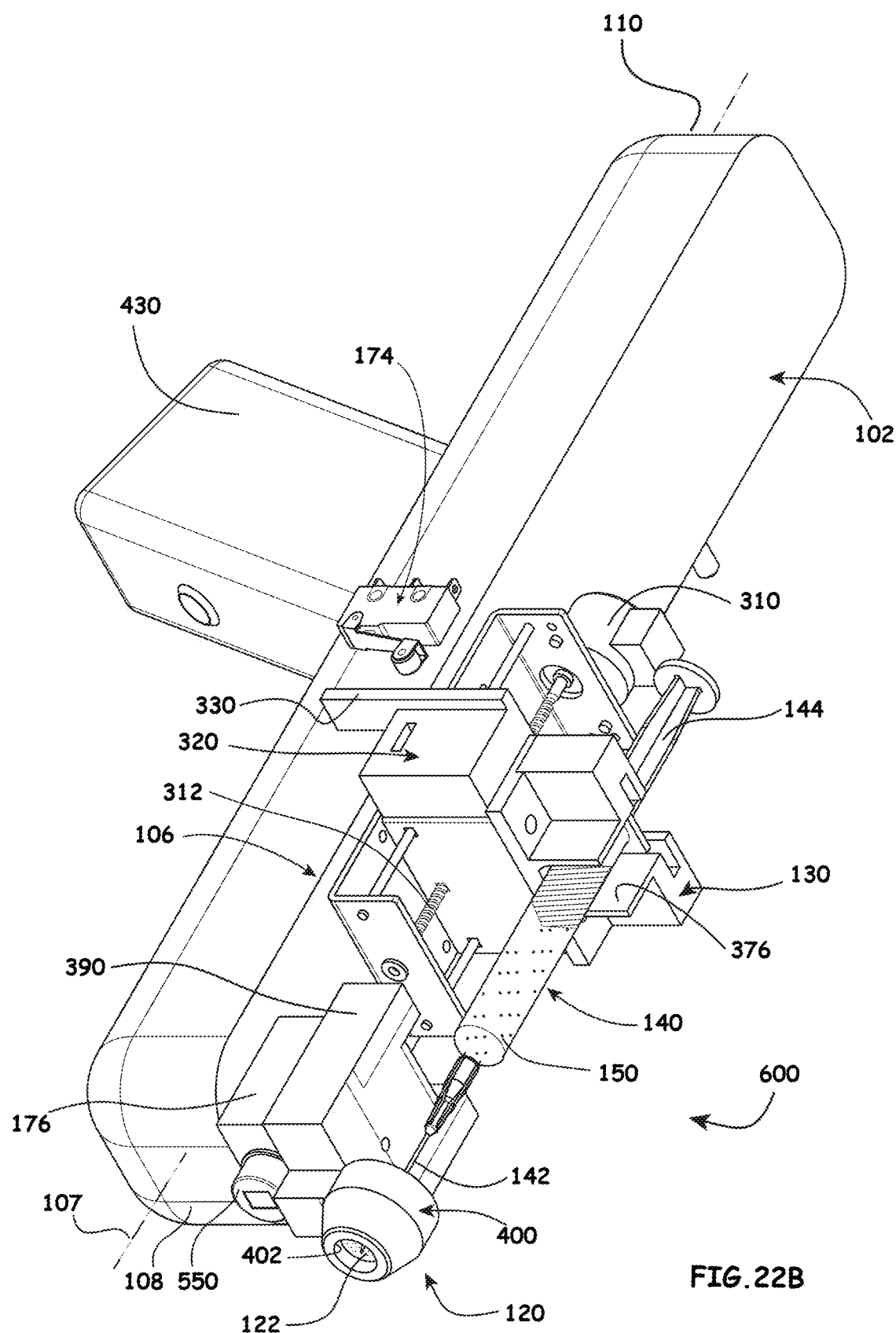

Reference is now made to FIGS. 22A & 22B, which are simplified two different pictorial illustrations of a handheld assembled MPAI with a manually operated plunger rod, constructed and operative in accordance with still another embodiment of the invention and showing the MPAI in a first operative orientation.

The MPAI 600 in accordance with another embodiment of the present invention is similar in most respects to MPAI 500, illustrated and described with reference to FIGS. 17A-21B. It is a particular feature of an embodiment of the present invention that the MPAI 600 in accordance with another embodiment of the present invention includes a single electrical motor 310, which is operative for actuating the repetitive reciprocating motion of the needle 142 to deposit medicament 122 from cartridge 120 in various depths within the injection site and the plunger rod 144 is operable manually by the user for injecting the medicament 150 contained within the syringe 140 via the needle 142. Like components are numerated with like reference numerals hereinbelow.

A single carriage assembly 106 is fixedly attached onto the base unit 102, generally at an intermediate location thereof. The second driven element 320 is adapted to be axially displaceable relative to the second support element 300 of the carriage assembly 106 and thus relative to the base unit 102 upon actuation of the single electrical motor 310.

The syringe holder element 130 is preferably fixedly attached to the driven element 320 and is adapted to fixedly retain the flange of the syringe 140 therewithin. The plunger rod 144 is partially slidably received within the syringe 140 for manual manipulation thereof by the user.

It is specifically seen in FIGS. 22A & 22B that the cartridge 120 is fixedly attached to the cartridge holder 176 of the base unit 102 or to the base unit 102 directly, adjacent the forward end 108 thereof. The medicament reservoir 400 preferably protrudes forwardly from the forward end 108 of the base unit 102.

It is a particular feature of an embodiment of the present invention that the syringe 140 protrudes forwardly from the syringe holding element 130, such that the needle 142 thereof is configured to be received into the inner volume of the medicament reservoir 400 of cartridge 120 through opening 404 thereof.

It is seen in FIGS. 22A & 22B that in accordance with one embodiment of the present invention, the cartridge 120 as illustrated in FIGS. 7A-7C is used. Alternatively, the cartridge 120 as illustrated in FIGS. 8A-8C may alternatively be used, so that the needle 142 penetrates the seal element 410 covering opening 404 to be partially received within the inner volume of the medicament reservoir 400.

It is a further particular feature of an embodiment of the present invention, as specifically seen in FIG. 22B, that the second engagement wall 330 of the second driven element 320 is adapted to be engageable with switch 174 in order to provide indication of a particular position of the syringe holding element 130 relative to the medicament reservoir 400 of the cartridge 120.

It is noted that the switch 174 is particularly operative for providing an indication of when the carriage assembly 106 returned to initial storage position.

The MPAI 600 is illustrated in FIGS. 22A & 22B in storage operative orientation, in which the needle 142 is protected and the forward end thereof is concealed within the inner volume of the medicament reservoir 400 of the cartridge 120, such that the forward protrusion length of the needle 142 from the medicament reservoir 400 is defined as L0.

It is a particular feature of an embodiment of the present invention that the forward end of the needle 142 protrudes into a material disposed within the medicament reservoir 400, whereas the material is absorbed with medicament, which is in turn deposited onto the outer surface of the needle 142.

It is particularly seen in FIGS. 22A & 22B that the carriage assembly 106 is disposed at its initial storage operative orientation where the syringe holding element 130 is not yet displaced relative to the base unit 102, so that the forward end of the needle 142 is disposed within the medicament reservoir 400 of the cartridge 120 and is protected therewithin.

It is a particular feature of an embodiment of the present invention that a motion sensor 550, as particularly seen in FIG. 22B is coupled to the forward end of the cartridge 120 to indicate movement of the cartridge 120 from the injection site during operation of the MPAI 600. Particular use and advantage of the motion sensor 550 coupled to cartridge 120 is described in detail with reference to FIGS. 12A & 12B.

Figure 23:
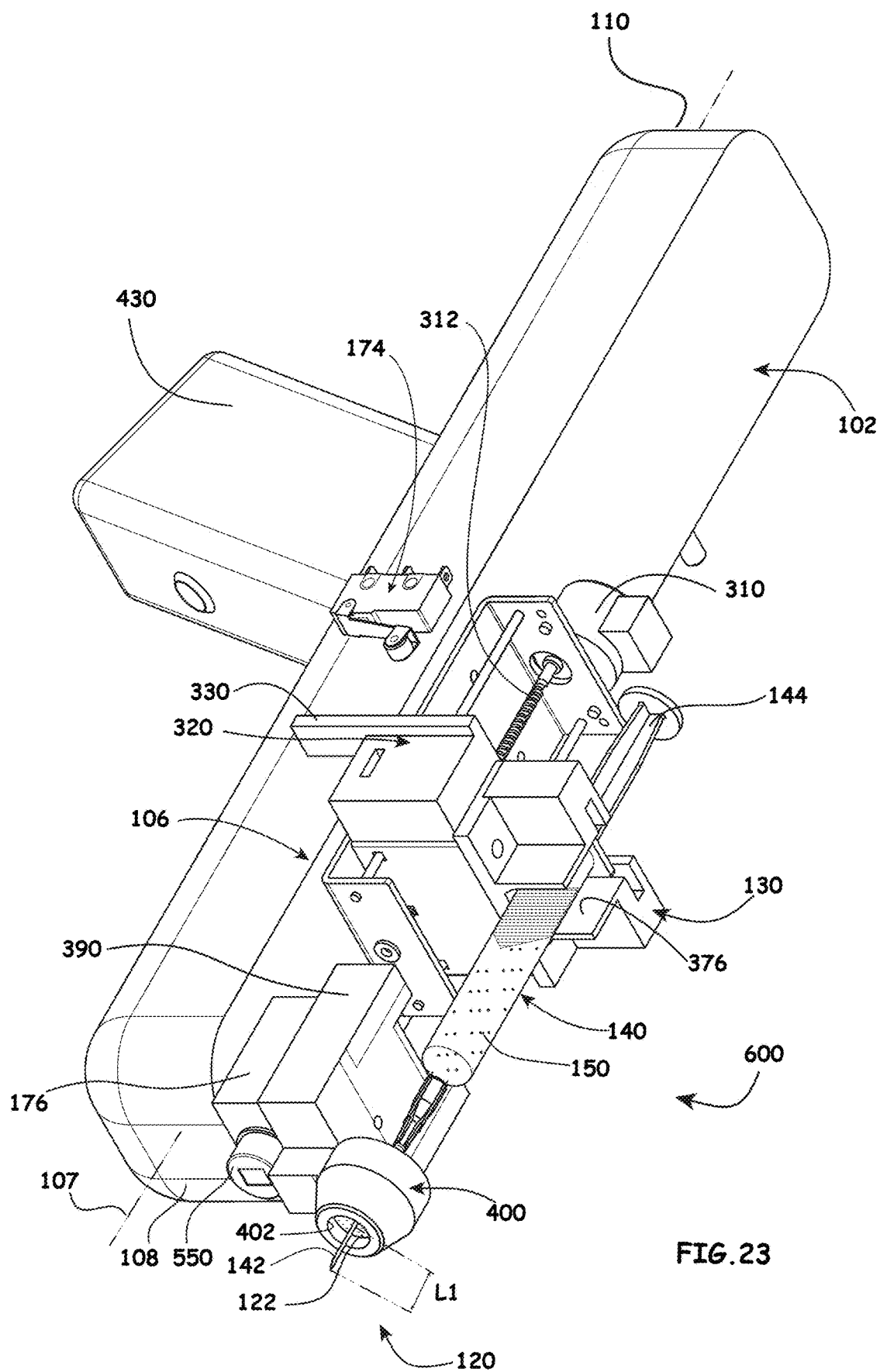
FIG. 23 is a simplified pictorial illustration of the handheld assembled MPAI of FIGS. 22A & 22B, showing the MPAI in a second operative orientation.

Reference is now made to FIG. 23, which is a simplified pictorial illustration of the handheld assembled MPAI 600 of FIGS. 22A & 22B, showing the MPAI 600 in a second operative orientation.

It is appreciated that all spatial relationships between the various components of the MPAI 600 remain the same as described hereinabove and illustrated in FIGS. 22A & 22B, besides the following:

The MPAI 600 is illustrated in FIG. 23 in a first stage of reciprocating motion operative orientation, in which the needle 142 protrudes forwardly from the medicament reservoir 400 of the cartridge 120 to a first longitudinal extent L1, thus the needle 142 protrudes into the injection site under the skin of the patient to an initial depth L1.

It is a particular feature of an embodiment of the present invention that the medicament from the medicament cartridge 400 of cartridge 120 that is deposited onto the outer surface of needle 142 is delivered at depth L1 at the injection site and is deposited there in a tattoo-like manner.

It is particularly seen in FIG. 23 that the carriage assembly 106 is disposed at its first stage of reciprocating motion operative orientation where the driven unit 320, along with the syringe holding element 130, the syringe 140 and the needle 142 are together forwardly axially displaced relative to the base unit 102 to a longitudinal extent L1, so that the forward end of the needle 142 protrudes forwardly from the forward end of medicament reservoir 400 of cartridge 120 to a distance of L1.

It is a particular feature of an embodiment of the present invention that the first stage of reciprocating motion is a repetitive stage, in which multiple reciprocations of the needle 142 to a depth of L1 under the skin of the patient are typically performed in order to deposit a sufficient amount of medicament from the medicament reservoir 400 of the cartridge 120 into depth L1 at the injection site.

Upon receipt of an appropriate signal from the controller of the MPAI 600, the motor 310 is actuated and is operative to drive the second lead screw 312, which causes displacement of the second driven element 320 and thus the displacement of the syringe holding element 130 therealong. The plunger rod 144 is freely axially displaceable relative to the syringe 140.

It is a particular feature of an embodiment of the present invention that the penetration depth of the needle 142 is controlled by the motor 310, thereby increasing the control and accuracy of needle depth penetration. The needle 142 is preferably displaced during its reciprocating motion according to specific algorithms related to the timing of a sequence of incremental increases in needle penetration depth, as described in detail hereinbelow. The specific algorithms can be selected by the user by means of mechanical or digital inputs, such as user input elements 170, for example, as described in detail hereinabove.

In accordance with an algorithm controlling the operation of the MPAI 600, as described in detail hereinabove, during each reciprocation of the needle 142, the syringe holding element 130 is displaced axially forwardly relative to base unit 102 to distance L1 and returns axially rearwardly relative to the base unit 102 to distance L0, as specifically illustrated in FIGS. 22A & 22B.

It is noted that all of the alternative embodiments related to the various components of the MPAI 100 and the method of use thereof are applicable to the same extent in MPAI 600.

Figure 24A:
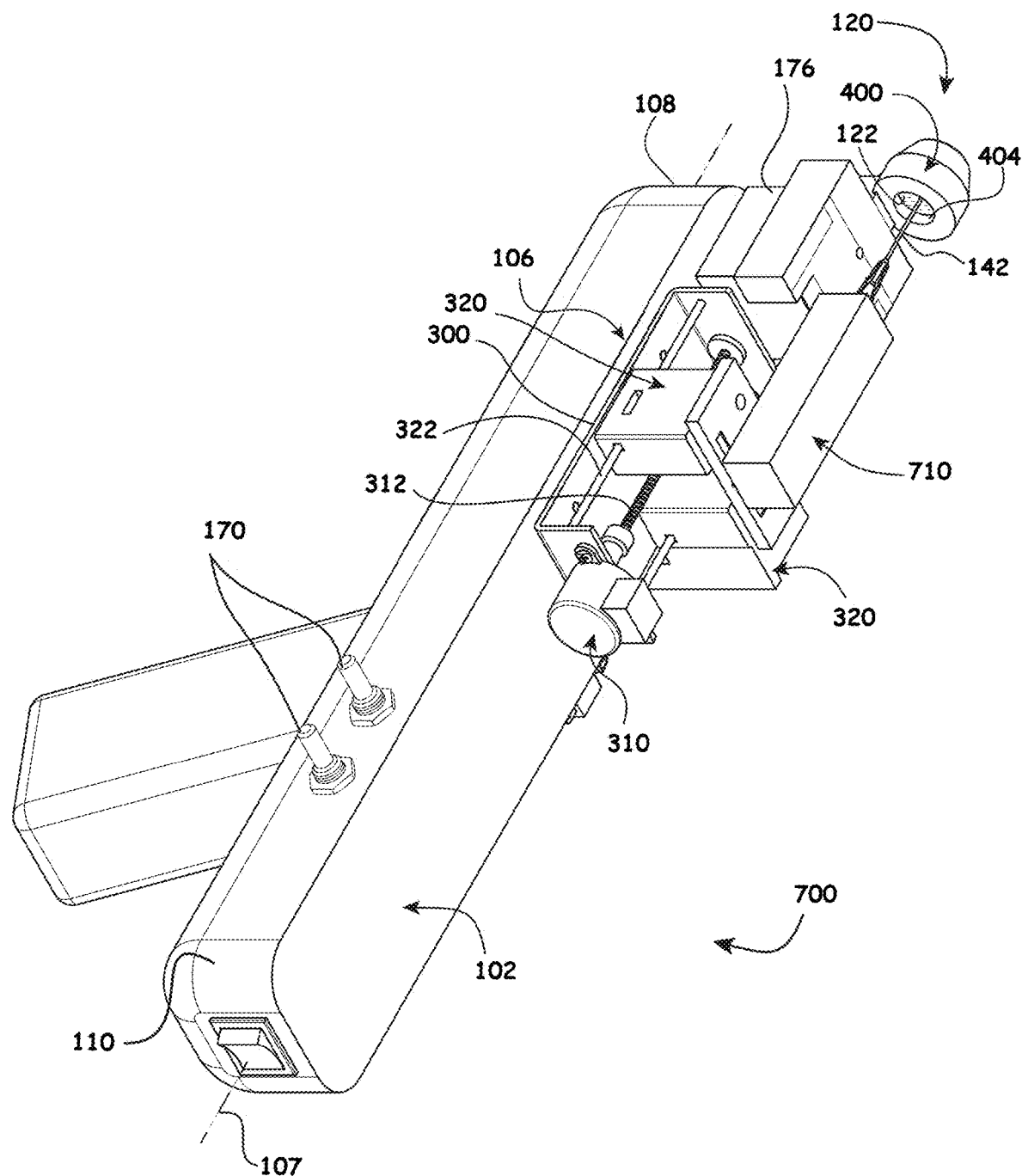
FIGS. 24A & 24B are simplified two different pictorial illustrations of a handheld assembled MPAI with a needle assembly only, constructed and operative in accordance with yet another embodiment of the invention and showing the MPAI in a first operative orientation.
Figure 24B:
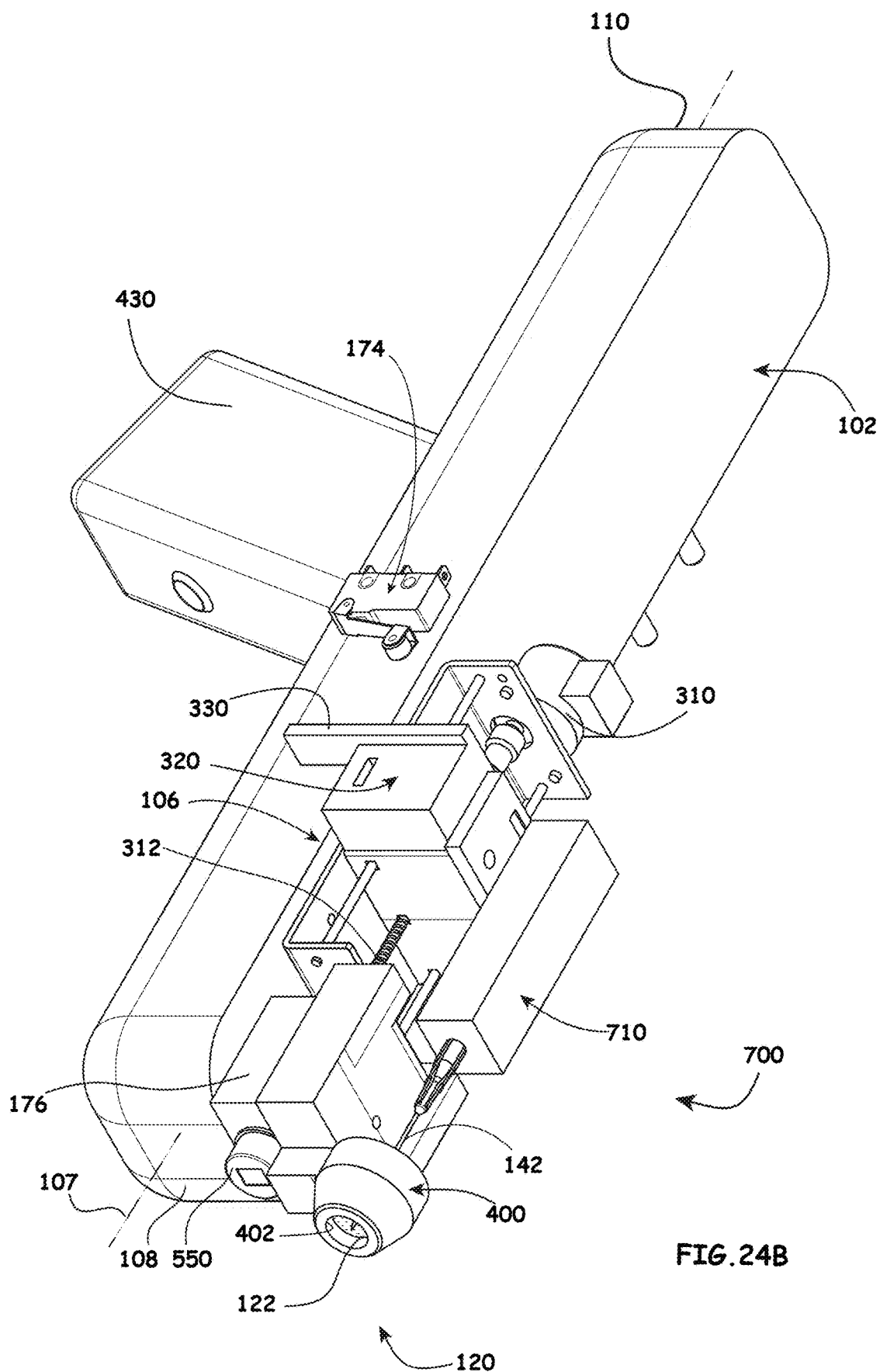

Reference is now made to FIGS. 24A & 24B, which are simplified two different pictorial illustrations of a handheld assembled MPAI with a needle assembly only, constructed and operative in accordance with yet another embodiment of the invention and showing the MPAI in a first operative orientation.

The MPAI 700 in accordance with another embodiment of the present invention is similar in most respects to MPAI 600, illustrated and described with reference to FIGS. 22A-23. It is a particular feature of an embodiment of the present invention that the MPAI 700 in accordance with another embodiment of the present invention includes a single electrical motor 310, which is operative for actuating the repetitive reciprocating motion of the needle 142 to deposit medicament 122 from cartridge 120 in various depths within the injection site. After depositing medicament 122 in various depths within the injection site, the device can be completely withdrawn and a second, independent needle and syringe could be used to inject the same, anesthetized site with medication. The MPAI 700 can also be used to introduce a finger-stick lancet into the skin (e.g. for a glucose blood sample), or an IV catheter, arterial catheter, piercing needle, or any other device to penetrate the skin painlessly with a variety of sharp instruments.

Like components are numerated with like reference numerals hereinbelow. A single carriage assembly 106 is fixedly attached onto the base unit 102, generally at an intermediate location thereof. The second driven element 320 is adapted to be axially displaceable relative to the second support element 300 of the carriage assembly 106 and thus relative to the base unit 102 upon actuation of the single electrical motor 310.

The needle hub 710 or any other piercing instrument is preferably fixedly attached to the driven element 320.

It is specifically seen in FIGS. 24A & 24B that the cartridge 120 is fixedly attached to the cartridge holder 176 of the base unit 102 or to the base unit 102 directly, adjacent the forward end 108 thereof. The medicament reservoir 400 preferably protrudes forwardly from the forward end 108 of the base unit 102.

It is a particular feature of an embodiment of the present invention that the needle hub 710 protrudes forwardly from the driven element 320, such that the needle 142 thereof is configured to be received into the inner volume of the medicament reservoir 400 of cartridge 120 through opening 404 thereof.

It is seen in FIGS. 24A & 24B that in accordance with one embodiment of the present invention, the cartridge 120 as illustrated in FIGS. 7A-7C is used. Alternatively, the cartridge 120 as illustrated in FIGS. 8A-8C may alternatively be used, so that the needle 142 penetrates the seal element 410 covering opening 404 to be partially received within the inner volume of the medicament reservoir 400.

It is a further particular feature of an embodiment of the present invention, as specifically seen in FIG. 24B, that the second engagement wall 330 of the second driven element 320 is adapted to be engageable with switch 174 in order to provide indication of a particular position of the driven element 320 relative to the medicament reservoir 400 of the cartridge 120. It is noted that the switch 174 is particularly operative for providing an indication of when the carriage assembly 106 returned to initial storage position.

The MPAI 700 is illustrated in FIGS. 24A & 24B in storage operative orientation, in which the needle 142 is protected and the forward end thereof is concealed within the inner volume of the medicament reservoir 400 of the cartridge 120, such that the forward protrusion length of the needle 142 from the medicament reservoir 400 is defined as L0.

It is a particular feature of an embodiment of the present invention that the forward end of the needle 142 protrudes into a material disposed within the medicament reservoir 400, whereas the material is absorbed with medicament, which is in turn deposited onto the outer surface of the needle 142.

It is particularly seen in FIGS. 24A & 24B that the carriage assembly 106 is disposed at its initial storage operative orientation where the driven element 320 is not yet displaced relative to the base unit 102, so that the forward end of the needle 142 is disposed within the medicament reservoir 400 of the cartridge 120 and is protected therewithin.

It is a particular feature of an embodiment of the present invention that a motion sensor 550, as particularly seen in FIG. 24B is coupled to the forward end of the cartridge 120 to indicate movement of the cartridge 120 from the injection site during operation of the MPAI 700. Particular use and advantage of the motion sensor 550 coupled to cartridge 120 is described in detail with reference to FIGS. 12A & 12B.

Figure 25:
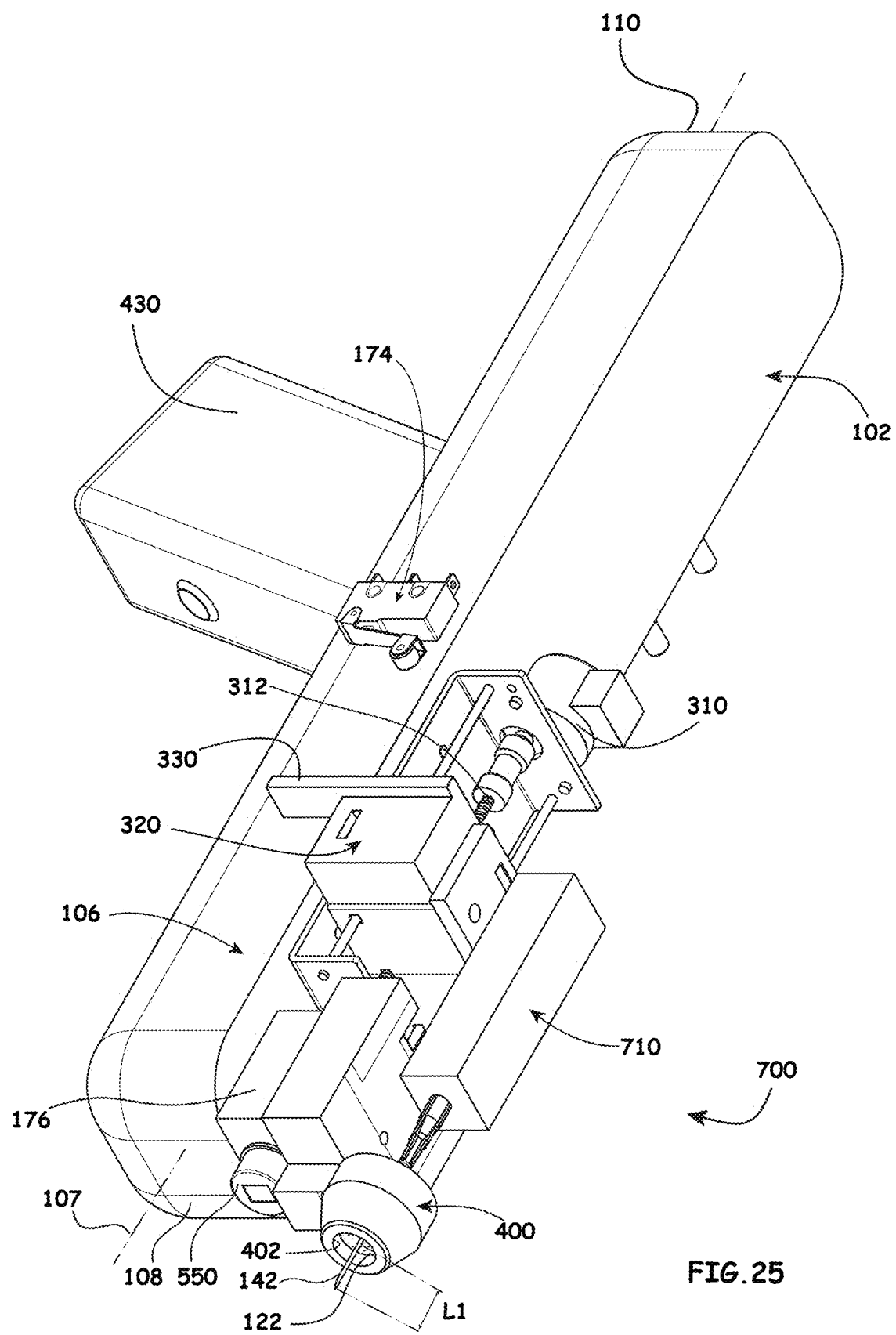
FIG. 25 is a simplified pictorial illustration of the handheld assembled MPAI of FIGS. 24A & 24B, showing the MPAI in a second operative orientation.

Reference is now made to FIG. 25, which is a simplified pictorial illustration of the handheld assembled MPAI 700 of FIGS. 24A & 24B, showing the MPAI 700 in a second operative orientation.

It is appreciated that all spatial relationships between the various components of the MPAI 700 remain the same as described hereinabove and illustrated in FIGS. 24A & 24B, besides the following:

The MPAI 700 is illustrated in FIG. 25 in a first stage of reciprocating motion operative orientation, in which the needle 142 protrudes forwardly from the medicament reservoir 400 of the cartridge 120 to a first longitudinal extent L1, thus the needle 142 protrudes into the injection site under the skin of the patient to an initial depth L1.

It is a particular feature of an embodiment of the present invention that the medicament from the medicament cartridge 400 of cartridge 120 that is deposited onto the outer surface of needle 142 is delivered at depth L1 at the injection site and is deposited there in a tattoo-like manner.

It is particularly seen in FIG. 25 that the carriage assembly 106 is disposed at its first stage of reciprocating motion operative orientation where the driven unit 320, along with the needle hub 710 and the needle 142 are together forwardly axially displaced relative to the base unit 102 to a longitudinal extent L1, so that the forward end of the needle 142 protrudes forwardly from the forward end of medicament reservoir 400 of cartridge 120 to a distance of L1.

It is a particular feature of an embodiment of the present invention that the first stage of reciprocating motion is a repetitive stage, in which multiple reciprocations of the needle 142 to a depth of L1 under the skin of the patient are typically performed in order to deposit a sufficient amount of medicament from the medicament reservoir 400 of the cartridge 120 into depth L1 at the injection site.

Upon receipt of an appropriate signal from the controller of the MPAI 700, the motor 310 is actuated and is operative to drive the second lead screw 312, which causes displacement of the second driven element 320 and thus the displacement of the needle hub 710 and the needle 142 therealong.

It is a particular feature of an embodiment of the present invention that the penetration depth of the needle 142 is controlled by the motor 310, thereby increasing the control and accuracy of needle depth penetration. The needle 142 is preferably displaced during its reciprocating motion according to specific algorithms related to the timing of a sequence of incremental increases in needle penetration depth, as described in detail hereinbelow. The specific algorithms can be selected by the user by means of mechanical or digital inputs, such as user input elements 170, for example, as described in detail hereinabove.

In accordance with an algorithm controlling the operation of the MPAI 700, as described in detail hereinabove, during each reciprocation of the needle 142, the driven element 320 is displaced axially forwardly relative to base unit 102 to distance L1 and returns axially rearwardly relative to the base unit 102 to distance L0, as specifically illustrated in FIGS. 24A & 24B.

It is noted that all of the alternative embodiments related to the various components of the MPAI 100 and the method of use thereof are applicable to the same extent in MPAI 700.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

The invention claimed is:

1. A multi-purpose automatic injector for use with a syringe containing a first medicament and having a needle attached to one end thereof and a plunger inserted into said syringe at another end thereof and being slidably displaceable with respect thereto, comprising:
   a base unit having a forward end and a rearward end and arranged along a longitudinal axis;
   a cartridge containing a second medicament, said cartridge being coupled adjacent to the forward end of said base unit;
   a drive assembly attached to said base unit and configured to be operatively coupled with said syringe;
   wherein, in a first mode of operation, said drive assembly is configured to displace said syringe with said needle relative to said base unit, such that said needle moves relative to said cartridge in a reciprocating manner; and in a second mode of operation, said drive assembly is configured to displace said plunger rod relative to said syringe to effect ejection of fluid therefrom.

2. The multi-purpose automatic injector according to claim 1, also comprising a computerized controller configured to govern said drive assembly, which comprises one motor.

3. The multi-purpose automatic injector according to claim 1, also comprising a computerized controller configured to govern said drive assembly, which comprises two motors.

4. The multi-purpose automatic injector according to claim 1, and wherein in said first mode of operation, said second medicament is caused to be deposited into an injection site using an outer surface of said needle and in said second mode of operation, said first medicament is caused to be injected into said injection site through said needle.

5. The multi-purpose automatic injector according to claim 2, and wherein said computerized controller utilizes an automated algorithm to govern movement of said syringe relative to said cartridge.

6. The multi-purpose automatic injector according to claim 2, also comprising at least one sensor, which is operatively coupled to said computerized controller and configured to provide an output indication if said base unit or said cartridge is disengaged from the skin of a patient or if pressure on the skin of the patient is reduced beyond a particular threshold value.

7. The multi-purpose automatic injector according to claim 6, and wherein said computerized controller is configured to disable movement of said at least one needle relative to said cartridge and to retract said needle into said cartridge upon receipt of said output indication from said at least one sensor.

8. The multi-purpose automatic injector according to claim 1, also comprising a heating mechanism operatively coupled thereto and configured to transmit heat to the second medicament.

9. A multi-purpose automatic injector, comprising:
   a base unit having a forward end and a rearward end and arranged along a longitudinal axis;
   a cartridge containing a medicament, said cartridge being coupled adjacent to the forward end of said base unit;
   a drive assembly attached to said base unit and configured to be actuated by a computerized controller;
   at least one piercing element configured to be operatively coupled with said drive assembly and configured to be movable by said drive member relative to said cartridge in a reciprocating manner upon receipt of a corresponding signal from said computerized controller.

10. The multi-purpose automatic injector according to claim 9, and wherein said computerized controller utilizes an automated algorithm to govern movement of said at least one needle relative to said cartridge.

11. The multi-purpose automatic injector according to claim 9, also comprising at least one sensor, which is operatively coupled to said computerized controller and configured to provide an output indication if said base unit or said cartridge is disengaged from the skin of a patient or if pressure on the skin of the patient is reduced beyond a particular threshold value.

12. The multi-purpose automatic injector according to claim 11, and wherein said computerized controller is configured to disable movement of said at least one piercing element relative to said cartridge and to retract said piercing element into said cartridge upon receipt of said output indication from said at least one sensor.

13. The multi-purpose automatic injector according to claim 9, and wherein said piercing element is one of a needle connected to a vacuum collection tube, an intravascular catheter, a finger-stick lancet, a hypodermic needle, a piercing needle and an abrading bur secured to a chuck of a rotary tool.

14. The multi-purpose automatic injector according to claim 9, and wherein said drive assembly comprises one motor.

15. The multi-purpose automatic injector according to claim 9, and wherein said drive assembly comprises two motors.

16. The multi-purpose automatic injector according to claim 9, also comprising a heating mechanism operatively coupled thereto and configured to transmit heat to the medicament.

17. A method of operating a multi-purpose automatic injector, comprising the steps of:
provide a base unit having a forward end and a rearward end and arranged along a longitudinal axis; a cartridge containing a medicament, said cartridge being coupled adjacent to the forward end of said base unit; a drive assembly attached to said base unit and configured to be actuated by a computerized controller;
utilizing an automated algorithm for providing a suitable signal to said computerized controller for:
first longitudinally displacing at least one piercing element, which is configured to be operatively coupled with said drive assembly, relative to said cartridge so that said at least one piercing element protrudes to a first length from a forward end of said cartridge;
and subsequently longitudinally displacing said at least one piercing element relative to said cartridge in an incremental manner, so that during at least one of said subsequent displacements of said at least one piercing element relative to said cartridge, said at least one piercing element protrudes from a forward end of said cartridge to a second length, whereas said second length is greater than said first length.

18. The method of claim 17, and wherein said at least one piercing element is displaced relative to said cartridge in such manner that with each displacement said at least one piercing element protrudes from a forward end of said cartridge to a greater longitudinal extent, such that at least said first length corresponds to a deposition area disposed superficially to the nociceptors in the skin of the patient prior to reaching a pre-defined length that corresponds to a deposition area in the skin of the patient that is disposed at the level of said nociceptors in the skin or deeper thereof.

19. The method of claim 18, and wherein the magnitude of the increments of said longitudinal displacement of said at least one piercing element relative to said forward end of said cartridge is dictated by the user during mode selection procedure, whereby the user anticipates the depth of the nociceptors in the skin of the patient.

20. The method of claim 17, and wherein following said first displacement of said at least one piercing element, said automated algorithm initiates a sequence of reciprocations and incremental linear advancements of said at least one piercing element such that local anesthesia, which is disposed within said cartridge is deposited into the skin of the patient at progressively increasing depths until a desired final depth has been reached.

* * * * *